United States Patent
Ohlmeyer et al.

(10) Patent No.: US 9,937,186 B2
(45) Date of Patent: Apr. 10, 2018

(54) SULFONAMIDES DERIVED FROM TRICYCLYL-2-AMINOCYCLOALKANOLS AS ANTICANCER AGENTS

(71) Applicant: ICAHN SCHOOL OF MEDICINE AT MOUNT SINAI, New York, NY (US)

(72) Inventors: Michael Ohlmeyer, Plainsboro, NJ (US); David Kastrinsky, Fair Lawn, NJ (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 0 days.

(21) Appl. No.: 15/124,891

(22) PCT Filed: Mar. 10, 2015

(86) PCT No.: PCT/US2015/019770
§ 371 (c)(1),
(2) Date: Sep. 9, 2016

(87) PCT Pub. No.: WO2015/138500
PCT Pub. Date: Sep. 17, 2015

(65) Prior Publication Data
US 2017/0015625 A1    Jan. 19, 2017

Related U.S. Application Data

(60) Provisional application No. 61/951,237, filed on Mar. 11, 2014.

(51) Int. Cl.
| | | |
|---|---|---|
| A61K 31/517 | (2006.01) |
| A61K 31/55 | (2006.01) |
| A61K 31/18 | (2006.01) |
| C07C 311/29 | (2006.01) |
| C07D 243/38 | (2006.01) |
| C07D 471/04 | (2006.01) |
| C07D 265/38 | (2006.01) |
| C07D 267/18 | (2006.01) |
| C07D 495/04 | (2006.01) |
| C07D 209/86 | (2006.01) |
| C07D 487/04 | (2006.01) |

(52) U.S. Cl.
CPC .............. *A61K 31/55* (2013.01); *A61K 31/18* (2013.01); *A61K 31/517* (2013.01); *C07C 311/29* (2013.01); *C07D 209/86* (2013.01); *C07D 243/38* (2013.01); *C07D 265/38* (2013.01); *C07D 267/18* (2013.01); *C07D 471/04* (2013.01); *C07D 487/04* (2013.01); *C07D 495/04* (2013.01); *C07C 2601/08* (2017.05); *C07C 2601/14* (2017.05); *C07C 2603/18* (2017.05)

(58) Field of Classification Search
CPC ....... A61K 31/18; A61K 31/517; A61K 31/55

USPC .......................................................... 514/217
See application file for complete search history.

(56) References Cited

U.S. PATENT DOCUMENTS

| | | | |
|---|---|---|---|
| 4,634,766 | A | 1/1987 | Atkinson et al. |
| 4,668,671 | A | 5/1987 | Gribble et al. |
| 4,882,351 | A | 11/1989 | Oshima et al. |
| 6,583,138 | B1 | 6/2003 | Miyamoto et al. |
| 9,540,358 | B2 | 1/2017 | Ohlmeyer et al. |
| 2002/0103189 | A1 | 8/2002 | Miyamoto et al. |
| 2008/0275023 | A1 | 11/2008 | Guidi et al. |

(Continued)

FOREIGN PATENT DOCUMENTS

| | | |
|---|---|---|
| CN | 102942562 A | 2/2013 |
| EP | 0679641 A1 | 11/1995 |

(Continued)

OTHER PUBLICATIONS

Zhang et al, "Akt, FoxO and regulation of apoptosis," Biochimica et Biophysica Acta, 2011, vol. 1813, pp. 1978-1986.*

(Continued)

*Primary Examiner* — Kathrien A Cruz
*Assistant Examiner* — Janet L. Coppins
(74) *Attorney, Agent, or Firm* — Heslin Rothenberg Farley & Mesiti P.C.

(57) ABSTRACT

A genus of arylsulfonamide derivatives of aminocycloalkanols is disclosed. The compounds are of the following genus:

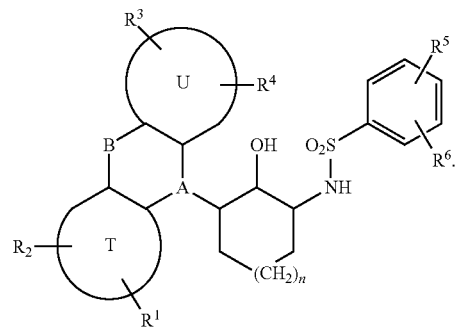

The compounds induce FOXO1 transcription factor translocation to the nucleus by modulating PP2A and, as a consequence, exhibit anti-proliferative effects. They are useful in the treatment of a variety of disorders, including as a monotherapy in cancer treatment, or used in combination with other drugs to restore sensitivity to chemotherapy where resistance has developed.

19 Claims, No Drawings

(56) References Cited

U.S. PATENT DOCUMENTS

| | | |
|---|---|---|
| 2015/0376191 A1 | 12/2015 | Ohlmeyer et al. |
| 2017/0015630 A1 | 1/2017 | Ohlmeyer et al. |

FOREIGN PATENT DOCUMENTS

| | | | |
|---|---|---|---|
| EP | 0881220 A1 | 12/1998 | |
| WO | 2004052847 A2 | 6/2004 | |
| WO | 2006116157 A2 | 11/2006 | |
| WO | 2006117183 A1 | 11/2006 | |
| WO | 2013025882 A2 | 2/2013 | |
| WO | WO2013025882 A2 * | 2/2013 | ........... C07D 417/04 |
| WO | 2014031986 A1 | 2/2014 | |
| WO | 2014130534 A1 | 8/2014 | |
| WO | 2015138496 A1 | 9/2015 | |
| WO | 2017/024229 A1 | 2/2017 | |
| WO | 2017/044567 A1 | 3/2017 | |
| WO | 2017/044569 A1 | 3/2017 | |
| WO | 2017/044571 A1 | 3/2017 | |
| WO | 2017/044572 A1 | 3/2017 | |
| WO | 2017/044575 A1 | 3/2017 | |

OTHER PUBLICATIONS

Extended EP Search Report for EP 12823881.3 dated Mar. 3, 2015.
International Search Report for PCT/US2012/051097 dated Feb. 20, 2013.
International Search Report for PCT/US2014/017127 dated May 20, 2014.
Alfredsson et al., "Mass Fragmentographic Analysis of Clomipramine and Its Mono-Demethylated Metabolite in Human Plasma" Psychopharmacology, 52, 25-30 (1977).
Midgley et al., "Synthesis of [13C$_2$]-Amitriptyline, Nortriptyline and Desmethynortriptyline" Journal of Labelled Compounds and Radiopharmaceuticals, vol. XV, pp. 511-521 (1978).
Hadrich et al., "Synthesis and Characterization of Fluorescent Ligands for the Norepinephrine Transporter: Potential Neuroblastoma Imaging Agents", J. Med. Chem., 1999, (published on web Jul. 16, 1999).
Runyon et al., "Influence of Chain Length and N-Alkylation on the Selective Serotonin Receptor Ligand 9-(Aminomethyl)-9,10-dihydroanthracene", Bioorganic & Medicinal Chemistry Letters 11 (2001), 655-658.
Van Dort et al., Synthesis of $^{11}$C-Labeled Desipramine and its Metabolite 2-Hydroxydesipramine: Potential Radiotracers for PET Studies of the Norepinephrine Transporter, Nuclear Medicine & Biology, vol. 24, pp. 707-711, 1997.
Ilies et al., "Protease Inhibitors: Synthesis of Bacterial Collagenase and Matrix Metalloproteinase Inhibitors Incorporating Arylsulfonylureido and 5-Dibenzo-suberenyl/suberyl Moieties", Bioorganic & Medicinal Chemistry, 11 (2003) 2227-2239.
Yang et al., "Catalytic decarboxylative alkylationof B-keto acids with sulfonamides via the cleavage of carbon-nitrogen and carbon-carbon bonds," Chemical Communications, 2011 (published on Web: Jun. 22, 2011), vol. 47, No. 29, pp. 8343-8345.
Azuine et al., "Cancer chemopreventive effect of phenothiazines and related tri-heterocyclic analogues in the 12-0-tetradecanoylphorbol-13-acetate promoted Epstein-Barr virus early antigen activation and the mouse skin two-stage carcinogenes is models," Pharmacological Research, 2004, vol. 49, No. 2, pp. 161-169.
Ohshima, et al., "Non-Prostanoid Thromboxane A$_2$ Receptor Antagonists with a Dibenzoxepin Ring System. 2" J. Med. Chem, 1992, 35, 3402-3413.
Morak-Mlodawska et al., "Acyl and Sulfonyl Derivatives of 10-Aminoalkyl-2,7-Diazaphenothiazines#, Hetrocycles", vol. 78, No. 5, 2009.
Alfonso et al., "Synthesis of a C$_{11}$ Spiropiperdino derivative of 8-Chloro-6,11-dihydro 5H—Benzo [5,6] cyclohepta[1,2-b]pyridine", Tetrahedron Letters 39, 1998, 7661-7664.
Kau et al., A chemical genetic screen identifies inhibitors of regulated nuclear export of a Forkhead transcription factor in PTEN-deficient tumor cells, Cancer Cell, XP008037524, Dec. 2003.
Jelen et al., "Synthesis of 6-Aminoalkyldiquino-1,4-Thiazines and Their Acyl and Sulfonyl Derivatives, Heterocycles", vol. 4, No. 4, XP055279565, 2008.
Pluta et al., "Anticancer activity of newly synthesized azaphenothiazines from NCI's anticancer screening bank#", Pharmaceutical Reports, 2010, 62, 319-332.
Motohashi et al., "Synthesis and Biological Activity of N-acylphenothiazines" International Journal of Antimicrobial Agents, 2000, pp. 203-207, vol. 14.
Database PubChemCompound, "N-[4-methoxy-3-(3-phenothiazin-10-ylpropylsulfamoyl)phenyl]acetamide," URL: http://pubchem.ncbi.nlm.nih.gov/search.cgi, 2005-2009.
International Search Report for PCT/US2015/019764 dated May 8, 2015.
International Search Report for PCT/US2016/050685 dated Oct. 18, 2016.
International Search Report for PCT/US2016/050688 dated Oct. 18, 2016.
International Search Report for PCT/US2016/045779 dated Sep. 30, 2016.
International Search Report for PCT/US2016/050690 dated Oct. 18, 2016.
International Search Report for PCT/US2016/050696 dated Oct. 18, 2016.
International Search Report for PCT/US2016/050692 dated Oct. 18, 2016.
O'Brien et al., "cis- and trans-Stereoselective Epoxidation of N-protected 2-Cyclohexen-l-ylamines," Organic Letters, 2003, 14(23), 6012-6015.
International Search Report & Written Opinion issued in PCT/US2015/019770, dated May 8, 2015.
RN 1350122-38-1 CAS Registry, entered STN: Dec. 7, 2011.

* cited by examiner

SULFONAMIDES DERIVED FROM TRICYCLYL-2-AMINOCYCLOALKANOLS AS ANTICANCER AGENTS

CROSS REFERENCE TO RELATED APPLICATIONS

This application is a U.S. National Phase filing under 35 U.S.C. § 371 of International Application PCT/US2015/019770, filed Mar. 10, 2015, and published as WO 2015/138500 on Sep. 17, 2015. PCT/US2015/019770 claims priority of U.S. provisional application 61/951,237, filed Mar. 11, 2014. The entire contents of each of the prior applications are incorporated herein by reference.

FIELD OF THE INVENTION

The invention relates to the use of tricyclic chemical modulators of PP2A, comprising 2-sulfonamido-tricyclyl-cycloalkanols to treat diseases such as cancer, neurodegenerative disease and other disorders.

BACKGROUND

The FOXO (Forkhead transcription factors, Class O) proteins are a group of transcription factors involved in control of a variety of physiological, metabolic and developmental pathways. They are downstream effectors in a number of signaling pathways including insulin and growth factor signaling; they are also regulated by oxidative stress and nutrient deprivation. Cellular processes affected by FOXO activity include cell cycle control, differentiation, proliferation and apoptosis. Disregulation of FOXO mediated processes has been implicated in a number of pathologies including tumorigenesis, inflammation, diabetes and neurodegenerative conditions amongst others. Activity of FOXO transcription factors are controlled in part by their sub-cellular localization, in particular their localization to the nucleus from the cytosol, and their subsequent transcriptional activation.

Four FOXO proteins designated FOXO1, FOXO3a, FOXO4 and FOXO6 are present in human cells and their activity is controlled by a variety of mechanisms including stability (proteolytic cleavage), sub-cellular localization and transcriptional activation. Activity of the first three members of the family is controlled by cytosolic-nuclear translocation.

FOXO1 regulates expression of a number of genes that play critical roles in cell cycle and apoptosis. A pivotal regulatory mechanism of FOXO is reversible phosphorylation, catalyzed by kinases and phosphatases. Phosphorylation of FOXO1 is associated with 14-3-3 binding and cytosolic localization, whereas dephosphorylated FOXO1 translocates to the nucleus and is transcriptionally active.

Protein phosphatase 2A is one of the four major serine threonine phosphatases and is implicated in the negative control of cell growth and division. Protein phosphatase 2A holoenzymes are heterotrimeric proteins composed of a structural subunit A, a catalytic subunit C, and a regulatory subunit B. The PP2A heterotrimeric protein phosphatase is a ubiquitous and conserved phosphatase with broad substrate specificity and diverse cellular functions. Among the targets of PP2A are proteins of oncogenic signaling cascades, such as Raf, MEK, and AKT.

PP2A interacts directly with FOXO1 and dephosphorylates FOXO1. Inhibition of PP2A phosphatases rescues FOXO1-mediated cell death by regulating the level of the proapoptotic protein BIM. In addition, PP2A directly regulates FOXO3a subcellular localization and transcriptional activation. Without wishing to be held to any particular theory, it may be that the compounds described herein promote apoptosis by acting on FOXO transcription factors via activation of PP2A.

Prostate cancer is the second leading cause of cancer death in men in America, behind lung cancer. According to the American Cancer Society, approximately 1 man in 36 will die of prostate cancer. Male hormones, specifically testosterone, fuel the growth of prostate cancer. By reducing the amount and activity of testosterone, the growth of advanced prostate cancer is slowed. Endocrine therapy, known as androgen ablation, is the first line of treatment for metastatic prostate cancer. Androgen deprivation therapy for metastatic prostate cancer results in tumor regression and symptomatic improvement in the majority of patients. However, metastatic prostate cancer inevitably progresses despite castrate levels of serum testosterone. Several new therapies have been approved for patients with castration-resistant prostate cancer (CRPC); however, none are curative and tumors ultimately develop resistance. To combat CRPC new approaches and novel therapies are required.

Breast cancer can affect both men and women. Breast cancer is the most prevalent cancer in women, after skin cancers, with about 1 in every 8 women expected to develop invasive breast cancer at some point. One subset of breast cancer expresses the androgen receptor (AR), which has been implicated as a therapeutic target in that subset. About 10-20% of breast cancers—more than one out of every 10—are found to be triple-negative. "Triple negative breast cancer" refers to a breast cancer that does not contain estrogen receptors, progesterone receptors, or human epidermal growth factor receptor 2 (HER2). This means that the growth of the cancer is not supported by the hormones estrogen and progesterone, nor by the presence of too many HER2 receptors. Therefore, triple-negative breast cancer does not respond to hormonal therapy (such as tamoxifen or aromatase inhibitors) or therapies that target HER2 receptors, such as Herceptin (chemical name: trastuzumab). While these tumors are often treatable, the chemotherapy is not targeted, and response durations are short. For doctors and researchers, there is intense interest in finding new medications that can treat breast cancer.

The compounds described herein, which are based on a 2-aminocycloalkanol scaffold, exhibit anti-proliferative effects and are useful as monotherapy in cancer treatment. Additionally, they can be used in combination with other drugs to restore sensitivity to chemotherapy where resistance has developed.

SUMMARY OF THE INVENTION

A genus of arylsulfonamide derivatives of aminocycloalkanols has now been found that induce FOXO1 transcription factor translocation to the nucleus by modulating PP2A. The compounds described herein exhibit anti-proliferative effects, and are useful in the treatment of a variety of disorders, including as a monotherapy in cancer treatment, or used in combination with other drugs to restore sensitivity to chemotherapy where resistance has developed.

In a first aspect the invention relates to compounds of formula (I):

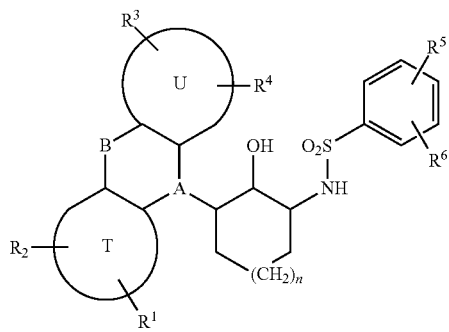

wherein:
B is selected from the group consisting of: direct bond, —O—, —(CH$_2$—O)—, —(O—CH$_2$)—, —C(=O)N(CH$_3$)— and —N(CH$_3$)C(=O)—;
A is selected from N and CH;
T is a benzene ring or a five or six membered heteroaromatic ring;
U is a benzene ring or a five or six membered heteroaromatic ring;
n is zero, 1 or 2;
$R^1$, $R^2$, $R^3$ and $R^4$ are chosen independently from H, OH, halogen, cyano, nitro, (C$_1$-C$_3$)alkylamino, (C$_1$-C$_3$)dialkylamino, (C$_1$-C$_3$)acylamino, (C$_1$-C$_3$)alkylsulfonyl, (C$_1$-C$_3$)alkylthio, (C$_1$-C$_3$)alkyl, (C$_1$-C$_3$)haloalkyl, (C$_1$-C$_3$)haloalkoxy, —CC(=O)O(C$_1$-C$_3$)alkyl, and (C$_1$-C$_3$)alkoxy;
$R^5$ and $R^6$ are chosen independently from H, halogen, cyano, nitro, azido, (C$_1$-C$_3$)haloalkyl, (C$_1$-C$_3$)haloalkoxy, and (C$_1$-C$_3$) haloalkylthio.

In a second aspect, the invention relates to methods and uses of the above-described compounds in medicine, particularly for the treatment of a disease chosen from: (a) cancer; (b) diabetes; (c) autoimmune disease; (d) age onset proteotoxic disease; (e) mood disorder; (f) acne vulgaris; (g) solid organ transplant rejection; (h) graft vs. host disease; (i) cardiac hypertrophy; (j) viral infection; (k) parasitic infection; (l) autism; (m) schizophrenia and (n) psychostimulant abuse. These methods include administering to a patient a therapeutically effective amount of a compound described above.

In a third aspect, the invention relates to a method for restoring sensitivity to one or more chemotherapeutic agents in the treatment of cancer. The method includes administering an effective amount of a compound described above.

In a fourth aspect, the invention relates to a method for treating a disease or disorder in a patient where the disease or disorder involves the dysregulation of PP2A influenced signaling cascades such as the PI3K-AKT, MAP kinase and mTOR pathways. These methods include administering to a patient a therapeutically effective amount of a compound described above.

In a fifth aspect, the invention relates to pharmaceutical compositions comprising the above-described compounds.

DETAILED DESCRIPTION OF THE INVENTION

Substituents are generally defined when introduced and retain that definition throughout the specification and in all independent claims.

In a composition aspect, the invention relates to compounds of formula (I):

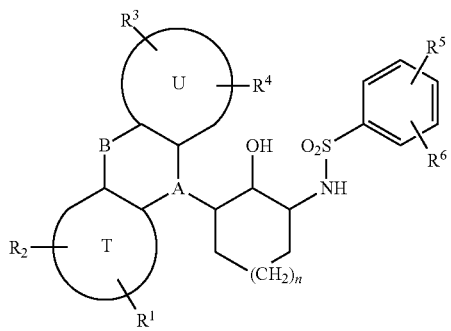

as described above.

In some embodiments, the invention relates to compounds of formula (II):

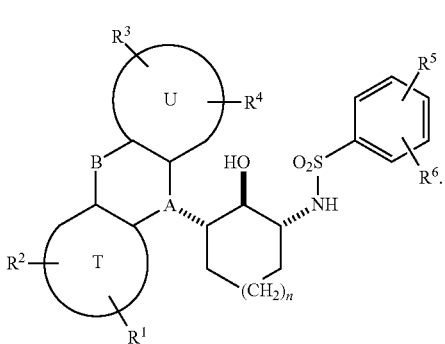

In some embodiments, the invention relates to compounds of formula (IIIa) or IIIb:

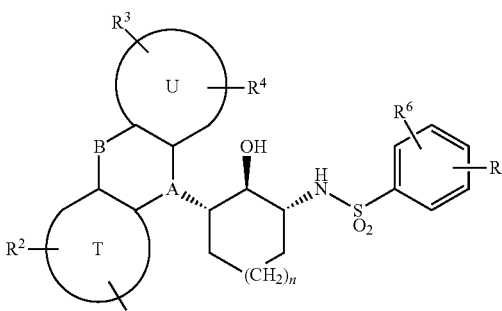

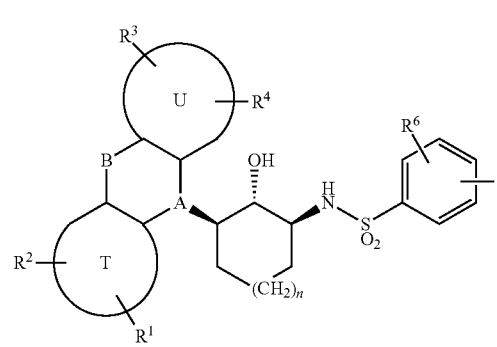

In the embodiments described below, the compound may be of formula I, II, IIIa or IIIb, unless otherwise indicated.

In some embodiments, n is one. These compounds may be envisioned as N-arylsulfonyl derivatives of 2-aminocyclohexanol:

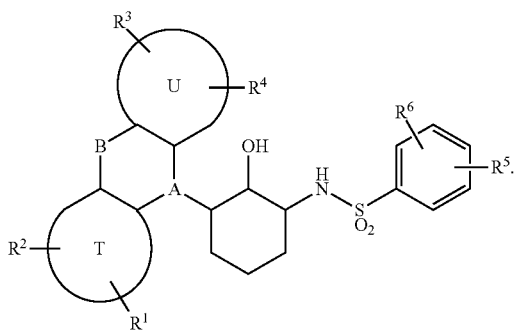

In some embodiments, n is zero. These compounds may be envisioned as N-arylsulfonyl derivatives of 2-aminocyclopentanol:

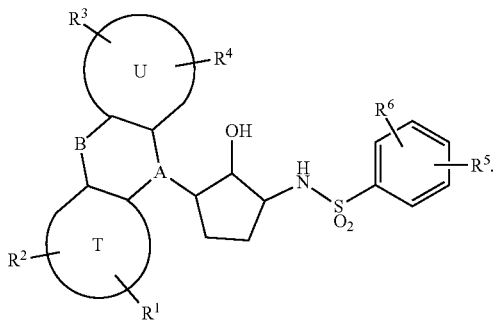

In some embodiments, n is two. These compounds may be envisioned as N-arylsulfonyl derivatives of 2-aminocycloheptanol:

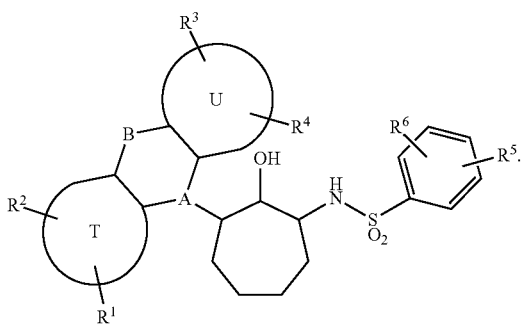

In any of the foregoing subgenera (cyclohexanol, cyclopentanol or cycloheptanol), preferred cycloalkanols are those in which the relative configurations are such that the amine and the tricycle are both trans to the alcohol:

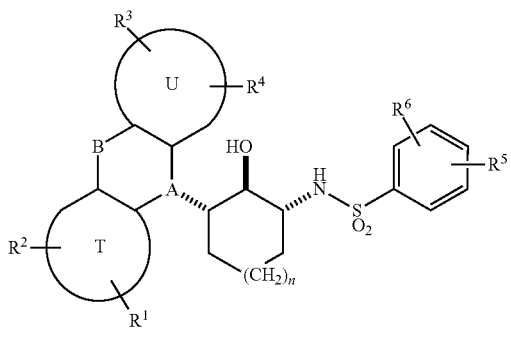

In this trans: trans subgroup, compounds can be either single enantiomers IIIa and IIIb or a mixture of the two. If a mixture, the mixture will most commonly be racemic, but it need not be. Substantially pure single enantiomers of biologically active compounds such as those described herein often exhibit advantages over their racemic mixture.

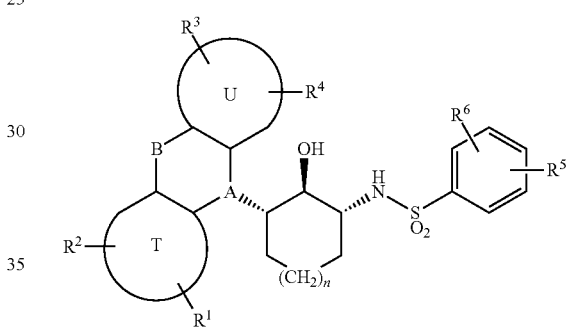

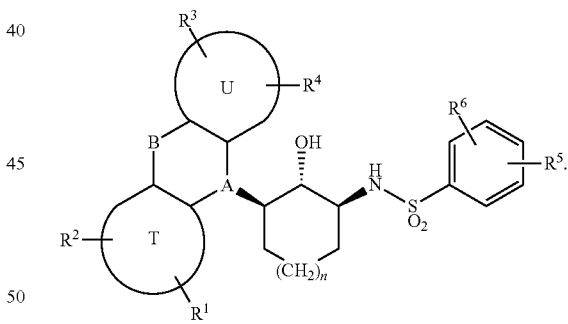

In any of the foregoing subgenera (cyclohexanol, cyclopentanol or cycloheptanol), A may be N or CH. In both the N-series and the CH series, B may be a direct bond, —O—, —(CH$_2$—O)—, —(O—CH$_2$)—, —C(=O)N(CH$_3$)— or —N(CH$_3$)C(=O)—.

In some embodiments, at least one of T and U is a heterocycle such as pyridine, pyrimidine, diazine, thiophene, thiazole, oxazole, imidazole, pyrrole, or furan. In some embodiments, one of T and U is a benzene ring, and the other of T and U is selected from pyridine, pyrimidine, and thiophene. In other embodiments, T and U are both benzene rings.

When B is a direct bond, T and U are benzene rings and A is N, a subgenus of cycloalkanols in which the tricyclic substituent is a carbazole results:

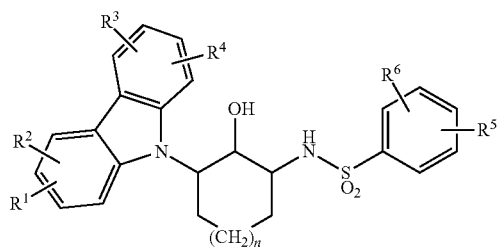

When B is —O—, T and U are benzene rings and A is N, a subgenus of cycloalkanols in which the tricycle is a dibenzooxazine results:

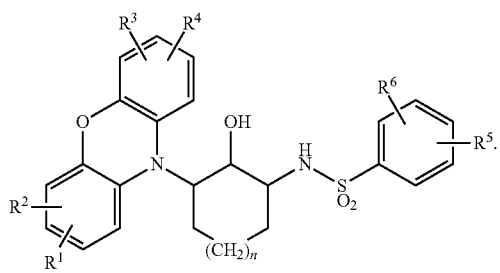

When B is —(CH₂—O)— or —(O—CH₂)—, T and U are benzene rings and A is N, two subgenera of cycloalkanols in which the tricyclic substituent is a dibenzooxazepine result:

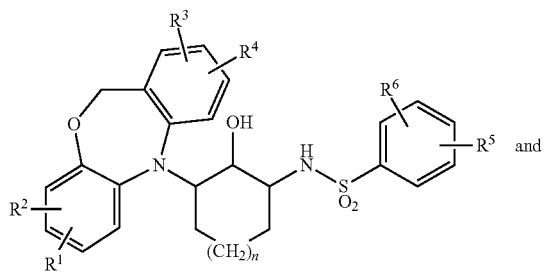

When B is —C(=O)N(CH₃)— or —N(CH₃)C(=O)—, T and U are benzene rings and A is N, two subgenera of cycloalkanols in which the tricyclic substituent is a dibenzodiazepine result:

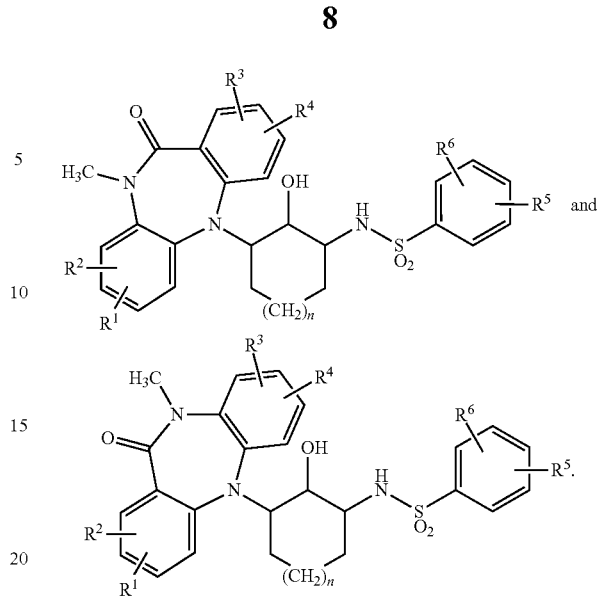

When B is a direct bond, T and U are benzene rings and A is CH, a subgenus of cycloalkanols in which the tricyclic substituent is a fluorene results:

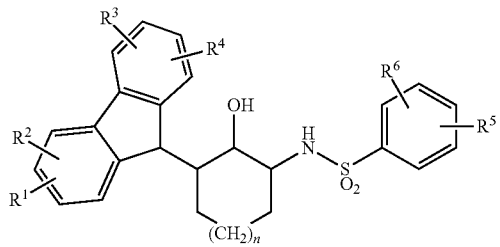

In some embodiments, $R^2$ and $R^4$ are H, and $R^1$ and $R^3$ are chosen independently from H, OH, F, Cl, Br, CN, $CO_2CH_3$, $CH_3$, $CF_3$, $OCF_3$, and $OCH_3$. In some embodiments, all of $R^1$, $R^2$, $R^3$ and $R^4$ are H. In some embodiments, at the least one of $R^1$, $R^2$, $R^3$ and $R^4$ is located at a carbon two positions away from a bridgehead carbon. In some embodiments, $R^5$ is H, and $R^6$ is chosen from H, F, Cl, $CF_3$, $OCF_3$, $SCF_3$, $N_3$ and —CN. Often $R^6$ is in the para position.

In summary, the invention relates to:

[1]. A compound of formula I, II, IIIa or IIIb.
[2]. A compound according to [1] above wherein n is one.
[3]. A compound according to [1] above wherein n is two.
[4]. A compound according to [1] above wherein n is three.
[5]. A compound according to any of [1] through [4] above wherein B is a direct bond.
[6]. A compound according to any of [1] through [4] above wherein B is —O—.
[7]. A compound according to any of [1] through [4] above wherein B is —(CH₂—O)— or —(O—CH₂)—.
[8]. A compound according to any of [1] through [4] above wherein B is —C(=O)N(CH₃)— or —N(CH₃)C(=O)—.
[9]. A compound according to any of [1] through [8] above wherein A is N.
[10]. A compound according to any of [1] through [8] above wherein A is CH.
[11]. A compound according to any of [1] through [10] above wherein T and U are both benzene rings.

[12]. A compound according to any of [1] through [10] above wherein at least one of T and U is chosen from pyridine, pyrimidine, diazine, thiophene, thiazole, oxazole, imidazole, pyrrole, and furan.

[13]. A compound according to any of [1] through [10] or [12] above, wherein one of T and U is a benzene ring, and the other of T and U is selected from pyridine, pyrimidine, and thiophene.

[14]. A compound according to any of [1] through [13] above, wherein $R^2$ and $R^4$ are H, and $R^1$ and $R^3$ are chosen independently from H, OH, F, Cl, Br, CN, $CO_2CH_3$, $CH_3$, $CF_3$, $OCF_3$, and $OCH_3$.

[15]. A compound according to any of [1] through [14] above, wherein all of $R^2$, $R^3$ and $R^4$ are H.

[16]. A compound according to any of [1] through [15] above, wherein at least one of $R^2$, $R^3$ and $R^4$ is located at a carbon two positions away from a bridgehead carbon.

[17]. A compound according to any of [1] through [16] above, wherein $R^5$ is H, and $R^6$ is chosen from H, F, Cl, $CF_3$, $SCF_3$, $OCF_3$, $N_3$ and CN.

[18]. A compound according to any of [1] through [17] above, wherein $R^6$ is in the para position.

The compounds described herein contain three or more asymmetric centers and may thus give rise to enantiomers, diastereomers, and other stereoisomeric forms which may be defined in terms of absolute stereochemistry as (R)- or (S)-. The present invention is meant to include all such possible diastereomers as well as their racemic and optically pure forms. Optically active (R)- and (S)-isomers may be prepared using homo-chiral synthons or homo-chiral reagents, or optically resolved using conventional techniques. When the compounds described herein contain olefinic double bonds or other centers of geometric asymmetry, and unless specified otherwise, it is intended to include both (E)- and (Z)-geometric isomers. Likewise, all tautomeric forms are intended to be included.

The graphic representations of racemic, ambiscalemic and scalemic or enantiomerically pure compounds used herein are a modified version of the denotations taken from Maehr J. Chem. Ed. 62, 114-120 (1985): simple lines provide no information about stereochemistry and convey only connectivity; solid and broken wedges are used to denote the absolute configuration of a chiral element; solid and broken bold lines are geometric descriptors indicating the relative configuration shown but not necessarily denoting racemic character; and wedge outlines and dotted or broken lines denote enantiomerically pure compounds of indeterminate absolute configuration. For example, the graphic representation

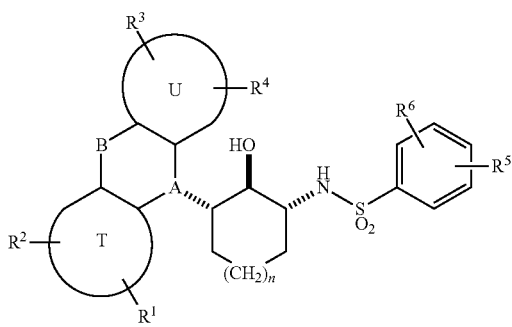

indicates either, or both, of the two trans: trans enantiomers:

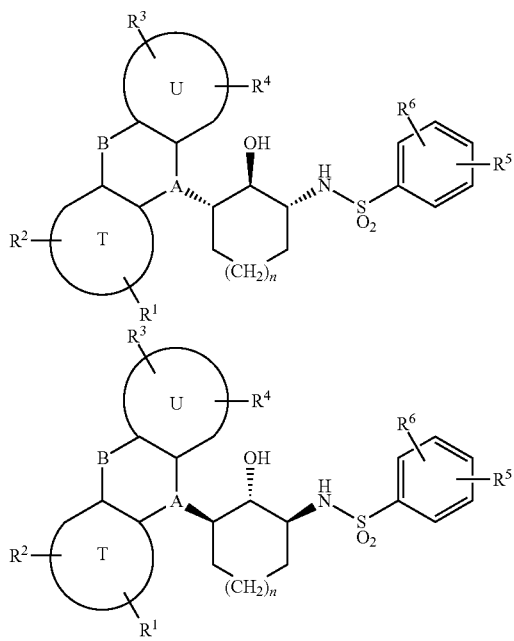

in any ratio, from pure enantiomers to racemates. The graphic representation:

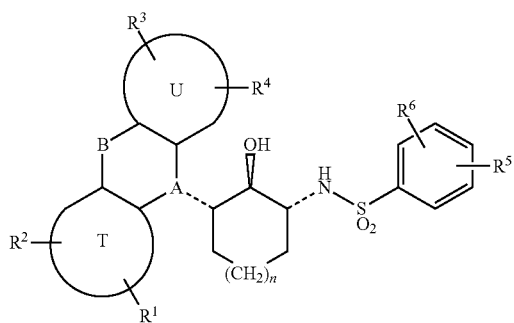

indicates a single enantiomer of unknown absolute stereochemistry, i.e. it could be either of the two preceding structures, as a substantially pure single enantiomer. And, finally, the representation:

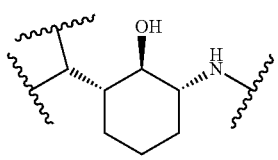 [SMILES: *N[C@@H]1CCC[C@H](C(*)*)[C@H]1O]

indicates a pure (1R,2R,6S)-2-amino-6-(C-attached tricycle) cyclohexanol. For the purpose of the present disclosure, a "pure" or "substantially pure" enantiomer is intended to mean that the enantiomer is at least 95% of the configuration shown and 5% or less of other enantiomers. Similarly, a "pure" or "substantially pure" diastereomer is intended to mean that the diastereomer is at least 95% of the relative configuration shown and 5% or less of other diastereomers. In the text describing the stereochemistry of the examples, the convention of Chemical Abstracts is used. Thus "(1R, 2R,6S)-rel-" indicates that the three chiral centers are in that relative relationship, which would be depicted in a structural diagram by solid bold and dashed lines, whereas "(1R,2R, 6S)" without the "rel" indicates a single enantiomer of that absolute configuration, which would be depicted in a structural diagram by solid and broken wedges.

All the members of the genus described above exhibit biological activity in screens that are predictive of utility. However, it may be found upon examination that certain species and genera are not patentable to the inventors in this application. In this case, the exclusion of species and genera in applicants' claims are to be considered artifacts of patent prosecution and not reflective of the inventors' concept or description of their invention, which encompasses all members of the genus I that are not in the public's possession.

As used herein, and as would be understood by the person of skill in the art, the recitation of "a compound"—unless expressly further limited—is intended to include salts of that compound. In a particular embodiment, the term "compound of formula" refers to the compound or a pharmaceutically acceptable salt thereof.

The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, adipic, alginic, ascorbic, aspartic, benzenesulfonic (besylate), benzoic, boric, butyric, camphoric, camphorsulfonic, carbonic, citric, ethanedisulfonic, ethanesulfonic, ethylenediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, and the like. When the compounds contain an acidic side chain, suitable pharmaceutically acceptable base addition salts for the compounds of the present invention include, but are not limited to, metallic salts made from aluminum, calcium, lithium, magnesium, potassium, sodium and zinc or organic salts made from lysine, arginine, N,N'-dibenzylethylenediamine, chloroprocaine, choline, diethanolamine, ethylenediamine, meglumine (N-methylglucamine) and procaine. Further pharmaceutically acceptable salts include, when appropriate, nontoxic ammonium cations and carboxylate, sulfonate and phosphonate anions attached to alkyl having from 1 to 20 carbon atoms.

Also provided herein is a pharmaceutical composition comprising a compound disclosed above, or a pharmaceutically acceptable salt form thereof, and a pharmaceutically acceptable carrier or diluent.

While it may be possible for the compounds of formula I to be administered as the raw chemical, it is preferable to present them as a pharmaceutical composition. According to a further aspect, the present invention provides a pharmaceutical composition comprising a compound of formula I or a pharmaceutically acceptable salt thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association a compound of formula I or a pharmaceutically acceptable salt thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

It will be recognized that the compounds of this invention can exist in radiolabeled form, i.e., the compounds may contain one or more atoms containing an atomic mass or mass number different from the atomic mass or mass number usually found in nature. Radioisotopes of hydrogen, carbon, phosphorous, fluorine, and chlorine include $^{2}H$, $^{3}H$, $^{13}C$, $^{14}C$, $^{15}N$, $^{35}S$, $^{18}F$, and $^{36}Cl$, respectively. Compounds that contain those radioisotopes and/or other radioisotopes of other atoms are within the scope of this invention. Tritiated, i.e. $^{3}H$, and carbon-14, i.e., $^{14}C$, radioisotopes are particularly preferred for their ease in preparation and detectability. Compounds that contain isotopes $^{11}C$, $^{13}N$, $^{15}O$ and $^{18}F$ are well suited for positron emission tomography. Radiolabeled compounds of formula I of this invention and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

The compounds provided herein can be used for treating cancer in a patient, the method comprising administering to the patient a therapeutically effective amount of a compound of formula I. In some embodiments, the cancer is characterized by dysregulation of the PI3K-AKT-FOXO signaling pathway. For example, the cancer can be selected from the group consisting of: ovarian, pancreatic, renal cell, breast, prostate, lung, hepatocellular carcinoma, glioma, leukemia, lymphoma, colorectal cancers, and sarcomas.

In some embodiments, the method further comprises administering one or more additional cancer chemotherapeutic agents. In some embodiments, the one or more additional cancer chemotherapeutic agents are EGFR inhibitors. Non-limiting examples of the additional chemotherapeutic agent include erlotinib and gefitinib.

In some embodiments, the cancer is chemotherapy resistant cancer. In some embodiments, the method further comprises administering one or more cancer chemotherapeutic agents. In some embodiments, the one or more cancer chemotherapeutic agents are EGFR inhibitors. For example, the chemotherapeutic agent is erlotinib or gefitinib.

In some embodiments, administration of a compound of formula I can restore sensitivity to one or more chemotherapeutic agents in a patient wherein the patient has developed a resistance to the one or more chemotherapeutic agents. More particularly, cancers that may be treated by the compounds, compositions and methods described herein include, but are not limited to, the following:

cardiac cancers, including, for example sarcoma, e.g., angiosarcoma, fibrosarcoma, rhabdomyosarcoma, and liposarcoma; myxoma; rhabdomyoma; fibroma; lipoma and teratoma;

lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma;

gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma;

genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma;

liver cancers, including, for example, hepatoma, e.g., hepatocellular carcinoma; cholangiocarcinoma; hepatoblastoma; angio sarcoma; hepatocellular adenoma; and hemangioma;

bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors;

nervous system cancers, including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma;

gynecological cancers, including, for example, cancers of the uterus, e.g., endometrial carcinoma; cancers of the cervix, e.g., cervical carcinoma, and pre tumor cervical dysplasia; cancers of the ovaries, e.g., ovarian carcinoma, including serous cystadenocarcinoma, mucinous cystadenocarcinoma, unclassified carcinoma, granulosa thecal cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma;

hematologic cancers, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non Hodgkin's lymphoma (malignant lymphoma) and Waldenstrom's macroglobulinemia;

skin cancers, including, for example, malignant melanoma, basal cell carcinoma, squamous cell carcinoma, Kaposi's sarcoma, moles dysplastic nevi, lipoma, angioma, dermatofibroma, keloids, psoriasis; and adrenal gland cancers, including, for example, neuroblastoma.

Cancers may be solid tumors that may or may not be metastatic. Cancers may also occur, as in leukemia, as a diffuse tissue.

The compounds described herein can also be administered in combination with existing methods of treating cancers, for example by chemotherapy, irradiation, or surgery. Thus, there is further provided a method of treating cancer comprising administering an effective amount of a compound according to formula I to a patient, wherein a therapeutically effective amount of one or more additional cancer chemotherapeutic agents are administered to the patient. Examples of suitable chemotherapeutic agents include EGFR inhibitors such as erlotinib or gefitinib.

Also provided herein is a method for treating diabetes in a patient, the method comprising administering to the patient a therapeutically effective amount of a compound of formula I.

Further provided herein is a method for treating an autoimmune disease in a patient, the method comprising administering to the patient a therapeutically effective amount of a compound of formula I. The autoimmune disease can be, for example, inflammatory bowel disease (IBD). Immune responses are constantly and tightly regulated and one important cellular component in maintaining self tolerance (i.e., prevention of autoimmunity) and tolerance of benign commensal gut flora are regulatory T cells (Treg). Treg can be subdivided into multiple phenotypes, but the most common are CD4+CD25+ T cells that express the transcription factor Foxp3. Foxp3 is a direct transcriptional target of FOXO proteins, particularly FOXO1 and FOXO3. Thus activation of FOXO proteins in naïve T-cells promotes and directs differentiation to maintain a population of Treg cells.

Acute immune mediated rejection and chronic immune mediated rejection are key obstacles to successful solid organ transplantation. It is believed that these forms of rejection can be prevented/overcome by amplifying Treg number and or function. Similarly, a common and morbid complication of allogeneic hematopoietic cell transplants (Allo-HCT) used to treat various malignant and non-malignant conditions, is graft versus host disease, in which the transplanted immune cells from the donor damage multiple organs in the recipient (most notably skin, gut, and liver). Increasing experimental and clinical data indicate that Tregs can be harnessed to prevent and or treat this disease process.

Thus compounds of the present invention are useful in treatment of autoimmune and related diseases, by activating FOXO proteins and inducing T cell differentiation to Tregs. Compounds may be administered therapeutically to subjects directly, or alternatively, T cells may be collected from a subject and differentiated ex vivo to Tregs as described by Taylor et al. [*Blood* 99, 3493-3499 (2002)]. Compounds of the present invention may be used alone or in combination with conventional immunosuppressive drugs such as cyclosporine, FK506 or rapamycin and its analogs. In addition compounds of the present invention may be co-administered with histone deacetylase inhibitors (HDACi) which have been shown to enhance Treg function by maintaining Foxp3 acetylation and activity.

Aspects of the invention include methods for treatment of autoimmune disease characterized by deficiency in Treg function comprising administering a therapeutically useful amount of compound of Formula I, optionally in combination with an HDAC inhibitor. The method can also include extraction of naïve T-cells from a patient, differentiation of T-cells to Tregs ex vivo by treatment with a compound of Formula I, optionally supplemented with an HDACi, followed by administration of Tregs to patient with optional separation of compound of Formula I from Tregs prior to their administration. As stated above, autoimmune diseases that can be so treated include IBD, solid organ transplant rejection, and GvHD in allo-HCT In some embodiments, the compounds can be administered to a patient to treat an autoimmune disorder, for example, Addison's disease, Amyotrophic Lateral Sclerosis, celiac disease, Crohn's disease, diabetes, eosinophilic fasciitis, Guillain-Barré syndrome (GBS), Graves' disease, Lupus erythematosus, Miller-Fisher syndrome, psoriasis, rheumatoid arthritis, ulcerative colitis, and vasculitis. In some embodiments, the compound provided herein can be used for treating a disease or disorder in a patient wherein the disease or disorder involves excessive or unregulated cellular proliferation, the method comprising administering to the patient a therapeutically effective amount of a compound of formula (I). Also provided herein is a method for treating a disease or disorder in a patient where the disease or disorder involves the dysregulation of the pi3K-AKT-FOXO signaling pathway, the method comprising administering to the patient a therapeutically effective amount of a compound of formula I.

Further provided herein is a method for treating a disease in a patient wherein the disease is characterized by proteotoxicity, including age onset proteotoxicity leading to neurodegeneration, the method comprising administering to the patient a therapeutically effective amount of a compound of formula I. Hyperphosphorylated Tau has been implicated as the pathogenic protein in several neurodegenerative diseases and furthermore PP2A has been shown to be an important phosphatase in reversing aberrant phosphorylation of Tau; see for example Ludovic Martin et al., Tau protein phosphatases in Alzheimer's disease: The leading role of PP2A in Ageing Research Reviews 12 (2013) 39-49; Miguel Medina and Jesus Avila, Further understanding of tau phosphorylation: implications for therapy in Expert Rev. Neurotherapy, 15(1), 115-112 (2015) and Michael Voronkov et al., Phosphoprotein phosphatase 2A: a novel druggable target for Alzheimer's disease in Future Med Chem. 2011 May, 3(7) 821-833. Hyperphosphorylated alpha-Synuclein is a second exemplar of a toxic protein, and again PP2A has been shown to reverse its aberrantly phosphorylated state; see for example Kang-Woo Lee et al., Enhanced Phosphatase Activity Attenuates alpha-Synucleinopathy in a Mouse Model in Neurobiology of Disease, May 11, 2011, 31(19) 6963-6971. In some embodiments, the disease is selected from the group consisting of: Alzheimer's disease, Parkinson's disease, Huntington's disease, amyotrophic lateral sclerosis, frontotemporal dementia, progressive supranuclear palsy, corticobasal degeneration and Pick's disease.

The compounds provided herein may further be used in a method for treating a mood disorder in a patient by administering to the patient a therapeutically effective amount of a compound of formula I. In some embodiments, the mood disorder is stress-induced depression.

Also provided herein is a method for treating acne vulgaris in a patient by administering to the patient a therapeutically effective amount of a compound of formula I.

Further provided herein is a method for treating cardiac hypertrophy in a patient by administering to the patient a therapeutically effective amount of a compound of formula I. In some embodiments, the cardiac hypertrophy is associated with a disease selected from hypertension, myocardial infarction, and valvular heart disease.

The compounds provided herein may further be used in a method for treating a viral infection in a patient by administering to the patient a therapeutically effective amount of a compound of formula I. Examples of viruses that may cause viral infections to be treated include, but are not limited to: a polyomavirus, such as John Cunningham Virus (JCV), Simian virus 40 (SV40), or BK Virus (BKV); influenza, Human Immunodeficiency Virus type 1 (HIV-1), Human Papilloma Virus (HPV), adenovirus, Epstein-Barr Virus (EBV), Hepatitis C Virus (HCV), Molluscum contagiosum virus (MCV); Human T-lymphotropic virus type 1 HTLV-1), Herpes Simplex Virus type 1 (HSV-1), cytomegalovirus (CMV), hepatitis B virus, Bovine papillomavirus (BPV-1), human T-cell lymphotropic virus type 1, Japanese encephalitis virus, respiratory syncytial virus (RSV), and West Nile virus.

Further provided herein is a method for treating a parasitic infection in a patient by administering to the patient a therapeutically effective amount of a compound of formula I. Examples of parasites that may cause parasitic infections to be treated include, but are not limited to, *Plasmodium* and *Theileria*.

PP2A enzymes are involved in the regulation of cell transcription, cell cycle, and viral transformation. Many viruses, including cytomegalovirus, parainfluenza, DNA tumor viruses, and HIV-1, utilize different approaches to exploit PPA2 in order to modify, control, or inactivate cellular activities of the host [Garcia et al., Microbes and Infection, 2, 2000, 401-407]. Therefore, the compounds provided herein may further be used in a method for treating a viral infection in a patient by administering to the patient a therapeutically effective amount of a compound of formula (I). Examples of viruses that may cause viral infections to be treated include, but are not limited to: a polyomavirus, such as John Cunningham Virus (JCV), Simian virus 40 (SV40), or BK Virus (BKV); influenza, Human Immunodeficiency Virus type 1 (HIV-1), Human Papilloma Virus (HPV), adenovirus, Epstein-Barr Virus (EBV), Hepatitis C Virus (HCV), Molluscum contagiosum virus (MCV); Human T-lymphotropic virus type 1 HTLV-1), Herpes Simplex Virus type 1 (HSV-1), cytomegalovirus (CMV), hepatitis B virus, Bovine papillomavirus (BPV-1), human T-cell lymphotropic virus type 1, Japanese encephalitis virus, respiratory syncytial virus (RSV), and West Nile virus.

Serine/Threonine phosphatases, including PP2A are involved in modulation of synaptic plasticity (D. G. Winder and J. D. Sweatt, Nature Reviews Neuroscience, vol 2, July 2001, pages 461-474). Persistently decreased PP2A activity is associated with maintenance of Long Term Potentiation (LTP) of synapses, thus treatment PP2A activators such as those described here may reverse synaptic LTP. Psychostimulant drugs of abuse such as cocaine and methamphetamine are associated with deleterious synaptic LTP (L. Mao et al, Neuron 67, Sep. 9, 2010 and A. Stipanovich et al, Nature vol 453, 2008, pages 879-884), which may underlie the pathology of addiction and relapse therefore PP2A activators described here may be useful as treatments for psychostimulant abuse.

Abnormalities in synaptic structure and signaling are linked to autistic spectrum disorder, see for example, Y Chen et al., CTTNBP2, but not CTTNBP2NL, regulates dendritic spinogenesis and synaptic distribution of the striatin—PP2A complex, Molecular Biology of the Cell, 23, Nov. 15, 2012, 4383-4392. PP2A has been shown to be important in normal development of dendritic spines, and treatment with compounds of the present invention may ameliorate or reverse autistic spectrum disorder.

Unless defined otherwise, all technical and scientific terms used herein have the same meaning as is commonly understood by one of ordinary skill in the art to which this disclosure belongs. A comprehensive list of abbreviations utilized by organic chemists (i.e. persons of ordinary skill in the art) appears in the first issue of each volume of the *Journal of Organic Chemistry*. The list, which is typically presented in a table entitled "Standard List of Abbreviations" is incorporated herein by reference. In the event that there is a plurality of definitions for terms cited herein, those in this section prevail unless otherwise stated.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof, but only if the additional features, integers, steps, components or groups thereof do not materially alter the basic and novel characteristics of the claimed composition or method.

A "patient," as used herein, includes both humans and other animals, particularly mammals. Thus the methods are applicable to both human therapy and veterinary applications. In some embodiments, the patient is a mammal, for example, a primate. In some embodiments, the patient is a human.

Treatment can involve administering a compound described herein to a patient diagnosed with a disease, and may involve administering the compound to a patient who does not have active symptoms. Conversely, treatment may involve administering the compositions to a patient at risk of developing a particular disease, or to a patient reporting one or more of the physiological symptoms of a disease, even though a diagnosis of this disease may not have been made.

The terms "administer", "administering" or "administration" in reference to a dosage form of the invention refers to the act of introducing the dosage form into the system of subject in need of treatment. When a dosage form of the invention is given in combination with one or more other active agents (in their respective dosage forms), "administration" and its variants are each understood to include concurrent and/or sequential introduction of the dosage form and the other active agents. Administration of any of the described dosage forms includes parallel administration, co-administration or sequential administration. In some situations, the therapies are administered at approximately the same time, e.g., within about a few seconds to a few hours of one another.

A "therapeutically effective" amount of the compounds described herein is typically one which is sufficient to achieve the desired effect and may vary according to the nature and severity of the disease condition, and the potency of the compound. It will be appreciated that different concentrations may be employed for prophylaxis than for treatment of an active disease. A therapeutic benefit is achieved with the amelioration of one or more of the physiological symptoms associated with the underlying disorder such that an improvement is observed in the patient, notwithstanding that the patient may still be afflicted with the underlying disorder.

The term "modulate" with respect to a FOXO transcription factor protein refers to activation of the FOXO transcription factor protein and its biological activities associated with the FOXO pathway. Modulation of FOXO transcription factor proteins includes up-regulation (i.e., agonizing, activation or stimulation). The mode of action of a FOXO modulator can be direct, e.g., through binding to the FOXO transcription factor protein as a ligand. The modulation can also be indirect, e.g., through binding to and/or modifying another molecule which otherwise binds to and activates the FOXO transcription factor protein.

Throughout this specification the terms and substituents retain their definitions.

$C_1$ to $C_{20}$ hydrocarbon includes alkyl, cycloalkyl, polycycloalkyl, alkenyl, alkynyl, aryl and combinations thereof. Examples include benzyl, phenethyl, cyclohexylmethyl, adamantyl, camphoryl and naphthylethyl. Hydrocarbyl refers to any substituent comprised of hydrogen and carbon as the only elemental constituents. Aliphatic hydrocarbons are hydrocarbons that are not aromatic; they may be saturated or unsaturated, cyclic, linear or branched. Examples of aliphatic hydrocarbons include isopropyl, 2-butenyl, 2-butynyl, cyclopentyl, norbornyl, etc. Aromatic hydrocarbons include benzene (phenyl), naphthalene (naphthyl), anthracene, etc.

Unless otherwise specified, alkyl (or alkylene) is intended to include linear or branched saturated hydrocarbon structures and combinations thereof. Alkyl refers to alkyl groups from 1 to 20 carbon atoms, preferably 1 to 10 carbon atoms, more preferably 1 to 6 carbon atoms. Examples of alkyl groups include methyl, ethyl, propyl, isopropyl, n-butyl, s-butyl, t-butyl and the like.

Cycloalkyl is a subset of hydrocarbon and includes cyclic hydrocarbon groups of from 3 to 8 carbon atoms. Examples of cycloalkyl groups include cy-propyl, cy-butyl, cy-pentyl, norbornyl and the like.

Unless otherwise specified, the term "carbocycle" is intended to include ring systems in which the ring atoms are all carbon but of any oxidation state. Thus ($C_3$-$C_{10}$) carbocycle refers to both non-aromatic and aromatic systems, including such systems as cyclopropane, benzene and cyclohexene; ($C_8$-$C_{12}$) carbopolycycle refers to such systems as norbornane, decalin, indane and naphthalene. Carbocycle, if not otherwise limited, refers to monocycles, bicycles and polycycles.

Heterocycle means an aliphatic or aromatic carbocycle residue in which from one to four carbons is replaced by a heteroatom selected from the group consisting of N, O, and S. The nitrogen and sulfur heteroatoms may optionally be oxidized, and the nitrogen heteroatom may optionally be quaternized. Unless otherwise specified, a heterocycle may be non-aromatic (heteroaliphatic) or aromatic (heteroaryl). Examples of heterocycles include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a sub stituent), tetrazole, morpholine, thiazole, pyridine, pyridazine, pyrimidine, thiophene, furan, oxazole, oxazoline, isoxazole, dioxane, tetrahydrofuran and the like. Examples of heterocyclyl residues include piperazinyl, piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl (also historically called thiophenyl), benzothienyl, thiamorpholinyl, oxadiazolyl, triazolyl and tetrahydroquinolinyl.

Alkoxy or alkoxyl refers to groups of from 1 to 20 carbon atoms, preferably 1 to 10 carbon atoms, more preferably 1 to 6 carbon atoms of a straight or branched configuration attached to the parent structure through an oxygen. Examples include methoxy, ethoxy, propoxy, isopropoxy and the like. Lower-alkoxy refers to groups containing one to four carbons. For the purpose of this application, alkoxy and lower alkoxy include methylenedioxy and ethylenedioxy.

The term "halogen" means fluorine, chlorine, bromine or iodine atoms. In one embodiment, halogen may be a fluorine or chlorine atom.

Unless otherwise specified, acyl refers to formyl and to groups of 1, 2, 3, 4, 5, 6, 7 and 8 carbon atoms of a straight, branched, cyclic configuration, saturated, unsaturated and aromatic and combinations thereof, attached to the parent structure through a carbonyl functionality. Examples include acetyl, benzoyl, propionyl, isobutyryl and the like. Lower-acyl refers to groups containing one to four carbons. The double bonded oxygen, when referred to as a substituent itself is called "oxo".

As used herein, the term "optionally substituted" may be used interchangeably with "unsubstituted or substituted". The term "substituted" refers to the replacement of one or more hydrogen atoms in a specified group with a specified radical. For example, substituted alkyl, aryl, cycloalkyl, heterocyclyl etc. refer to alkyl, aryl, cycloalkyl, or heterocyclyl wherein one or more H atoms in each residue are replaced with halogen, haloalkyl, alkyl, acyl, alkoxyalkyl, hydroxy lower alkyl, carbonyl, phenyl, heteroaryl, benzenesulfonyl, hydroxy, lower alkoxy, haloalkoxy, oxaalkyl, carboxy, alkoxycarbonyl [—C(=O)O-alkyl], alkoxycarbonylamino [HNC(=O)O-alkyl], aminocarbonyl (also known as carboxamido) [—C(=O)NH$_2$], alkylaminocarbonyl [—C(=O)NH-alkyl], cyano, acetoxy, nitro, amino, alkylamino, dialkylamino, (alkyl)(aryl)aminoalkyl, alkylaminoalkyl (including cycloalkylaminoalkyl), dialkylaminoalkyl, dialkylaminoalkoxy, heterocyclylalkoxy, mercapto, alkylthio, sulfoxide, sulfone, sulfonylamino, alkylsulfinyl, alkylsulfonyl, acylaminoalkyl, acylaminoalkoxy, acylamino, amidino, aryl, benzyl, heterocyclyl, heterocyclylalkyl, phenoxy, benzyloxy, heteroaryloxy, hydroxyimino, alkoxyimino, oxaalkyl, aminosulfonyl, trityl, amidino, guanidino, ureido, benzyloxyphenyl, and benzyloxy. "Oxo" is also included among the substituents referred to in "optionally substituted"; it will be appreciated by persons of skill in the art that, because oxo is a divalent radical, there are circumstances in which it will not be appropriate as a substituent (e.g. on phenyl). In one embodiment, 1, 2, or 3 hydrogen atoms are replaced with a specified radical. In the case of alkyl and cycloalkyl, more than three hydrogen atoms can be replaced by fluorine; indeed, all available hydrogen atoms could be replaced by fluorine. In preferred embodiments, substituents are halogen, haloalkyl, alkyl, acyl, hydroxyalkyl, hydroxy, alkoxy, haloalkoxy, aminocarbonyl oxaalkyl, carboxy, cyano, acetoxy, nitro, amino, alkylamino, dialkylamino, alkylthio, alkylsulfinyl, alkylsulfonyl, alkylsulfonylamino arylsulfonyl, arylsulfonylamino, and benzyloxy.

Substituents R″ are generally defined when introduced and retain that definition throughout the specification and in all independent claims.

EXAMPLES

| Example No. | Structure | H1650 GI50 | Notes |
|---|---|---|---|
| 1 | (phenoxazine-N-cyclohexane with OH and NHSO₂-C₆H₄-OCF₃) | 5 uM | Racemic Single diastereoisomer |
| 1a | (phenoxazine-N-cyclohexane with OH and NHSO₂-C₆H₄-OCF₃) | 5 uM | Peak 1 of chromatographic resolution $[\alpha]_D = +19$ (c = 1.0 MeOH) 1R,2R,3S absolute sterochemistry |
| 1b | (phenoxazine-N-cyclohexane with OH and NHSO₂-C₆H₄-OCF₃) | 5 uM | Peak 2 of chromatographic resolution $[\alpha]_D = -23$ (c = 1.0 MeOH) 1S,2S,3R absolute sterochemistry |
| 2 | (dibenzoxazepine-N-cyclohexane with OH and NHSO₂-C₆H₄-OCF₃) | 20 uM | Racemic |
| 3 | (carbazole-N-cyclohexane with OH and NHSO₂-C₆H₄-OCF₃) | 10 uM | Racemic. Single diastereoisomer |

-continued

| Example No. | Structure | H1650 GI50 | Notes |
|---|---|---|---|
| 3a | (carbazole-cyclohexane-OH-NHSO2-C6H4-OCF3) | 10 uM | Peak 1 of chromatographic resolution 1R,2R,3S absolute sterochemistry |
| 3b | (carbazole-cyclohexane-OH-NHSO2-C6H4-OCF3) | 10 um | Peak 2 of chromatographic resolution 1S,2S,3R absolute sterochemistry |
| 4 | (carbazole-cyclohexane-OH-NHSO2-C6H4-Cl) | 15 uM | |
| 5 | (carbazole-cyclohexane-OH-NHSO2-C6H4-CN) | 20 uM | |
| 6 | (carbazole-cyclohexane-OH-NHSO2-C6H4-OMe) | 20 uM | |

-continued
| Example No. | Structure | H1650 GI50 | Notes |
|---|---|---|---|
| 7 | 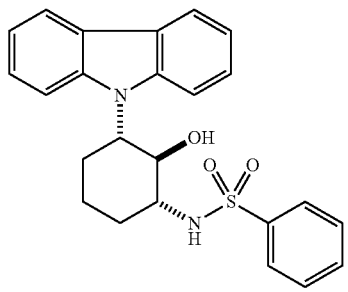 | 25 uM | |
| 8 | 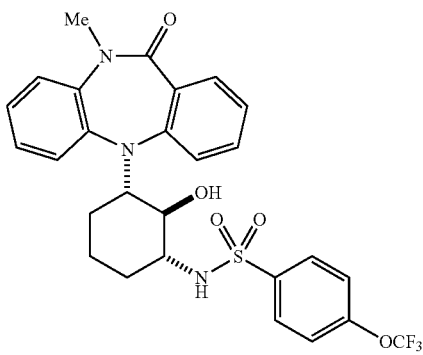 | 15 uM | |
| 9 | 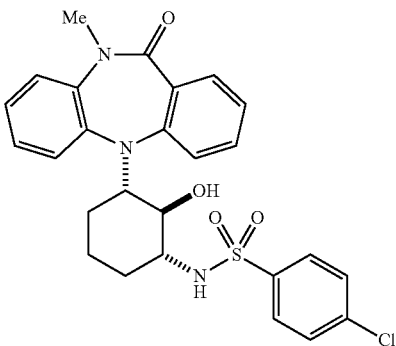 | 25 um | |
| 10 | 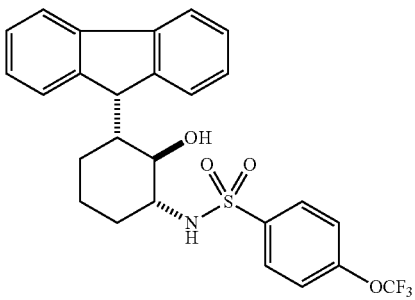 | | |

-continued

| Example No. | Structure | H1650 GI50 | Notes |
|---|---|---|---|
| 12 | 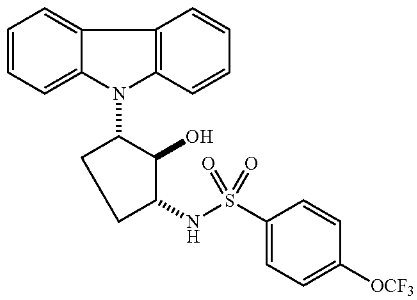 | | |
| 13 | 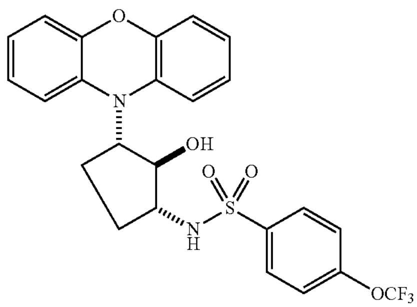 | | |
| 14 | 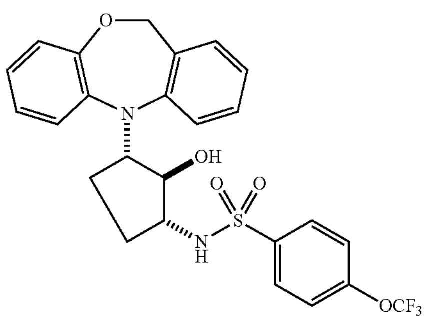 | | |
| 15 | 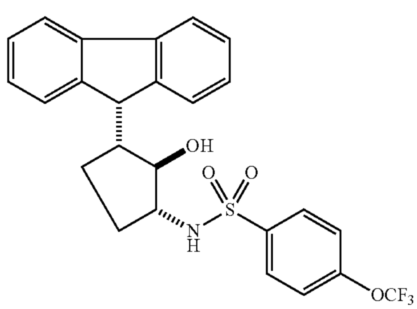 | | |
| 16 | 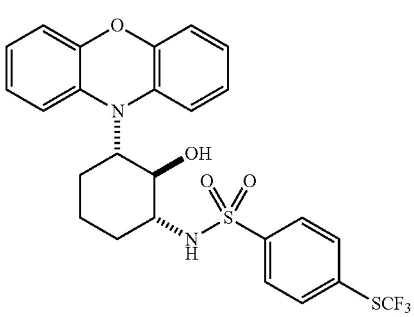 | 10 uM | Racemic |

-continued

| Example No. | Structure | H1650 GI50 | Notes |
|---|---|---|---|
| 17 | phenoxazine-cyclohexane(OH)-NHSO2-(2-Cl,4-OCF3-phenyl) | 15 uM | Racemic |
| 18 | phenoxazine-cyclohexane(OH)-NHSO2-(4-CH2CF3-phenyl) | 15 uM | Racemic |
| 19 | phenoxazine-cyclohexane(OH)-NHSO2-(4-CF2CF3-phenyl) | 10 uM | Racemic |
| 20 | phenoxazine-cyclohexane(OH)-NHSO2-(4-OCHF2-phenyl) | 25 uM | Racemic |
| 21 | phenoxazine-cyclohexane(OH)-NHSO2-(3-Cl,4-OCF3-phenyl) | 15 uM | Racemic |

-continued

| Example No. | Structure | H1650 GI50 | Notes |
|---|---|---|---|
| 22 | 3,6-dichlorocarbazole-N-cyclohexyl-OH-NHSO2-C6H4-OCF3 | 5 uM | Racemic |
| 23 | 3,6-dichlorocarbazole-N-cyclohexyl-OH-NHSO2-C6H4-Cl | 5 uM | Racemic |
| 24 | 3,6-dibromocarbazole-N-cyclohexyl-OH-NHSO2-C6H4-OCF3 | 5 uM | Racemic |
| 25 | 3,6-dibromocarbazole-N-cyclohexyl-OH-NHSO2-C6H4-Cl | 15 uM | Racemic |
| 26 | 3,6-dicyanocarbazole-N-cyclohexyl-OH-NHSO2-C6H4-OCF3 | Weak | Racemic |

| Example No. | Structure | H1650 GI50 | Notes |
|---|---|---|---|
| 27 | 3-Br, 6-CN carbazole with N-cyclohexyl(OH, NHSO2-C6H4-OCF3) | 5 uM | Racemic |
| 28 | 3-CN carbazole with N-cyclohexyl(OH, NHSO2-C6H4-OCF3) | 10 uM | Racemic |
| 29 | 3-CO2Me carbazole with N-cyclohexyl(OH, NHSO2-C6H4-OCF3) | 15 uM | Racemic |
| 30 | 3-Br carbazole with N-cyclohexyl(OH, NHSO2-C6H4-OCF3) | 5 uM | Racemic |
| 31a | 3-F carbazole with N-cyclohexyl(OH, NHSO2-C6H4-OCF3) | 5 uM | Chiral 1S,2S,3R |

-continued

| Example No. | Structure | H1650 GI50 | Notes |
|---|---|---|---|
| 31b | 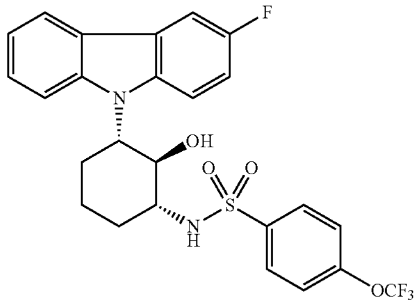 | 5 uM | Chiral 1R,2R,3S |
| 32a | 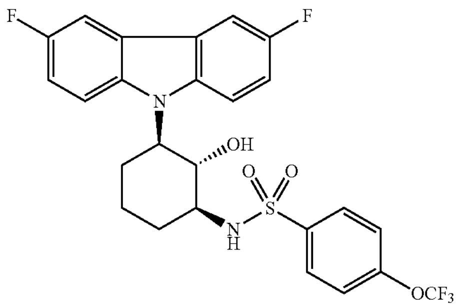 [SMILES: O=S(=O)(N[C@H]1CCC[C@@H](n2c3ccc(F)cc3c3cc(F)ccc32)[C@@H]1O)c1ccc(OC(F)(F)F)cc1] | 5 uM | Chiral 1S,2S,3R |
| 32b | 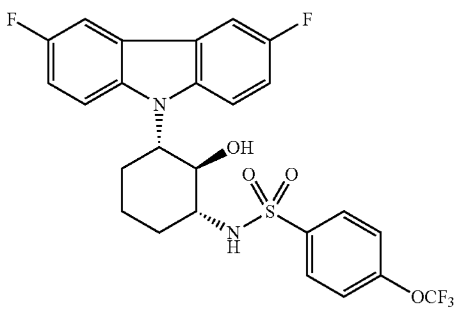 [SMILES: O=S(=O)(N[C@@H]1CCC[C@H](n2c3ccc(F)cc3c3cc(F)ccc32)[C@H]1O)c1ccc(OC(F)(F)F)cc1] | 5 uM | Chiral 1R,2R,3S |
| 34 | 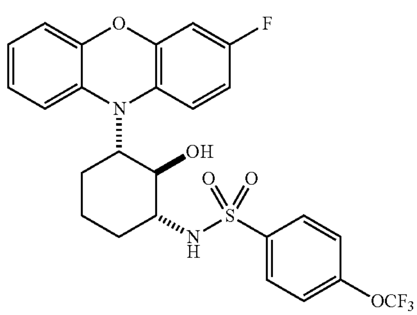 | | |
| 35 | 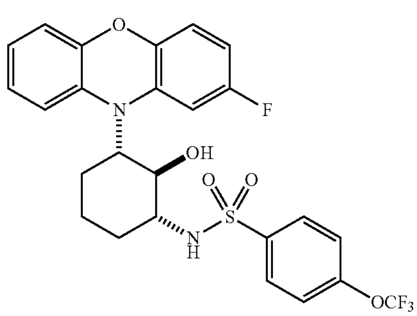 | | |

-continued
| Example No. | Structure | H1650 GI50 | Notes |
|---|---|---|---|
| 36 | 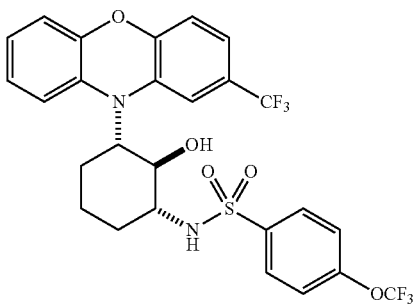 | | |
| 37 | 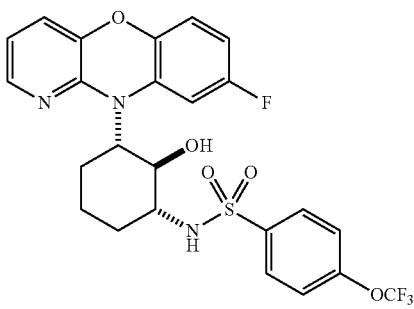 | | |
| 38 | 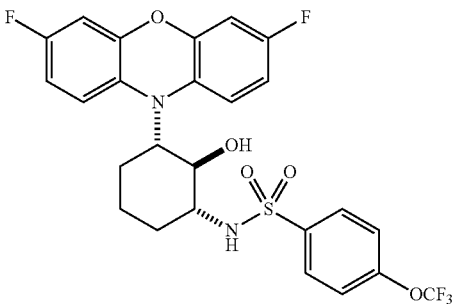 | | |
| 39 | 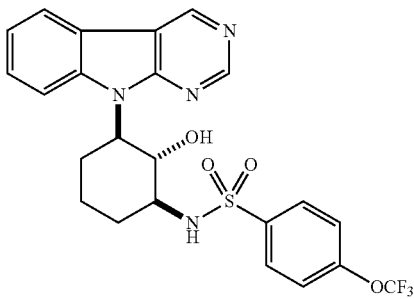 | | |

| Example No. | Structure | H1650 GI50 | Notes |
|---|---|---|---|
| 40 | 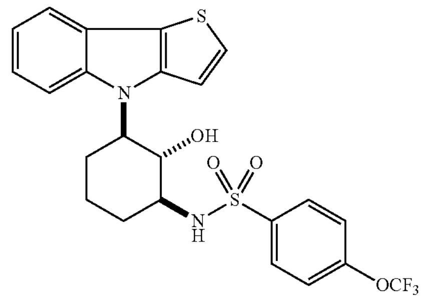 | | |
| 41 | 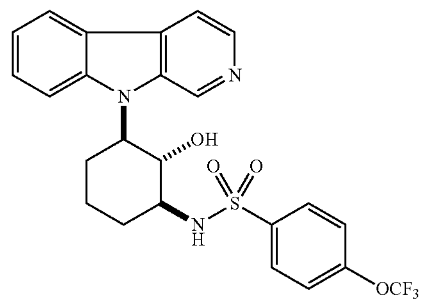 | | |

Preparation of compounds can involve the protection and deprotection of various chemical groups. The need for protection and deprotection, and the selection of appropriate protecting groups, can be readily determined by one skilled in the art. Suitable groups for that purpose are discussed in standard textbooks in the field of chemistry, such as *Protective Groups in Organic Synthesis* by T. W. Greene and P. G. M. Wuts [John Wiley & Sons, New York, 1999], in *Protecting Group Chemistry*, 1st Ed., Oxford University Press, 2000; and in *March's Advanced Organic chemistry: Reactions, Mechanisms, and Structure*, 5th Ed., Wiley-Interscience Publication, 2001.

In general, compounds of formula I can be prepared as shown in Schemes 1, 2 and 3. The first step is attachment of the tricycle to the cycloalkene that will become the amino cycloalkanol. When A is N, the first step is as follows:

Scheme 1

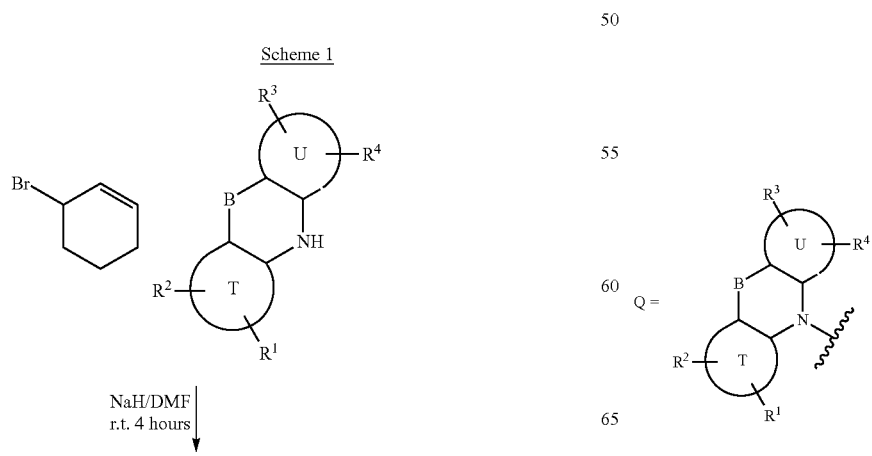

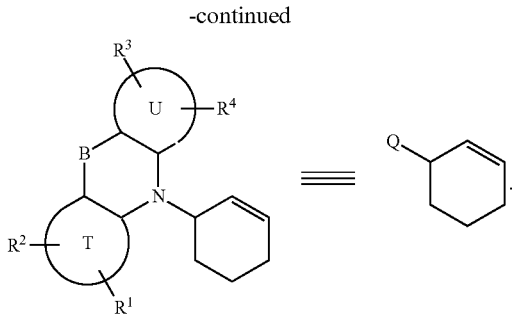

When A is CH, the first step is as follows:
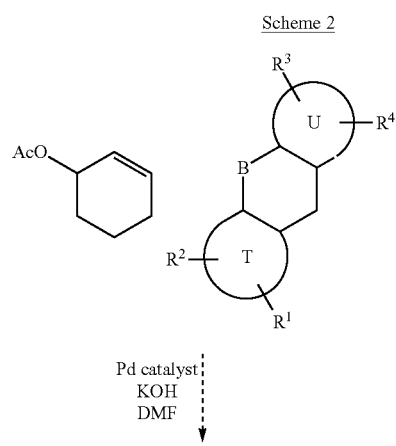
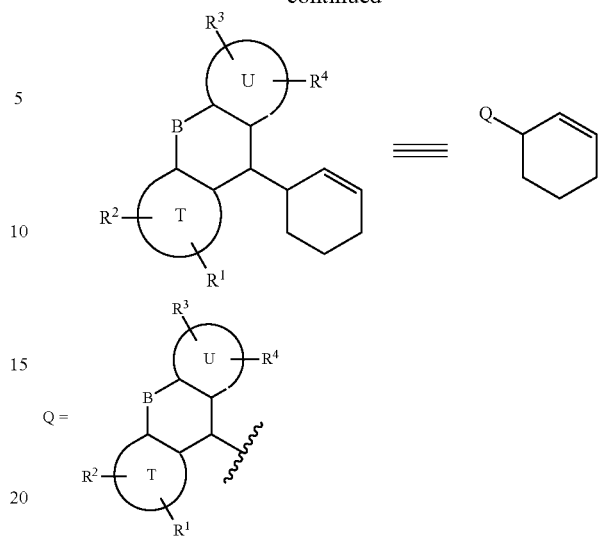
The remaining steps are the same:
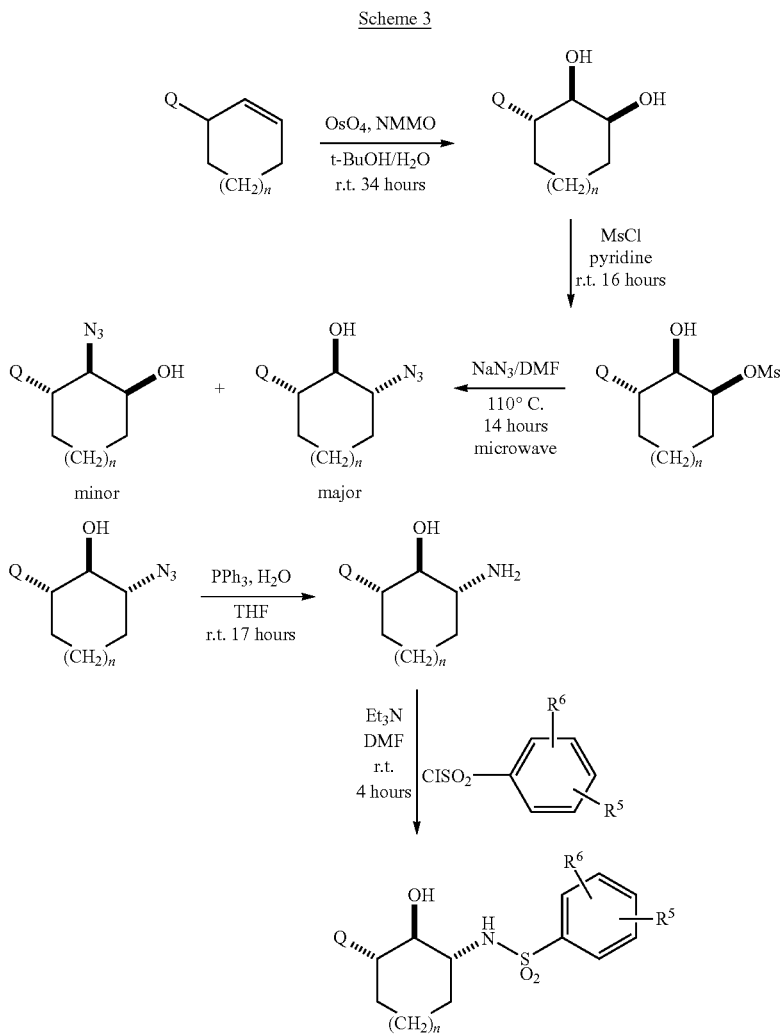

The foregoing scheme produces sulfonamide products of the (1S,2S,3R)-rel configuration. When products of other relative configurations are desired, the cycloalkene may be oxidized with reagents, such as meta-chloroperbenzoic acid and others well-known to persons of skill in the art, and the resulting epoxide opened in a trans sense.

Exemplary syntheses are presented below:

Example 1

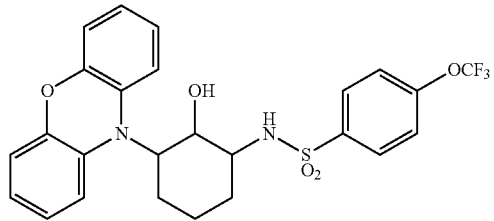

1

The synthesis begins with alkylation of commercially available 10H-phenoxazine with commercially available 3-bromocyclohex-1-ene to afford 10-(cyclohex-2-en-1-yl)-10H-phenoxazine in 77% yield. An osmium tetroxide catalyzed dihydroxylation afforded diol in 44% yield. Treatment of diol with methanesulfonyl choride furnished mesylate in 48% yield. A sodium azide-induced azide displacement afforded crude azide, which was taken to the next step without further purification. Amine was synthesized from azide via a Staudinger reaction; the overall yield of amine from mesylate was 8%. Treating the amine with commercially available 4-(trifluoromethoxy)benzene-1-sulfonyl chloride afforded target sulfonamide Example 1 in a yield of 42%.

10-(cyclohex-2-en-1-yl)-10H-phenoxazine. To a solution of 10H-phenoxazine (2.00 g, 10.9 mmol) in DMF (11 mL) at RT, was added NaH (0.480 g, 11.9 mmol, 60% dispersion in mineral oil). The mixture was stirred at RT for 1 h. 3-bromocyclohex-1-ene (3.51 g, 21.8 mmol) was added to the above solution, and the reaction mixture was stirred at RT for 3 h, neutralized with sat. aq. NH$_4$Cl, extracted with dichloromethane, concentrated in vacuo to give a residue which was purified by flash chromatography (SiO$_2$, 100% hexanes) to afford 10-(cyclohex-2-en-1-yl)-10H-phenoxazine (2.21 g, 77%). $^1$H NMR (600 MHz, CDCl$_3$) δ 6.84-6.71 (7H, m), 5.94-5.92 (1H, m), 5.94-5.92 (1H, m), 5.84-5.82 (1H, m), 4.58 (1H, bs), 2.23-2.15 (3H, m), 2.07-1.99 (2H, m), 1.84-1.77 (1H, m); $^{13}$C NMR (150 MHz, CDCl$_3$) δ 147.4, 134.8, 130.1, 129.8, 123.5, 121.2, 115.8, 114.4, 55.3, 24.8, 24.6, 22.4; LCMS m/z 264.1354 ([M+H$^+$], C$_{18}$H$_{18}$NO requires 264.3411).

3-(10H-phenoxazin-10-yl)cyclohexane-1,2-diol. A solution of 10-(cyclohex-2-en-1-yl)-10H-phenoxazine (2.21 g, 8.39 mmol), 4-methylmorpholine N-oxide (0.098 g, 0.838 mmol), and osmium tetroxide (0.080 mL, 0.008 mmol, 2.5% in tert-butanol) in tert-butanol (11.6 mL) and water (2.3 mL), was stirred at RT for 12 h. The reaction mixture was treated with sat. aq. sodium bisulfite solution, extracted with dichloromethane, concentrated, and purified by flash chromatography (SiO$_2$, 0%-70% ethyl acetate-hexanes) to afford 3-(10H-phenoxazin-10-yl)cyclohexane-1,2-diol (1.09 g, 44%). $^1$H NMR (600 MHz, DMSO-d$^6$) δ 6.96-6.94 (2H, m), 6.86-6.84 (2H, m), 6.73-6.69 (4H, m), 4.76 (1H, d, J=5.4 Hz), 4.52 (1H, d, J=2.4 Hz), 4.00-3.95 (2H, m), 3.92-3.87 (1H, m), 1.96-1.89 (1H, m), 1.83-1.81 (1H, m), 1.72-1.66 (2H, m), 1.51-1.43 (2H, m); $^{13}$C NMR (150 MHz, DMSO-d$^6$) δ 148.2, 136.1, 124.2, 121.9, 117.4, 115.7, 71.3, 70.5, 62.0, 31.4, 29.4, 19.7; LCMS m/z 298.2582 ([M+H$^+$], C$_{18}$H$_{20}$NO$_3$ requires 298.3558).

2-hydroxy-3-(10H-phenoxazin-10-yl)cyclohexyl methanesulfonate. To a solution of 3-(10H-phenoxazin-10-yl)cyclohexane-1,2-diol (1.09 g, 3.67 mmol) in pyridine (2.8 mL) under argon, at 0° C., was added methane sulfonyl chloride. The mixture was stirred for 2.5 h at RT. 1 N HCl was added to the reaction mixture, and extracted with DCM. Organic layer was washed with brine, concentrated, to obtain a residue which was purified by flash chromatography (SiO$_2$, 75%-100% dichloromethane-hexanes) to afford 2-hydroxy-3-(10H-phenoxazin-10-yl)cyclohexyl methanesulfonate (0.668 g, 48%). $^1$H NMR (600 MHz, CDCl$_3$) δ 6.93-6.80 (8H, m), 5.15 (1H, d, J=10.8 Hz), 4.51 (1H, bs), 4.23 (1H, bs), 3.18 (1H, s), 2.88 (3H, s), 2.13-1.82 (4H, m), 1.62-1.55 (2H, m); $^{13}$C NMR (150 MHz, CDCl$_3$) δ 149.1, 134.9, 124.1, 123.2, 117.7, 116.3, 84.0 81.7, 70.0, 61.3, 38.9, 30.6, 18.7; LCMS m/z 376.2399 ([M+H$^+$], C$_{19}$H$_{22}$NO$_5$S requires 376.4461).

2-amino-6-(10H-phenoxazin-10-yl)cyclohexanol. A solution of 2-hydroxy-3-(10H-phenoxazin-10-yl)cyclohexyl methanesulfonate (0.417 g, 1.11 mmol) in DMF (2 mL) was treated with sodium azide (0.144 g, 2.22 mmol). The mixture was heated at 110° C. for 28 h in a Biotage Initiator® microwave reactor, sat. aq. ammonium chloride was added, mixture was extracted in dichloromethane, and concentrated in vacuo. The residue obtained was purified by flash chromatography (SiO$_2$, 10%-50% ethylacetate-hexanes) to afford crude 2-azido-6-(10H-phenoxazin-10-yl)cyclohexanol (0.112 g, 31%) which was taken to the next step without further purification.

A solution of 2-azido-6-(10H-phenoxazin-10-yl)cyclohexanol (0.127 g) in THF (1.4 mL) was cooled to 0° C., treated with PPh$_3$ (0.114 g, 0.433 mmol), H$_2$O (0.043 g, 2.36 mmol), and stirred for 17 h at RT. The solution was concentrated to dryness, dissolved in a minimal amount of CH$_2$Cl$_2$ and purified by flash chromatography (SiO$_2$, 100% hexanes, 50% ethyl acetate-hexanes, 5%, methanol-dichlormethane, 17:2:1 dichloromethane:methanol:35% ammonium hydroxide) to afford (2-amino-6-(10H-phenoxazin-10-yl)cyclohexanol (0.029 g, 8% over two steps). $^1$H NMR (600 MHz, CDCl$_3$) δ 6.99-6.77 (8H, m), 4.67 (1H, m), 3.66 (1H, t, J=18.6 Hz), 3.36-3.32 (1H, m), 2.94-2.70 (3H, m), 1.95-1.93 (1H, m), 1.82-1.80 (1H, m), 1.72-1.65 (2H, m), 1.36-1.27 (1H, m), 1.21-1.15 (1H, m); $^{13}$C NMR (150 MHz, CDCl$_3$) δ 150.0, 135.0, 123.8, 123.5, 119.7, 116.2, 74.8, 70.5, 56.2, 33.1, 28.1, 23.0; LCMS m/z 297.2937 ([M+H$^+$], C$_{18}$H$_{21}$N$_2$O$_2$ requires 297.3710).

N-(2-hydroxy-3-(10H-phenoxazin-10-yl)cyclohexyl)-4-(trifluoromethoxy)-benzenesulfonamide. A solution of 2-amino-6-(10H-phenoxazin-10-yl)cyclohexanol (0.029 g, 0.098 mmol) in DMF (0.5 mL) was cooled to 0° C., treated with Et$_3$N (0.055 mL, 0.392 mmol), and 4-(trifluoromethoxy)benzene-1-sulfonyl chloride (0.018 g, 0.108 mmol). The mixture was warmed to RT, and stirred for 17 h. The mixture was partitioned between water (10 mL) and CH$_2$Cl$_2$ (10 mL). The organic layer was washed with saturated aqueous NaCl (30 mL×5) to remove DMF, and concentrated in vacuo. The residue was dissolved in a minimal amount of CH$_2$Cl$_2$ and purified by flash chromatography (SiO$_2$, 0%-50% ethylacetate-hexanes) to afford N-(2-hydroxy-3-(10H-phenoxazin-10-yl)cyclohexyl)-4-(trifluoromethoxy)benzenesulfonamide Example 1 (0.021 g, 42%). $^1$H NMR (600 MHz, MeOD) δ 8.02 (2H, d, J=8.4 Hz), 7.44

(2H, d, J=8.4 Hz), 6.95-6.94 (2H, m), 6.88 (2H, dt, J=1.4, 7.7, 7.8 Hz), 6.80 (2H, t, J=7.8 Hz), 6.74-6.72 (2H, m), 3.83 (1H, dd, J=9.6, 10.2 Hz), 3.40 (1H, ddd, J=4.2, 10.8, 12.0 Hz), 3.11 (1H, ddd, J=4.2, 9.6, 11.4 Hz), 1.94-1.92 (1H, m), 1.80-1.74 (2H, m), 1.68-1.66 (1H, m), 1.35-1.25 (2H, m); $^{13}$C NMR (150 MHz, MeOD) δ 151.7, 149.6, 141.0, 135.3, 129.2, 123.3, 122.5, 120.8, 118.6, 115.4, 73.0, 69.2, 59.3, 32.3, 28.5, 22.3; LCMS m/z 521.2955 ([M+H$^+$], C$_{25}$H$_{24}$F$_3$N$_2$O$_5$S requires 521.5281).

Gram-Scale Synthesis of Example 1

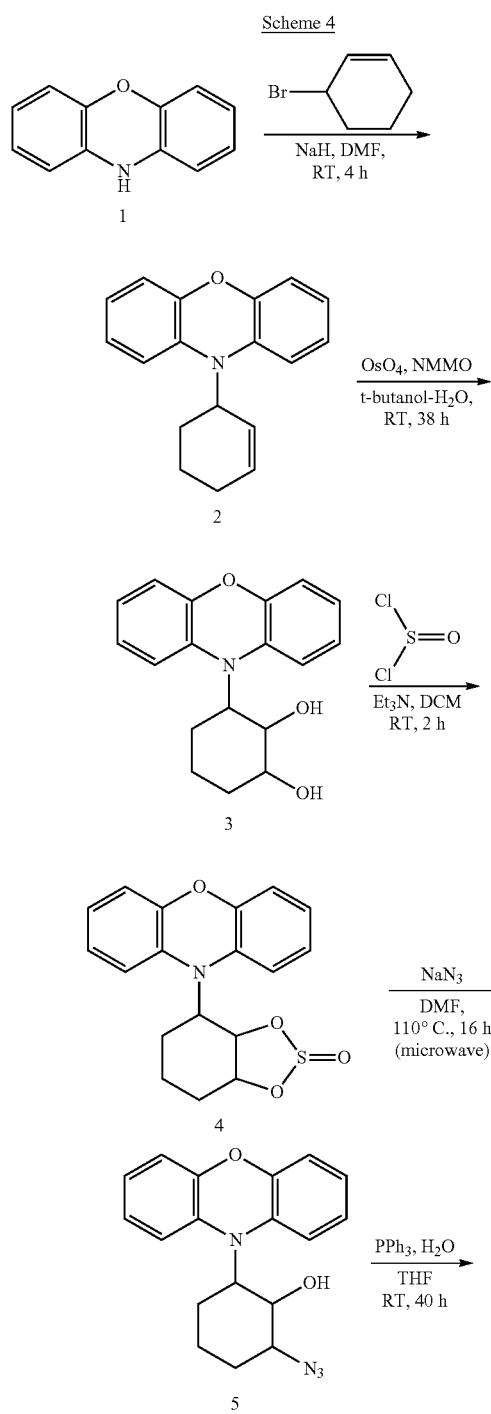

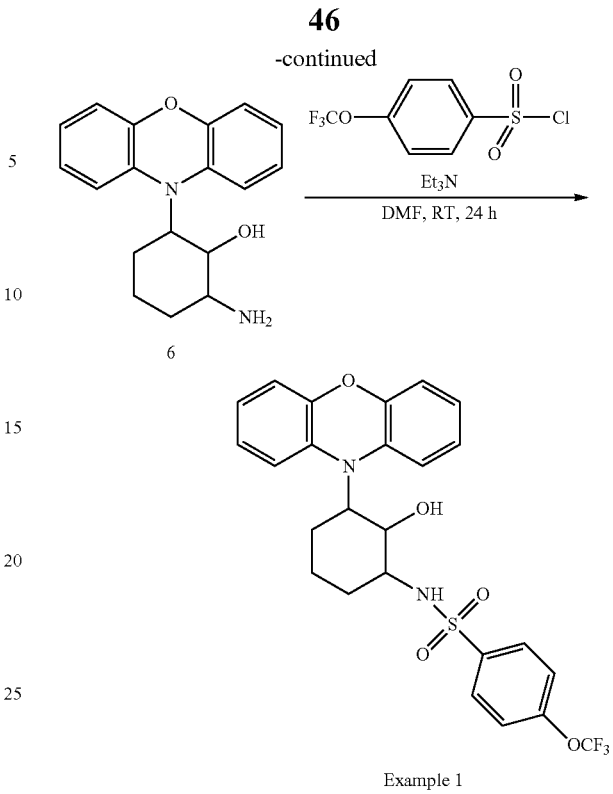

Example 1

All reactions were done in multiple batches (see experimental). The synthesis was commenced by alkylation of commercially available 10H-phenoxazine 1 with commercially available 3-bromocyclohex-1-ene to afford 10-(cyclohex-2-en-1-yl)-10H-phenoxazine 2 in crude 109% yield. An osmium tetroxide catalyzed dihydroxylation of 2 afforded diol 3 in 67% yield. Treatment of diol 3 with thionyl chloride furnished crude sulfide 4 (91% yield). A sodium azide induced azide displacement of 4 afforded crude azide 5 (69% yield), which was taken to the next step without further purification. Amine 6 was synthesized from 5 via a Staudinger reaction in 79% yield. Treating 6 with commercially available 4-(trifluoromethoxy)benzene-1-sulfonyl chloride afforded target sulfonamide Example 1 in a yield of 97%.

Experimental

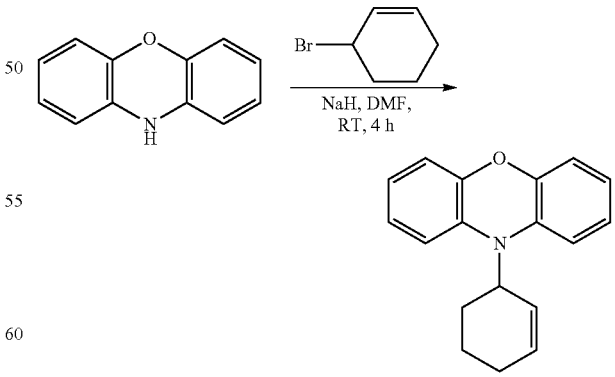

10-(cyclohex-2-en-1-yl)-10H-phenoxazine

The reaction was done on 40.0 g of 10H-phenoxazine (5 reactions of 8.00 g each).

Typical Procedure:

To a solution of 10H-phenoxazine (8.00 g, 43.7 mmol) in DMF (44.0 mL) at RT, was added NaH (1.91 g, 48.1 mmol, 60% dispersion in mineral oil). The mixture was stirred at RT for 1 h. 3-bromocyclohex-1-ene (14.1 g, 87.4 mmol) was added to the above solution, and the reaction mixture was stirred at RT for 4 h.

To the above five reactions—cold water was added, precipitate was filtered, and dried over pump to afford crude 10-(cyclohex-2-en-1-yl)-10H-phenoxazine (62.5 g, 109%). $^1$H NMR (600 MHz, CDCl$_3$) δ 6.84-6.71 (7H, m), 5.94-5.92 (1H, m), 5.94-5.92 (1H, m), 5.84-5.82 (1H, m), 4.58 (1H, bs), 2.23-2.15 (3H, m), 2.07-1.99 (2H, m), 1.84-1.77 (1H, m); $^{13}$C NMR (150 MHz, CDCl$_3$) δ 147.4, 134.8, 130.1, 129.8, 123.5, 121.2, 115.8, 114.4, 55.3, 24.8, 24.6, 22.4; LCMS m/z 264.1354 ([M+H$^+$], C$_{18}$H$_{18}$NO requires 264.3411).

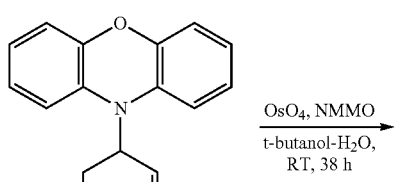

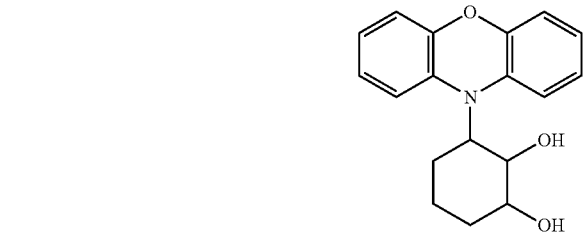

3-(10H-phenoxazin-10-yl)cyclohexane-1,2-diol

The reaction was done on 50.0 g of 10-(cyclohex-2-en-1-yl)-10H-phenoxazine (5 reactions of 10.0 g each).

Typical Procedure:

A solution of 10-(cyclohex-2-en-1-yl)-10H-phenoxazine (10.0 g, 37.9 mmol), 4-methylmorpholine N-oxide (4.89 g, 41.7 mmol), and osmium tetroxide (3.84 mL, 0.379 mmol, 2.5% in tert-butanol) in tert-butanol (50.0 mL) and water (10.0 mL), was stirred at RT for 38 h.

To the above five reactions—solid sodium bisulfite was added (~3.00 g per reaction), the mixture was stirred for 1 h, all mixtures were combined and made into a slurry of silica gel and dichloromethane. The dichloromethane was removed in vacuo to make a silica gel plug. Purification was done in multiple batches by flash chromatography (SiO$_2$, 0%-70% ethyl acetate-hexanes) to afford solid product, which was triturated with 1:4 ethyl acetate-hexanes to afford 3-(10H-phenoxazin-10-yl)cyclohexane-1,2-diol (37.7 g, 67%) as a white powder. $^1$H NMR (600 MHz, DMSO-d$^6$) δ 6.96-6.94 (2H, m), 6.86-6.84 (2H, m), 6.73-6.69 (4H, m), 4.76 (1H, d, J=5.4 Hz), 4.52 (1H, d, J=2.4 Hz), 4.00-3.95 (2H, m), 3.92-3.87 (1H, m), 1.96-1.89 (1H, m), 1.83-1.81 (1H, m), 1.72-1.66 (2H, m), 1.51-1.43 (2H, m); $^{13}$C NMR (150 MHz, DMSO-d$^6$) δ 148.2, 136.1, 124.2, 121.9, 117.4, 115.7, 71.3, 70.5, 62.0, 31.4, 29.4, 19.7; LCMS m/z 298.2582 ([M+H$^+$], C$_{18}$H$_{20}$NO$_3$ requires 298.3558).

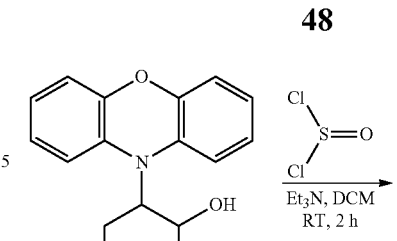

4-(10H-phenoxazin-10-yl)hexahydrobenzo[d][1,3,2]dioxathiole 2-oxide

The reaction was done on 28.0 g of 3-(10H-phenoxazin-10-yl)cyclohexane-1,2-diol (4 reactions of 7.00 g each).

Typical Procedure:

A solution of 3-(10H-phenoxazin-10-yl)cyclohexane-1,2-diol (7.00 g, 13.5 mmol) in dichloromethane (100.0 mL) under argon was cooled to 0° C., and treated with triethylamine (14.9 mL, 107 mmol). Following this thionyl chloride (2.93 mL, 40.4 mmol) was added very slowly over 20 min. The reaction mixture was warmed to RT, stirred for 2 h.

The above four reactions—were partitioned between dichloromethane and water, concentrated to obtain a residue which was purified in multiple batches by flash chromatography (SiO$_2$, 10%-50% ethylacetate-hexanes) to afford solid product, which was triturated with 1:10 ethyl acetate-hexanes to afford 4-(10H-phenoxazin-10-yl)hexahydrobenzo[d][1,3,2]dioxathiole 2-oxide (29.4 g, crude 91%) as an off-white powder which was taken to the next step without further purification.

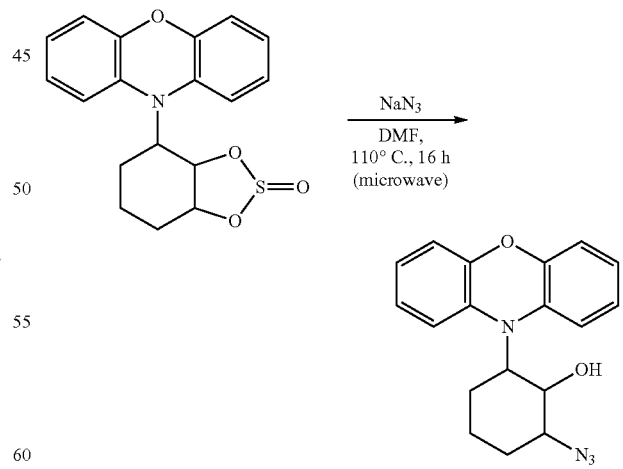

2-azido-6-(10H-phenoxazin-10-yl)cyclohexanol

The reaction was done on 28.0 g of 4-(10H-phenoxazin-10-yl)hexahydrobenzo[d][1,3,2]dioxathiole 2-oxide (7 reactions of 4.00 g each).

Typical Procedure:

A solution of 4-(10H-phenoxazin-10-yl)hexahydrobenzo[d][1,3,2]dioxathiole 2-oxide (4.00 g, 11.6 mmol) in DMF (8.0 mL) was treated with sodium azide (2.27 g, 34.9 mmol). The mixture was heated at 110° C. for 4 h in a sealed 20 mL vial in a Biotage Initiator® microwave. Pressure was released by puncturing the vial cap with a needle, cap was replaced and mixture was heated at 110° C. for 12 h more in the same microwave.

To the above seven reactions—brine (around 400 mL) was added and the mixture was stirred for 3 h. The supernatent aqueous layer was extracted with dichloromethane. The chunky dark precipitate at the bottom was combined with the above dichloromethane layer, silica was added, and solvent was removed in vacuo to make a dry plug. Purification was done in multiple batches by flash chromatography (SiO$_2$, 6%-10% ethylacetate-hexanes) to afford crude 2-azido-6-(10H-phenoxazin-10-yl)cyclohexanol (18.1 g, crude 69%).

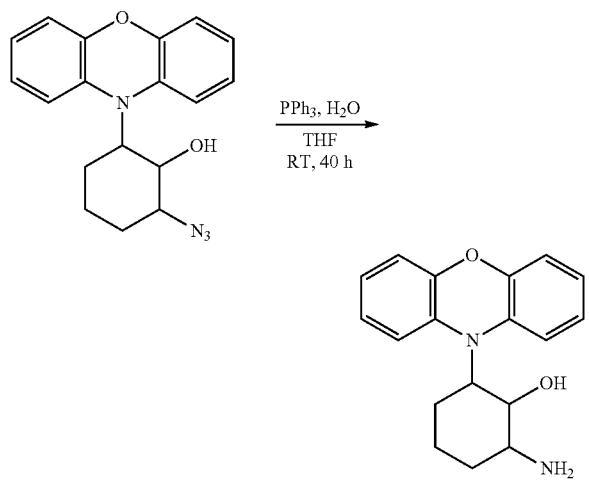

2-amino-6-(10H-phenoxazin-10-yl)cyclohexanol

The reaction was done on 18.0 g of 2-azido-6-(10H-phenoxazin-10-yl)cyclohexanol (6 reactions of 3.00 g each).

Typical Procedure:

A solution of 2-azido-6-(10H-phenoxazin-10-yl)cyclohexanol (3.00 g, 9.31 mmol) in THF (32.0 mL) was cooled to 0° C., treated with PPh$_3$ (2.68 g, 10.2 mmol), H$_2$O (0.042 g, 2.32 mmol), and stirred for 40 h at RT.

The above six reactions—were concentrated to dryness, dissolved in dichloromethane, silica was added, and solvent was removed in vacuo to make a dry plug. Purification was done in multiple batches by flash chromatography (SiO$_2$, 100% hexanes, 50% ethyl acetate-hexanes, 3%, methanol-dichloromethane, 17:2:1 dichloromethane:methanol:35% ammonium hydroxide) to afford 2-amino-6-(10H-phenoxazin-10-yl)cyclohexanol (13.1 g, 79%). $^1$H NMR (600 MHz, CDCl$_3$) δ 6.99-6.77 (8H, m), 4.67 (1H, m), 3.66 (1H, t, J=18.6 Hz), 3.36-3.32 (1H, m), 2.94-2.70 (3H, m), 1.95-1.93 (1H, m), 1.82-1.80 (1H, m), 1.72-1.65 (2H, m), 1.36-1.27 (1H, m), 1.21-1.15 (1H, m); $^{13}$C NMR (150 MHz, CDCl$_3$) δ 150.0, 135.0, 123.8, 123.5, 119.7, 116.2, 74.8, 70.5, 56.2, 33.1, 28.1, 23.0; LCMS m/z 297.2937 ([M+H$^+$], C$_{18}$H$_{21}$N$_2$O$_2$ requires 297.3710).

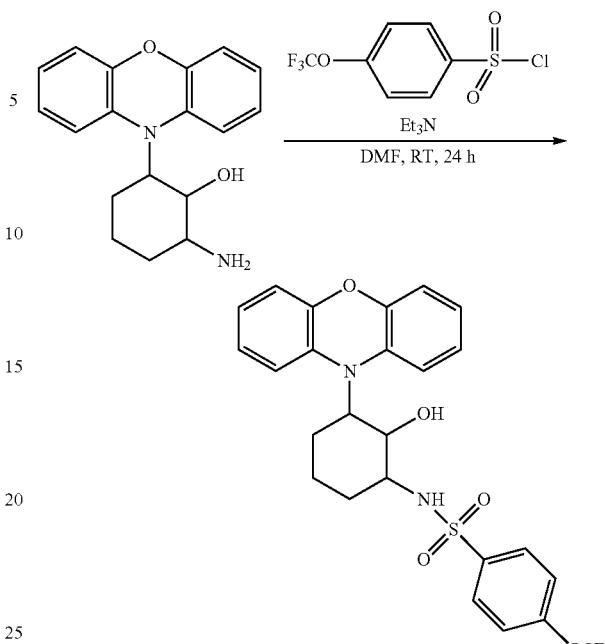

Example 1: N-(2-hydroxy-3-(10H-phenoxazin-10-yl)cyclohexyl)-4-(trifluoromethoxy)benzenesulfonamide The reaction was done on 15.0 g of 2-amino-6-(10H-phenoxazin-10-yl)cyclohexanol (3 reactions of 5.00 g each).

Typical Procedure:

A solution of 2-amino-6-(10H-phenoxazin-10-yl)cyclohexanol (5.00 g, 16.9 mmol) in DCM (55.0 mL), and DMF (11.0 mL) was cooled to 0° C., treated with Et$_3$N (9.42 mL, 67.6 mmol), and 4-(trifluoromethoxy)benzene-1-sulfonyl chloride (3.00 mL, 17.7 mmol). The mixture was warmed to RT, and stirred for 24 h.

The above three reactions were partitioned between water and CH$_2$Cl$_2$. The organic layer was washed with saturated aqueous NaCl (100 mL×5) to remove DMF, and concentrated in vacuo. The residue was dissolved in dichloromethane, silica was added, and solvent was removed in vacuo to make a dry plug. Purification was done in multiple batches by flash chromatography (SiO$_2$, 0%-20% ethylacetate-hexanes) to afford white solid, which was triturated with 9:1 ether-hexanes, filtered, and dried to afford N-(2-hydroxy-3-(10H-phenoxazin-10-yl)cyclohexyl)-4-(trifluoromethoxy)benzenesulfonamide Example 1 (25.38 g, 97%) as a white powder. $^1$H NMR (600 MHz, MeOD) δ 8.02 (2H, d, J=8.4 Hz), 7.44 (2H, d, J=8.4 Hz), 6.95-6.94 (2H, m), 6.88 (2H, dt, J=1.4, 7.7, 7.8 Hz), 6.80 (2H, t, J=7.8 Hz), 6.74-6.72 (2H, m), 3.83 (1H, dd, J=9.6, 10.2 Hz), 3.40 (1H, ddd, J=4.2, 10.8, 12.0 Hz), 3.11 (1H, ddd, J=4.2, 9.6, 11.4 Hz), 1.94-1.92 (1H, m), 1.80-1.74 (2H, m), 1.68-1.66 (1H, m), 1.35-1.25 (2H, m); $^{13}$C NMR (150 MHz, MeOD) δ 151.7, 149.6, 141.0, 135.3, 129.2, 123.3, 122.5, 120.8, 118.6, 115.4, 73.0, 69.2, 59.3, 32.3, 28.5, 22.3; LCMS m/z 521.2955 ([M+H$^+$], C$_{25}$H$_{24}$F$_3$N$_2$O$_5$S requires 521.5281).

Chiral preparative HPLC with CHIRALCEL® OZ-H eluting with 70:30 hexane:ethanol was used to resolve Example 1 into its enantiomers. Peak 1 (retention time 5 min) was Example 2>99% ee; [α]$_D$=−3 (c=1.0, CH$_2$Cl$_2$);

[α]$_D$=+19 (c=1.0, CH$_3$OH) and Peak 2 (retention time 9 min) was, Example 3>99% ee; [α]$_D$=+3 (c=1.0, CH$_2$Cl$_2$); [α]$_D$=−23 (c=1.0, CH$_3$OH). Analytical chiral HPLC was also performed using CHIRALPAK® OZ-H stationary phase column and 1.0 mL/min 70:30 hexane:ethanol.

Stereoselective Synthesis of Example 1b

The compounds of formula I may also be synthesized by utilizing a known chiral starting material in a stereoselective route, removing the necessity of chiral separation of the enantiomers after synthesis of the racemate (or other mixture). The synthesis shown below employs a chiral allylic alcohol that can then be epoxidized and the chiral epoxide opened with the anion of a tricyclic moiety. This method also allows the absolute stereochemistry of Example 1a and Example 1b to be assigned.

To establish the absolute configuration of these compounds, an asymmetric synthesis was carried out (Scheme 4B). Chiral starting material (1S,2R,6S)-2-(benzyloxy)-7-oxabicyclo[4.1.0]heptane 1 was prepared from the known R-(+)-cyclohexen-2-ol by literature methods as shown in Scheme 4A

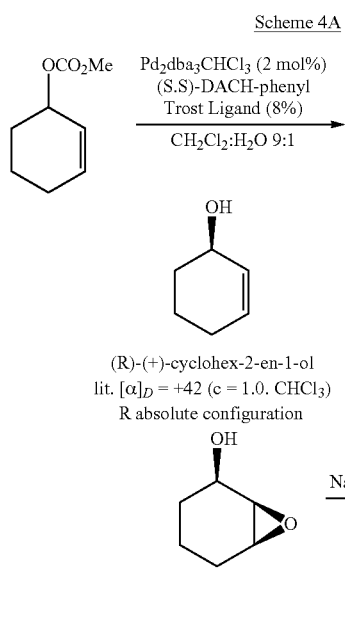

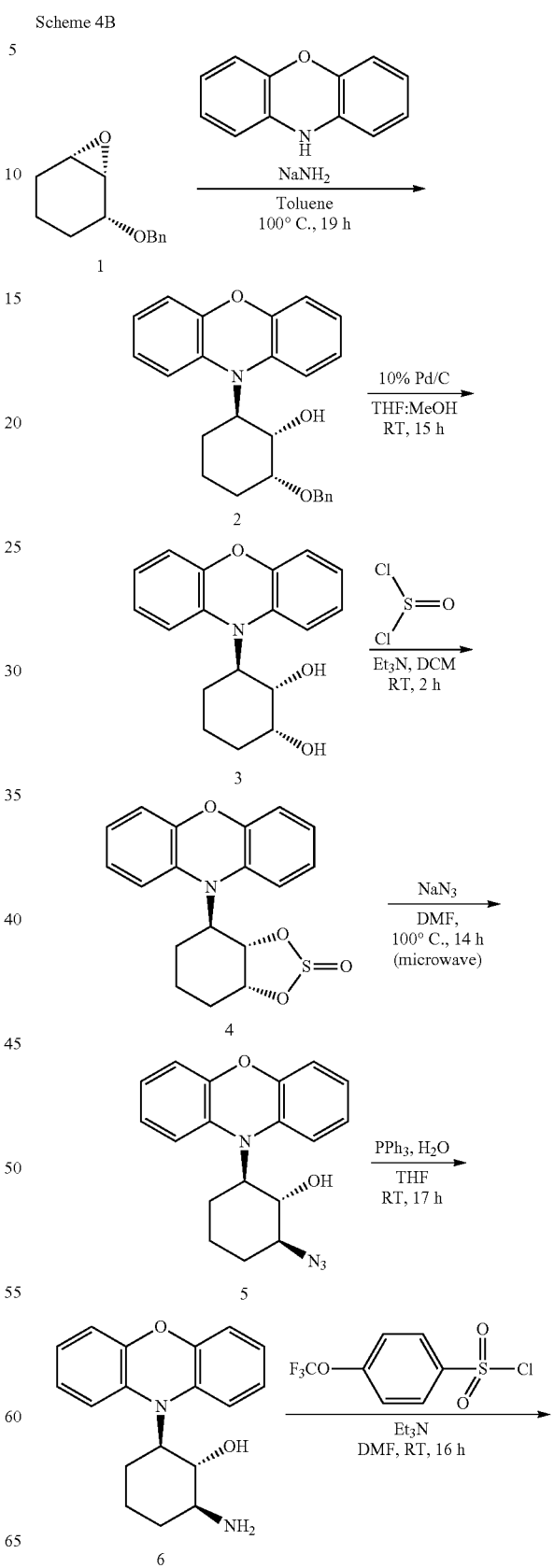

The starting material methyl cyclohex-2-enecarboxylate was synthesized according to methods detailed in the supporting information of the following reference: Timothy R. Ramadhar, Jun-ichi Kawakami, Alan J. Lough, and Robert A. Batey, Org. Lett., 2010, 12 (20), pp 4446-4449. This material (1) was deracemized according to procedures described in Bernhard J. Lussem and Hans-Joachim Gais. J. Am. Chem. Soc. 2003, 125, 6066-6067 to provide the chiral (R)-cyclohex-2-enol (2). Literature lit. [α]$_D$=+42 (c=1.0, CHCl$_3$). The epoxidation of (R)-cyclohex-2-enol (2) was performed according to procedures in Toshio Sato, Yoshihiko Gotoh, Makoto Watanabe, and Tamotsu Fujisawa Chemistry Letters, 1983, 1533-1536 to provide the chiral epoxide (1R,2R,3S)-cis-2,3-epoxycyclohexan-1-ol (3). Benzylation of (1R,2R,3S)-cis-2,3-epoxycyclohexan-1-ol was performed using procedures in Federico Calvani, Paolo Crotti, Cristina Gardelli, Mauro Pineschi. Tetrahedron, 1994, 50(45), 12999-13022 to provide starting material 1 shown in Scheme 4B.

53

-continued

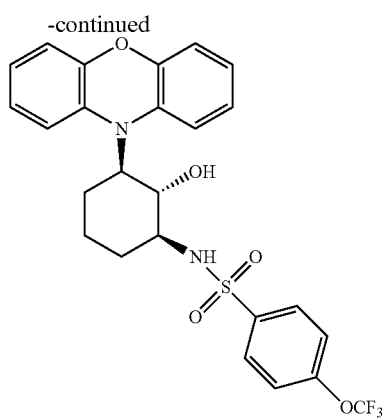

Example 1B

The synthesis was commenced by epoxide opening of previously synthesized (1S,2R,6S)-2-(benzyloxy)-7-oxabicyclo[4.1.0]heptane 1 with commercially available 10H-phenoxazine to afford 2. Compound 2 was deprotected using 10% Pd/C under hydrogen to afford diol 3 in an over-all yield of 41% from 1. Treatment of diol 3 with thionyl chloride furnished crude sulfide 4. A sodium azide induced azide displacement of 4 in a microwave reactor afforded crude azide 5, which was taken to the next step without further purification. Amine 6 was synthesized from 5 via a Staudinger reaction; the overall yield of 6 from 3 was 49%. Treating 6 with commercially available 4-(trifluoromethoxy)benzene-1-sulfonyl chloride afforded target sulfonamide Example 1b in a yield of 22%.

Experimental

54

(1R,2S,3R)-3-(10H-phenoxazin-10-yl)cyclohexane-1,2-diol 3

A solution of 10H-phenoxazine (0.323 g, 1.76 mmol) in toluene (1.0 mL) was treated with sodium amide (50% wt. suspension in toluene, 0.274 g, 3.52 mmol). (1S,2R,6S)-2-(benzyloxy)-7-oxabicyclo[4.1.0]heptane 1 (0.300 g, 1.47 mmol) in toluene (1.6 mL) was added and the mixture heated to 100° C. for 19 h. The mixture was cooled to 25° C. and poured over a solution of saturated aqueous ammonium chloride (100 mL). The organic layer was separated and the aqueous layer was extracted with ethylacetate (3×100 mL). The organic layers were combined, dried (Na$_2$SO$_4$), and concentrated in vacuo. The residue was dissolved in a minimal amount of dichloromethane and purified by flash chromatography (SiO$_2$, 25 g, 0%-20 ethyl acetate-hexanes) to afford crude (1S,2R,6R)-2-(benzyloxy)-6-(10H-phenoxazin-10-yl)cyclohexanol 2 (0.422 g, crude 62%) which was taken to the next step without further purification.

A solution of (1S,2R,6R)-2-(benzyloxy)-6-(10H-phenoxazin-10-yl)cyclohexanol 2 (0.422 g, 1.09 mmol) in THF: MEOH (1:1, 4.6 mL) was treated with 10% Pd/C (0.110 g, 0.110 mmol) and then placed under an atmosphere of H$_2$ (g). The mixture was stirred for 15 h at 25° C. then filtered through a celite pad, washed with hot methanol and ethylacetate, and concentrated in vacuo. The residue was dissolved in a minimal amount of dichloromethane and purified by flash chromatography (SiO$_2$, 10%-50% ethyl acetate-hexanes) to afford (1R,2S,3R)-3-(10H-phenoxazin-10-yl)cyclohexane-1,2-diol 3 (0.201 g, 41% over two steps). $^1$H NMR (600 MHz, MeOD) δ 7.00 (2H, dd, J=7.2, 0.6 Hz), 6.89-6.86 (2H, m), 6.80-6.78 (2H, m), 6.72 (2H, dd, J=7.8, 1.2 Hz), 4.13 (1H, br s), 4.03 (1H, dd, J=10.8, 2.4 Hz), 3.90 (1H, td, J=11.4, 3.6 Hz), 1.94-1.92 (1H, m), 1.85-1.73 (3H, m), 1.53-1.48 (2H, m); ESI-HRMS calcd for C$_{18}$H$_{20}$NO$_3$ [M+H$^-$] 298.1438, found 298.1439.

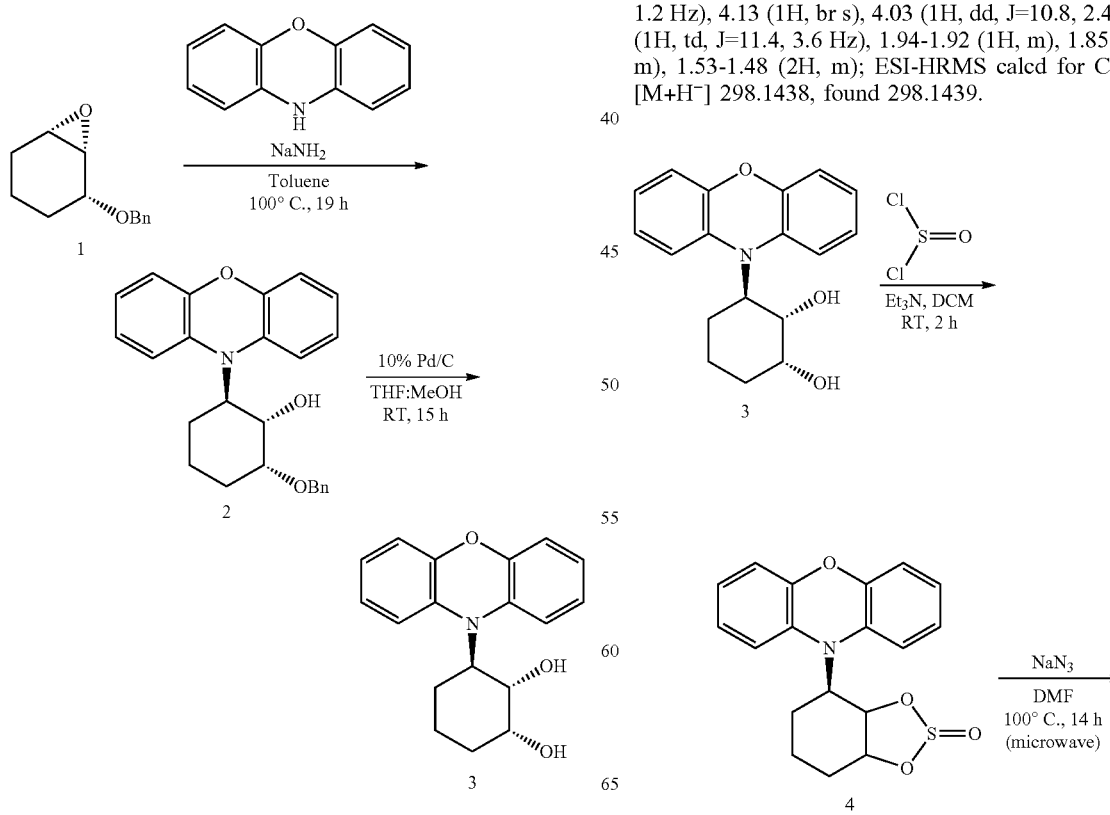

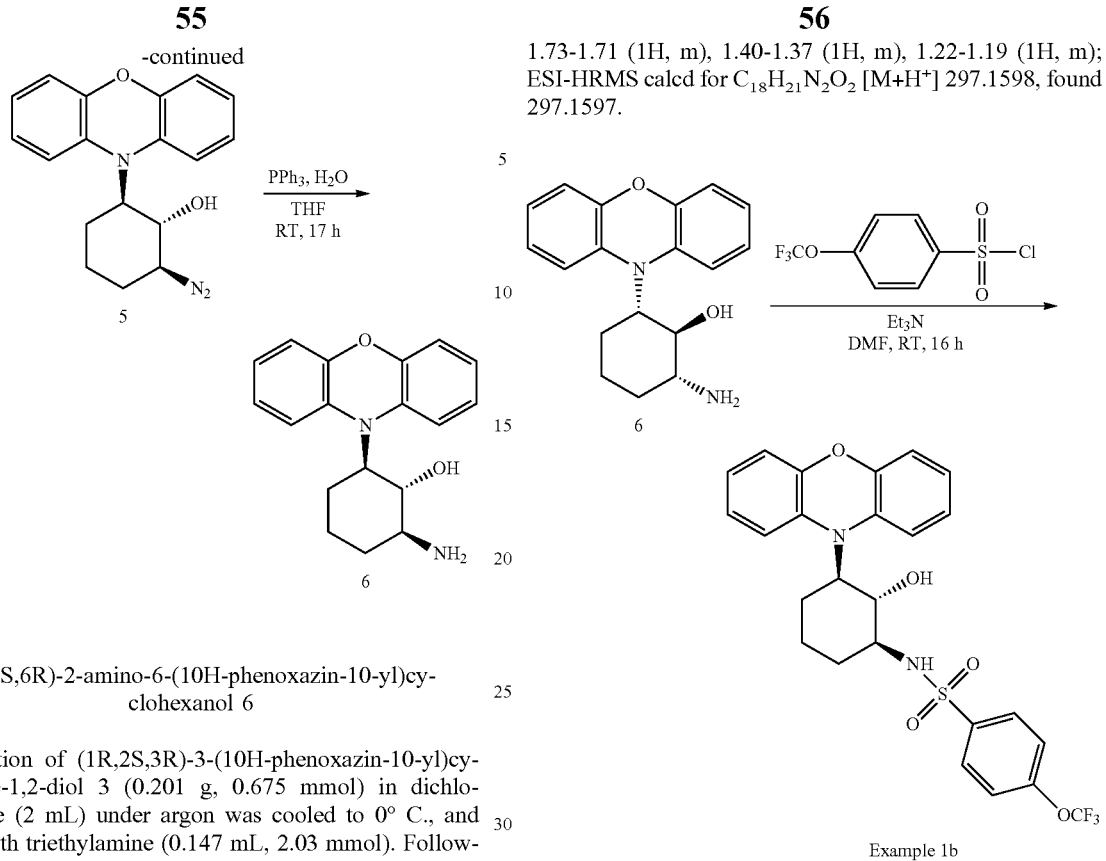

(1R,2S,6R)-2-amino-6-(10H-phenoxazin-10-yl)cyclohexanol 6

A solution of (1R,2S,3R)-3-(10H-phenoxazin-10-yl)cyclohexane-1,2-diol 3 (0.201 g, 0.675 mmol) in dichloromethane (2 mL) under argon was cooled to 0° C., and treated with triethylamine (0.147 mL, 2.03 mmol). Following this thionyl chloride (0.748 mL, 5.40 mmol) was added over 20 min. The reaction mixture was warmed to RT, stirred for 2 h, partitioned between dichloromethane and water, concentrated to obtain a residue which was purified by flash chromatography (SiO$_2$, 10%-50% ethylacetate-hexanes) to afford crude (3aS,4R,7aR)-4-(10H-phenoxazin-10-yl)hexahydrobenzo[d][1,3,2]dioxathiole 2-oxide 4 (0.146 g, crude 63%).

A solution of (3aS,4R,7aR)-4-(10H-phenoxazin-10-yl)hexahydrobenzo[d][1,3,2]dioxathiole 2-oxide 4 (0.146 g, 0.425 mmol) in DMF (2.5 mL) was treated with sodium azide (0.099 g, 1.53 mmol). The mixture was heated at 100° C. for 14 h in a Biotage Initiator® microwave reactor, sat. aq. ammonium chloride was added, mixture was extracted in dichloromethane, washed with brine, and concentrated in vacuo. The residue obtained was purified by flash chromatography (SiO$_2$, 6%-13% ethylacetate-hexanes) to afford crude (1S,2S,6R)-2-azido-6-(10H-phenoxazin-10-yl)cyclohexanol 5 (0.106 g, crude 77%) which was taken to the next step without further purification.

A solution of (1S,2S,6R)-2-azido-6-(10H-phenoxazin-10-yl)cyclohexanol 5 (0.106 g, 0.329 mmol) in THF (1.20 mL) was cooled to 0° C., treated with PPh$_3$ (0.094 g, 0.362 mmol), H$_2$O (0.001 mL, 0.056 mmol), and stirred for 17 h at RT. The solution was concentrated to dryness, dissolved in a minimal amount of dichloromethane and purified by flash chromatography (SiO$_2$, 100% hexanes, 50% ethyl acetate-hexanes, 3%, methanol-dichloromethane, 17:2:1 dichloromethane:methanol:35% ammonium hydroxide) to afford (1R,2S,6R)-2-amino-6-(10H-phenoxazin-10-yl)cyclohexanol 6 (0.076 g, 49% over two steps). $^1$H NMR (600 MHz, MeOD) δ 6.96 (2H, dd, J=7.8, 0.6 Hz), 6.85 (2H, td, J=7.2, 1.2 Hz), 6.77 (2H, td, J=7.8, 1.2 Hz), 6.70 (2H, dd, J=8.4, 1.8 Hz), 3.73-3.70 (1H, m), 3.42-3.38 (1H, m), 2.61-2.57 (1H, m), 1.92-1.90 (1H, m), 1.86-1.82 (2H, m), 1.73-1.71 (1H, m), 1.40-1.37 (1H, m), 1.22-1.19 (1H, m); ESI-HRMS calcd for C$_{18}$H$_{21}$N$_2$O$_2$ [M+H$^+$] 297.1598, found 297.1597.

N-((1S,2S,3R)-2-hydroxy-3-(10H-phenoxazin-10-yl)cyclohexyl)-4-(trifluoromethoxy)benzenesulfonamide (Example 1b)

A solution of (1R,2S,6R)-2-amino-6-(10H-phenoxazin-10-yl)cyclohexanol 6 (0.076 g, 0.256 mmol) in DMF (1.0 mL) was cooled to 0° C., treated with triethylamine (0.143 mL, 1.03 mmol), and 4-(trifluoromethoxy)benzene-1-sulfonyl chloride (0.048 mL, 0.282 mmol). The mixture was warmed to RT, and stirred for 16 h. The mixture was partitioned between water (10 mL) and dichloromethane (10 mL). The organic layer was washed with saturated aqueous NaCl (30 mL×5) to remove DMF, and concentrated in vacuo. The residue was dissolved in a minimal amount of dichloromethane and purified by flash chromatography (SiO$_2$, 9%-50% ethylacetate-hexanes to afford N-((1S,2S,3R)-2-hydroxy-3-(10H-phenoxazin-10-yl)cyclohexyl)-4-(trifluoromethoxy)benzenesulfonamide (Example 1b) (0.029 g, 22%). $^1$H NMR (600 MHz, MeOD) δ 8.02 (2H, d, J=8.4 Hz), 7.44 (2H, d, J=8.4 Hz), 6.95-6.94 (2H, m), 6.88 (2H, dt, J=1.4, 7.7, 7.8 Hz), 6.80 (2H, t, J=7.8 Hz), 6.74-6.72 (2H, m), 3.85-3.82 (1H, m), 3.42-3.37 (1H, m), 3.12-3.09 (1H, m), 1.93-1.91 (1H, m), 1.78-1.74 (2H, m), 1.67-1.66 (1H, m), 1.35-1.27 (2H, m); $^{13}$C NMR (150 MHz, MeOD) δ 151.7, 149.6, 141.0, 135.3, 129.2, 123.3, 122.5, 120.8, 118.6, 115.4, 72.9, 69.2, 59.3, 32.3, 28.5, 22.3; ESI-HRMS calcd for C$_{25}$H$_{24}$F$_3$N$_2$O$_5$S [M+H$^+$] 521.1353, found 521.1349; [α]$_D$=+13 (c=1.0, CH$_2$Cl$_2$); [α]$_D$=−11 (c=1.0, CH$_3$OH);

The enantiomeric identity and purity was also confirmed by analytical chiral HPLC>98% (CHIRALPAK® OZ-H column, 70:30 hexanes-EtOH, 1 mL/min, retention times: 9 min. Thus the material produced by this route is the same as that from Peak 2 of the chromatographic resolution of Example 1, that is Example 1b, and furthermore its absolute steochemistry is established as:

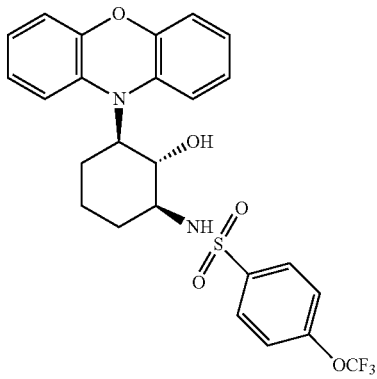

N-((1S,2S,3R)-2-hydroxy-3-(10H-phenoxazin-10-yl)cyclohexyl)-4-(trifluoromethoxy)benzenesulfonamide In addition the absolute configuration of Example 1a is established as:

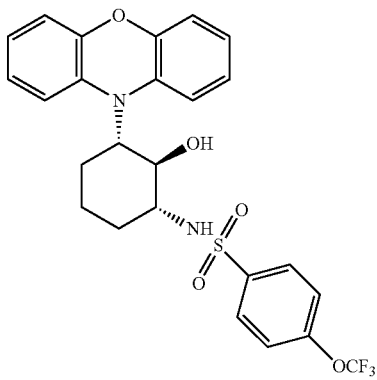

N-((1R,2R,3S)-2-hydroxy-3-(10H-phenoxazin-10-yl)-4-(trifluoroxy)benzenesulfonamide Syntheses of optically enriched Examples 1a and 1b, described above, employ chromatographic separation of racemic Example 1 by chiral HPLC or stereoselective synthesis from optically enriched cyclohexen-2-ol of known configuration. In addition intermediates in the synthesis of Example 1 may be resolved, then optically enriched material carried forward to to give Example 1a or Example 1b. For example, racemic 3-(10H-phenoxazin-10-yl)cyclohexane-1,2-diol (intermediate 3 in Scheme 4B) may be resolved by chiral HPLC using CHIRALPAK® IF-3 analytical column (4.6 mm diameter×150 mm length, 3 micron particle size), 70:30 hexanes-EtOH, 1 mL/min to give enantiomers eluting with retention times 3.7 (Peak1) and 4.7 (Peak2) min respectively.

In Scheme 4, the first stereogenic center is introduced on alkylation of 10H-phenoxazine with 3-bromocyclohex-1-ene to yield racemic 10-(cyclohex-2-en-1-yl)-10H-phenoxazine. An asymmetic synthesis of 10-(cyclohex-2-en-1-yl)-10H-phenoxazine employing chiral catalysis maybe performed to control the first stereogenic center, followed by diastereoselective osmlation to give optically enriched 3-(10H-phenoxazin-10-yl)cyclohexane-1,2-diol as described below.

Asymmetric synthesis of (1R,2S,3R)-3-(10H-phenoxazin-10-yl)cyclohexane-1,2-diol.

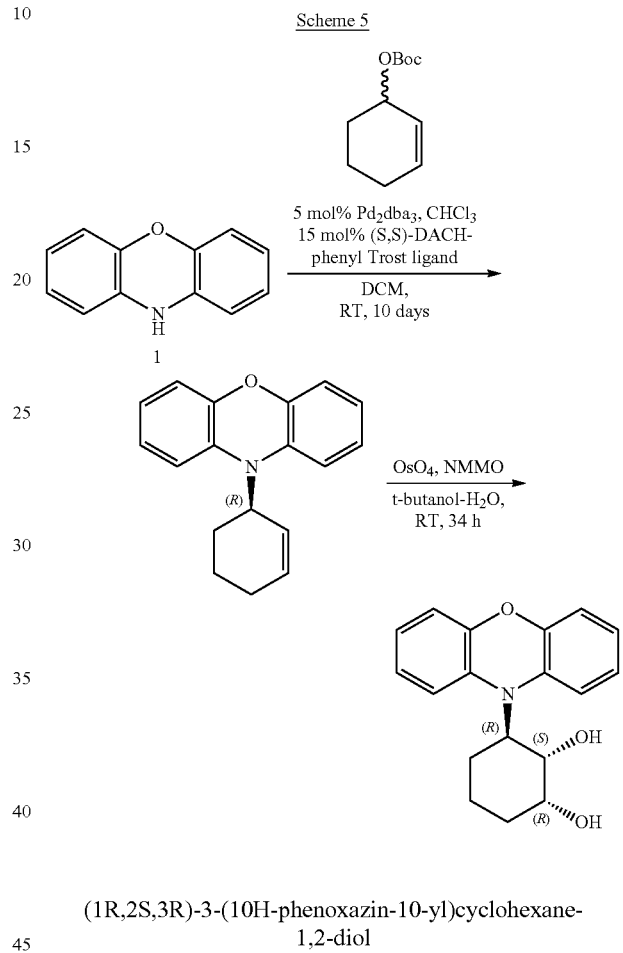

(1R,2S,3R)-3-(10H-phenoxazin-10-yl)cyclohexane-1,2-diol

A 20 mL Biotage® microwave reaction vial was charged with Pd$_2$.dba$_3$. CHCl$_3$ (0.052 g, 0.05 mmol), and (S,S)-DACH-phenyl Trost ligand (0.104 g, 0.15 mmol). The vial was sealed, evacuated and backfilled with argon three times. Dry degassed dichloromethane (2.5 mL) was added to this vial, and the mixture was stirred at room temperature for 30 min. Racemic tert-butyl cyclohex-2-en-1-yl carbonate (0.238 g, 1.20 mmol) was added to the vial and the contents were transferred to a separate 20 mL Biotage® microwave reaction vial containing 10H-phenoxazine (0.183 g, 1.00 mmol) in dry degassed dichloromethane (3.0 mL). The reaction mixture was stirred at room temperature for 10 days. At this point, the reaction mixture was evaporated onto silica gel and subjected to column chromatography (SiO$_2$; 100% hexanes) to afford pure (R)-10-(cyclohex-2-en-1-yl)-10H-phenoxazine (0.114 g, 43%). HRMS m/z 264.1383 ([M+H$^+$], C$_{18}$H$_{18}$NO requires 264.1379).

A solution of (R)-10-(cyclohex-2-en-1-yl)-10H-phenoxazine (0.114 g, 0.432 mmol), 4-methylmorpholine N-oxide monohydrate (0.056 g, 0.476 mmol), and osmium tetroxide (0.040 mL, 0.004 mmol, 2.5% in tert-butanol) in tert-butanol (1.30 mL) and water (0.30 mL), was stirred at RT for 34 h. The reaction mixture was treated with solid sodium bisulfite solution, stirred for 1 h, evaporated on to silica and purified by flash chromatography (SiO$_2$, 0%-70% ethyl acetate-hexanes) to afford (1R,2S,3R)-3-(10H-phenoxazin-10-yl)cyclohexane-1,2-diol (0.101 g, 79%). $^1$H NMR (600 MHz, MeOD) δ 7.01-7.00 (2H, m), 6.88 (2H, bs), 6.80 (2H, m), 6.73-6.72 (2H, m), 4.14 (1H, m), 4.04-4.03 (1H, m), 3.90 (1H, bs), 1.93 (1H, bs), 1.84-1.74 (3H, m), 1.53-1.52 (2H, m); $^{13}$C NMR (150 MHz, MeOD) δ 123.3, 122.3, 118.7, 115.3, 72.2, 70.6, 64.3, 30.8, 28.7, 19.1; HRMS m/z 298.1437 ([M+H$^+$], C$_{18}$H$_{20}$NO$_3$ requires 298.1438). Material produced in this fashion exhibited [α]$_D$=+0.03 (c=1.0, CH$_2$C$_{12}$). The enantiomeric purity was confirmed by analytical chiral HPLC>99% (CHIRALPAK® IF-3 column, 70:30 hexanes-EtOH, 1.5 mL/min, retention time: 4.7 min. This material co-elutes with 4.7 min, peak 2 of the racemate. In addition (10H-phenoxazin-10-yl)cyclohexane-1,2-diol produced by the method of Scheme 1B, i.e. from (R)-(+)-cyclohex-2-enol, has retention time 4.7 min by the same chiral HPLC analysis, which confirms the absolute stereochemistry of the product from the asymmetric catalysis as that shown above, i.e. (R)-10-(cyclohex-2-en-1-yl)-10H-phenoxazine and (1R,2S,3R)-3-(10H-phenoxazin-10-yl)cyclohexane-1,2-diol. The other enantiomeric series may be accessed by the same method but employing the opposite enantiomer of the chiral ligand, i.e. (R,R)-DACH-phenyl Trost ligand in the asymmetric allylation step.

Example 2

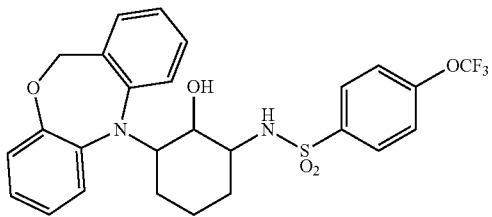

The synthesis begins with alkylation of commercially available 5,11-dihydrodibenzo[b,e][1,4]oxazepine with commercially available 3-bromocyclohex-1-ene to afford 5-(cyclohex-2-en-1-yl)-5,11-dihydrodibenzo[b,e][1,4]oxazepine in 83% yield. An osmium tetroxide catalyzed dihydroxylation of the alkene afforded diol in 40% yield. Treatment of diol with methanesulfonyl choride furnished mesylate in 10% yield. A sodium azide induced azide displacement of the mesylate afforded regioisomeric azides: the 2-azido-6-tricyclylcyclohexanol in 29% yield and the 2-azido-3-tricyclylcyclohexanol in 17% yield. The 2-amino-6-tricyclylcyclohexanol was synthesized from the 2-azido-6-tricyclylcyclohexanol via a Staudinger reaction in 80% yield. Treating 2-amino-6-tricyclylcyclohexanol with commercially available 4-(trifluoromethoxy)benzene-1-sulfonyl chloride afforded target sulfonamide Example 2 in a yield of 53%.

5-(cyclohex-2-en-1-yl)-5,11-dihydrodibenzo[b,e][1,4]oxazepine. To a solution of 5,11-dihydrodibenzo[b,e][1,4]oxazepine (4.37 g, 22.1 mmol) in DMF (22 mL) at RT, was added NaH (0.975 g, 24.4 mmol, 60% dispersion in mineral oil). The mixture was stirred at RT for 20 min. 3-bromocyclohex-1-ene (7.12 g, 44.2 mmol) was added to the above solution at RT, and the reaction mixture was stirred for 3 h, neutralized with sat. aq. NH$_4$Cl, extracted with dichloromethane, concentrated in vacuo to give a residue which was purified by flash chromatography (SiO$_2$, 0%-5% ethylacetate in hexanes) to afford 5-(cyclohex-2-en-1-yl)-5,11-dihydrodibenzo[b,e][1,4]oxazepine (5.08 g, 83%). $^1$H NMR (600 MHz, CDCl$_3$) δ 7.26-7.23 (1H, m), 7.17-7.14 (3H, m), 7.06-7.04 (1H, m), 6.97-6.94 (1H, m), 6.89-6.87 (1H, m), 6.77-6.74 (1H, m), 5.99-5.98 (1H, m), 5.71 (1H, d, J=10.2 Hz), 4.58 (1H, d, J=14.4 Hz), 4.35-4.32 (2H, m), 2.16-2.06 (2H, m), 1.97-1.86 (2H, m), 1.70-1.65 (2H, m); $^{13}$C NMR (150 MHz, CDCl$_3$) δ 157.8, 147.5, 141.0, 131.9, 131.2, 129.7, 128.7, 128.1, 124.4, 123.7, 122.1, 120.1, 119.6, 118.2, 56.9, 48.6, 26.9, 25.2, 21.6; LCMS m/z 278.3577 ([M+H$^-$], C$_{19}$H$_{20}$NO requires 278.3677).

(1S,2R,3S)-rel-3-(dibenzo[b,e][1,4]oxazepin-5(11H)-yl)cyclohexane-1,2-diol. A solution of 5-(cyclohex-2-en-1-yl)-5,11-dihydrodibenzo[b,e][1,4]oxazepine (5.08 g, 18.3 mmol), osmium tetroxide (1.84 mL, 0.183 mmol, 2.5% in tert-butanol), and N-Methylmorpholine N-oxide (2.35 g, 20.1 mmol) in tert-butanol:water (25 mL:5 mL) was stirred at RT for 34 h. The reaction mixture was treated with solid sodium bisulfite for 1 h, concentrated, and purified by flash chromatography (SiO$_2$, 0%-70% ethyl acetate-hexanes) to afford Rac-(1S,2R,3S)-3-(dibenzo[b,e][1,4]oxazepin-5(11H)-yl)cyclohexane-1,2-diol. (2.30 g, 40%). $^1$H NMR (600 MHz, DMSO-d$^6$) δ 7.31 (1H, dd, J=7.2, 1.2 Hz), 7.24 (1H, td, J=7.8, 1.8 Hz), 7.11-7.10 (1H, m), 7.07-7.05 (1H, m), 7.00-6.97 (2H, m), 6.88 (1H, td, J=7.8, 1.8 Hz), 6.62-6.60 (1H, m), 4.59 (1H, d, J=14.4 Hz), 4.43 (1H, d, J=3.6 Hz), 4.39 (1H, d, J=5.4 Hz), 4.28 (1H, d, J=14.4 Hz), 3.97 (1H, bs), 3.81 (1H, td, J=4.8, 10.2 Hz), 3.65 (1H, td, J=3.0, 6.0 Hz), 1.67-1.65 (1H, m), 1.59-1.46 (3H, m), 1.42-1.35 (2H, m); $^{13}$C NMR (150 MHz, CDCl$_3$) δ 150.6, 129.0, 128.5, 124.4, 123.6, 123.1, 122.0, 120.4, 72.5, 69.0, 62.0, 49.9, 29.9, 27.5, 19.6; LCMS m/z 312.3229 ([M+H$^+$], C$_{19}$H$_{22}$NO$_3$ requires 312.3823).

(1S,2R,3S)-rel-3-(dibenzo[b,e][1,4]oxazepin-5(11H)-yl)-2-hydroxycyclohexyl methanesulfonate. To a solution of Rac-(1S,2R,3S)-3-(dibenzo[b,e][1,4]oxazepin-5(11H)-yl)cyclohexane-1,2-diol (2.30 g, 7.39 mmol) in pyridine (16.0 mL) under argon, at 0° C., was added methane sulfonyl chloride (0.572 mL, 7.39 mmol). The mixture was stirred for 16 h at RT. The reaction mixture was treated with 1 N HCl, extracted with DCM, organic layer was washed with brine, concentrated, to obtain a residue which was purified by flash chromatography (SiO$_2$, 90% dichloromethane-hexanes) to afford Rac-(1S,2R,3S)-3-(dibenzo[b,e][1,4]oxazepin-5(11H)-yl)-2-hydroxycyclohexyl methanesulfonate (0.301 g, 10%). $^1$H NMR (600 MHz, CD$_3$OD) δ 7.29-7.28 (1H, m), 7.25-7.23 (1H, m), 7.11-7.09 (2H, m), 7.06-7.04 (2H, m), 6.97-6.94 (1H, m), 6.81-6.79 (1H, m), 4.89-4.87 (1H, m), 4.45 (2H, s), 4.38-4.37 (1H, m), 4.06 (1H, td, J=10.2, 3.6 Hz), 2.94 (3H, s), 1.85-1.82 (1H, m), 1.72-1.58 (4H, m), 1.51-1.49 (1H, m); $^{13}$C NMR (150 MHz, CD$_3$OD) δ 157.9, 149.6, 141.0, 130.7, 128.7, 128.6, 124.1, 123.4, 121.9, 121.4, 121.1, 119.4, 83.2, 69.1, 59.3, 48.8, 37.5, 30.7, 29.0, 18.6; LCMS m/z 390.3659 ([M+H$^+$], C$_{20}$H$_{24}$NO$_5$S requires 390.4727).

(1R,2R,6S)-rel-2-azido-6-(dibenzo[b,e][1,4]oxazepin-5(11H)-yl)cyclohexanol. A solution of (1S,2R,3S)-rel-3-(dibenzo[b,e][1,4]oxazepin-5 (11H)-yl)-2-hydroxycyclohexyl methanesulfonate (0.301 g, 0.773 mmol) in DMF (1 mL) was treated with sodium azide (0.075 g, 1.16 mmol). The mixture was heated at 110° C. for 14 h in a Biotage Initiator® microwave reactor, sat. aq. ammonium chloride was added, mixture was extracted in dichloromethane, and concentrated in vacuo. The residue obtained was purified by flash chromatography (SiO$_2$, 10% ethylacetate-hexanes) to afford the major product—(1R,2R,6S)-rel-2-azido-6-(dibenzo[b,e][1,4]oxazepin-5(11H)-yl)cyclohexanol (0.075 g, 29%), and the minor product—(1R,2R,6S)-rel-2-azido-3-(dibenzo[b,e][1,4]oxazepin-5(11H)-yl)cyclohexanol (0.044 g, 17%). $^1$H NMR (600 MHz, CD$_3$OD) δ 7.28 (1H, dd, J=7.2, 1.2 Hz), 7.23 (1H, td, J=7.8, 1.2 Hz), 7.12-7.11 (2H, d), 7.06-7.03 (2H, m), 6.92-6.89 (1H, m), 6.72-6.69 (1H, m), 4.65 (1H, d, J=14.4 Hz), 4.42 (1H, d, J=14.4 Hz), 3.83 (1H, td, J=10.2, 4.8 Hz), 3.63 (1H, td, J=10.8, 4.8 Hz), 3.35-3.32 (1H, m), 2.05-2.01 (2H, m), 1.75-1.73 (1H, m), 1.43-1.31 (3H, m); $^{13}$C NMR (150 MHz, CD$_3$OD) δ 158.8, 148.4, 142.1, 131.1, 128.8, 128.2, 123.9, 123.6, 121.4, 120.5, 119.8, 119.4, 71.9, 69.2, 60.8, 46.9, 33.6, 31.3, 20.7; LCMS m/z 337.2954 ([M+H$^+$], C$_{19}$H$_{21}$N$_4$O$_2$ requires 337.3951). $^1$H NMR (600 MHz, CD$_3$OD) δ 7.25-7.21 (2H, m), 7.12-7.02 (4H, m), 6.95-6.92 (1H, m), 6.79-6.77 (1H, m), 4.42 (2H, s), 4.21 (1H, d, J=1.2 Hz), 3.98 (1H, td, J=11.4, 3.6 Hz), 3.61-3.60 (1H, dd, J=10.8, 3.0 Hz), 1.79-1.77 (1H, m), 1.66-1.61 (2H, m), 1.55-1.46 (3H, m); $^{13}$C NMR (150 MHz, CD$_3$OD) δ 158.0, 149.3, 140.6, 131.1, 128.6, 128.3, 123.9, 123.3, 121.4, 121.0, 120.8, 119.4, 69.4, 65.4, 59.2, 46.91, 31.2, 29.0, 19.0; LCMS m/z 337.3301 ([M+H$^+$], C$_{19}$H$_{21}$N$_4$O$_2$ requires 337.3951).

(1S,2R,6S)-rel-2-amino-6-(dibenzo[b,e][1,4]oxazepin-5 (11H)-yl)cyclohexanol. A solution of (1R,2R,6S)-rel-2-azido-6-(dibenzo[b,e][1,4]oxazepin-5(11H)-yl)cyclohexanol (0.075 g, 0.223 mmol) in THF (0.8 mL) was cooled to 0° C., treated with PPh$_3$ (0.064 g, 0.245 mmol), H$_2$O (0.001 mL, 0.056 mmol), and stirred for 17 h at RT. The solution was concentrated to dryness, dissolved in a minimal amount of CH$_2$Cl$_2$ and purified by flash chromatography (SiO$_2$, 100% hexanes, 50% ethyl acetate-hexanes, 5%, methanol-dichloromethane, 17:2:1 dichloromethane:methanol:35% ammonium hydroxide) to afford (1S,2R,6S)-rel-2-amino-6-(dibenzo[b,e][1,4]oxazepin-5(11H)-yl)cyclohexanol (0.055 g, 80%). $^1$H NMR (600 MHz, CD$_3$OD) δ 7.29-7.25 (3H, m), 7.61-7.15 (1H, m), 7.08-7.04 (2H, m), 6.93 (1H, td, J=7.8, 1.8 Hz), 6.75-6.72 (1H, m), 4.73 (1H, d, J=15.0 Hz), 4.42 (1H, d, J=15 Hz), 3.86 (1H, td, J=10.2, 4.8 Hz), 3.25 (1H, dd, J=10.2, 10.2 Hz), 2.92 (1H, td, J=10.8, 4.2 Hz), 2.10-2.09 (1H, m), 1.93-1.91 (1H, m), 1.76-1.74 (1H, m), 1.49-1.41 (1H, m), 1.24-1.18 (1H, m); $^{13}$C NMR (150 MHz, CD$_3$OD) δ 157.8, 148.4, 143.1, 131.1, 128.7, 127.9, 124.2, 123.8, 121.2, 120.9, 120.0, 119.8, 73.4, 69.1, 51.1, 46.5, 34.3, 32.8, 21.3; LCMS m/z 311.2788 ([M+H$^+$], C$_{19}$H$_{23}$N$_2$O$_2$ requires 311.3976).

N-((1R,2R,3S)-rel-3-(dibenzo[b,e][1,4]oxazepin-5(11H)-yl)-2-hydroxycyclohexyl)-4-(trifluoromethoxy)benzenesulfonamide. A solution of (1S,2R,6S)-rel-2-amino-6-(dibenzo[b,e][1,4]oxazepin-5(11H)-yl)cyclohexanol (0.055 g, 0.177 mmol) in DMF (1.5 mL) was cooled to 0° C., treated with Et$_3$N (0.030 mL, 0.212 mmol), and 4-(trifluoromethoxy)benzene-1-sulfonyl chloride (0.033 mL, 0.195 mmol). The mixture was warmed to RT, and stirred for 4 h. The mixture was partitioned between water (10 mL) and CH$_2$Cl$_2$ (10 mL). The organic layer was washed with saturated aqueous NaCl (30 mL×3) to remove DMF, and concentrated in vacuo. The residue was dissolved in a minimal amount of CH$_2$Cl$_2$ and purified by flash chromatography (SiO$_2$, 25%-50% ethylacetate-hexanes) to afford N-((1R,2R,3S)-rel-3-(dibenzo[b,e][1,4]oxazepin-5(11H)-yl)-2-hydroxycyclohexyl)-4-(trifluoromethoxy)benzenesulfonamide (0.050 g, 53%). $^1$H NMR (600 MHz, CD$_3$OD) δ 7.74-7.72 (2H, m), 7.26-7.24 (1H, m), 7.18-6.90 (7H, m), 6.93-6.90 (1H, m), 6.73-6.70 (1H, m), 4.31 (1H, d, J=14.4 Hz), 4.23 (1H, d, J=14.4 Hz), 3.83 (1H, dd, J=10.2, 4.8 Hz), 3.47 (1H, dd, J=10.2, 3.6 Hz), 3.29 (1H, dd, J=10.2, 10.2 Hz), 2.06-2.00 (2H, m), 1.69-1.68 (1H, m), 1.41-1.28 (3H, m); $^{13}$C NMR (150 MHz, CD$_3$OD) δ 158.2, 151.5, 148.9, 142.6, 140.2, 130.2, 128.9, 128.6, 124.5, 123.9, 121.3, 120.7, 120.5, 119.9, 119.5, 71.3, 69.3, 53.4, 33.9, 33.2, 20.8; LCMS m/z 535.2464 ([M+H$^+$], C$_{26}$H$_{27}$F$_3$N$_2$O$_5$S requires 536.5621).

Examples 3, 4, 5, 6 and 7

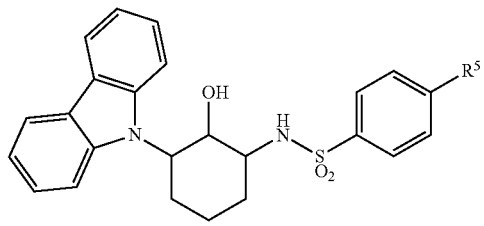

R$^5$=OCF$_3$ (Ex. 3), R$^5$=Cl (Ex. 4), R$^5$=CN (Ex. 5), R$^5$=OCH$_3$ (Ex. 6), R$^5$=H (Ex. 7).

First route to racemic Example 3:

9-(cyclohex-2-en-1-yl)-9H-carbazole. A solution of carbazole (4.00 g, 23.9 mmol) in DMF (40 mL) was cooled to 0° C., treated with NaH (60% dispersion in mineral oil, 1.00 g, 25.1, mmol), stirred for 0.5 h, then treated with 3-bromocyclohex-1-ene (3.03 mL, 26.3 mmol). The mixture was warmed to 25° C., and stirred for 14 h. The mixture was partitioned between saturated aqueous NaCl (100 mL), and CH$_2$Cl$_2$ (300 mL). The organic layer was washed with saturated aqueous NaCl (3×100 mL), dried (Na$_2$SO$_4$), and concentrated in vacuo. The residue was dissolved in a minimal amount of CH$_2$Cl$_2$ and purified by flash chromatography (SiO$_2$, 100% hexanes). The purified fractions were combined, dissolved in a minimal amount of methanol and stirred until a white solid precipitated affording the title compound as a white solid (5.41 g, 91%). $^1$H NMR (600 MHz, CDCl$_3$) δ 8.12 (2H, d, J=7.8 Hz), 7.56 (2H, d, J=7.8 Hz), 7.43 (2H, t, J=7.2 Hz), 7.23 (2H, t, J=7.2 Hz), 6.11-6.14 (1H, m), 5.94 (1H, d, J=10.2 Hz), 5.33-5.38 (1H, m), 2.33-2.36 (1H, m), 2.22-2.28 (2H, m), 2.09-2.12 (1H, m), 2.02-2.05 (1H, m), 1.89-1.92 (1H, m); $^{13}$C NMR (150 MHz, CDCl$_3$) δ 140.1, 131.0, 129.1, 125.5, 123.5, 123.4, 120.4, 118.9, 52.0, 27.7, 25.0, 22.2;

(1R,2S,3R)-rel-3-(9H-carbazol-9-yl)cyclohexane-1,2-diol. A solution of 9-(cyclohex-2-en-1-yl)-9H-carbazole (4.00 g, 16.2 mmol) in t-BuOH-H$_2$O 5:1 (20.0 mL) at 25° C. was treated with OsO$_4$ (2.5 wt. % solution in t-BuOH, 2.02 mL, 0.162 mmol) and N-methyl morpholine N-oxide (2.08 g, 17.8 mmol). The mixture was stirred for 14 h at 25° C., treated with a saturated aqueous solution of sodium hydrosulfite (5 mL) and stirred for an additional 1 h. The mixture was concentrated in vacuo and the residue was taken up in a minimal amount of CH$_2$Cl$_2$ and purified by flash chromatography (SiO$_2$, 0-35% ethyl acetate-hexanes) to afford the title compound as a clear foam (4.86 g, 99%). $^1$H NMR (600 MHz, CDCl$_3$) δ 8.10 (2H, br s), 7.44 (2H, br s), 7.32 (1H, br s), 7.24 (3H, br s), 4.65 (1H, td, J=14.4, 4.2 Hz), 4.65 (1H, td, J=10.2 Hz), 3.75 (1H, s), 2.92 (2H, br s), 2.27 (1H, qd, J=14.4, 5.4 Hz), 1.86-1.94 (3H, m), 1.62-1.64 (1H, m), 1.43 (1H, t, J=14.4 Hz); LCMS m/z 282.1503 ([M+H$^+$], C$_{18}$H$_{19}$NO$_2$ requires 282.1489).

(1R,2S,3R)-rel-3-(9H-carbazol-9-yl)-2-hydroxycyclohexyl methanesulfonate. A solution of (1R,2S,3R)-rel-3-

(9H-carbazol-9-yl)cyclohexane-1,2-diol (4.86 g, 15.7 mmol) in pyridine (5.0 mL) was cooled to 0° C. and treated dropwise with methanesulfonyl chloride (1.22 mL, 15.7 mmol). The mixture was warmed to 25° C., stirred for 3 h, and then concentrated in vacuo. The residue was suspended in $CH_2Cl_2$ (200 mL) and the organic phase was washed with 1 M HCl (3×100 mL), dried ($Na_2SO_4$), and concentrated in vacuo. The residue was dissolved in a minimal amount of $CH_2Cl_2$ and purified by flash chromatography ($SiO_2$, 0-35% ethyl acetate-hexanes) to afford the title compound as a white solid (6.12 g, 99%). $^1$H NMR (600 MHz, $CDCl_3$) δ 8.08 (2H, br s), 2H[7.59 (br s), 7.50 (br s)], 7.46 (2H, t, J=7.2 Hz), 7.24 (2H, t, J=7.2 Hz), 2.92 (1H, br s), 5.40 (1H, d, J=10.2 Hz), 5.14 (1H, td, J=12.0, 4.2 Hz), 4.51 (1H, br s), 2.29 (1H, qd, J=13.2, 3.6 Hz), 2.16-2.18 (1H, m), 2.10-2.11 (1H, m), 2.02-2.06 (1H, m), 1.76 (2H, t, J=12.0 Hz), 1.54 (3H, s); LCMS m/z 360.1267 ([M+H]$^+$, $C_{19}H_{21}NO_4S$ requires 360.1264).

(1R,2S,6R)-rel-2-azido-6-(9H-carbazol-9-yl)cyclohexanol. A solution of (1R,2S,3R)-rel-3-(9H-carbazol-9-yl)-2-hydroxycyclohexyl methanesulfonate (6.12 g, 17.0 mmol) in DMF (10.0 mL) was treated with $NaN_3$ (1.66 g, 25.5 mmol) and heated to 70° C. for 14 h. The mixture was cooled to 25° C. and partitioned between saturated aqueous NaCl (100 mL) and $CH_2Cl_2$ (300 mL). The organic layer was washed with saturated aqueous NaCl (3×100 mL), dried ($Na_2SO_4$), and concentrated in vacuo. The residue was taken up in a minimal amount of $CH_2Cl_2$ and purified by flash chromatography ($SiO_2$, 0-20% ethyl acetate-hexanes) to afford the title compound as a beige oil (0.792 g, 15%), with the remainder as unreacted starting material. $^1$H NMR (600 MHz, $CDCl_3$) δ (as a mixture of rotamers) 2H[8.13 (t, J=8.4 Hz), 8.09 (t, J=7.8 Hz)], 7.57 (1H, t, J=9.6 Hz), 7.45-7.51 (2H, m), 7.43 (1H, t, J=6.0 Hz), 2H[7.30 (t, J=7.8 Hz), 7.26-7.28 (m)], 5.32 (1H, t, J=9.6 Hz), 1H[4.64 (td, J=4.2 Hz), 4.40-4.48 (m)], 1H[3.67 (ddd, J=12.6, 9.6, 4.2 Hz), 3.53-3.57 (m)], 1H[2.60, qd, J=13.2, 3.6 Hz), 2.45 (qd, J=12.0, 3.6 Hz)], 1H[2.34-2.37 (m), 2.25 (br s)], 2.17 (1H, m), 3H[2.03-2.06 (m), 2.02 (s), 1.93-2.00 (m)], 2H[1.74 (qd, J=13.8, 3.6 Hz), 1.53-1.65 (m)]; LCMS m/z 307.1559 ([M+H]$^+$, $C_{20}H_{24}N_2O$ requires 307.1553).

(1R,2S,6R)-rel-2-amino-6-(9H-carbazol-9-yl)cyclohexanol. A solution of (1R,2S,6R)-rel-2-azido-6-(9H-carbazol-9-yl)cyclohexanol. (0.792 g, mmol) in DMF (10.0 mL) was treated with $PPh_3$ (4.71 g, 18.0 mmol), $H_2O$ (0.5 mL), and stirred for 14 h at 25° C. The mixture was concentrated in vacuo, taken up in a minimal amount of $CH_2Cl_2$ and purified by flash chromatography ($SiO_2$, 0-50% ethyl acetate-hexanes to remove nonpolar impurities, followed by 0-3% $MeOH$—$CH_2Cl_2$ to remove triphenylphosphine oxide, followed by 17:2:1 $CH_2Cl_2$:$MeOH$:$NH_4OH$ to elute the product). The purified fractions were combined, dried azeotropically with toluene to afford the title compound as a beige oil (0.238 g, 39%). $^1$H NMR (600 MHz, $CDCl_3$) δ 8.13 (1H, d, J=7.8 Hz), 8.08 (1H, d, J=7.8 Hz), 7.58 (1H, d, J=8.4 Hz), 7.45 (1H, d, J=4.2 Hz), 7.40 (1H, t, J=7.8 Hz), 7.19-7.26 (2H, m), 7.08 (1H, t, J=6.6 Hz), 4.33-4.37 (1H, ddd, J=12.6, 9.6, 6.0 Hz), 4.03 (1H, t, J=9.6 Hz), 2.65-2.69 (1H, ddd, J=12.0, 9.0, 3.6 Hz), 2.40 (1H, qd, J=13.2, 4.2 Hz), 1.88-1.90 (1H, m), 1.84 (1H, dt, J=10.8, 3.0 Hz), 1.77-1.79 (1H, m), 1.51 (1H, qt, J=13.8, 3.0 Hz), 1.25 (1H, qd, J=13.8, 3.6 Hz); $^{13}$C NMR (150 MHz, $CDCl_3$) δ 141.9, 138.7, 132.3, 126.1, 125.5, 124.3, 120.8, 120.2, 119.21, 119.15, 111.7, 109.3, 75.7, 60.2, 56.0, 33.3, 28.9, 23.4; LCMS m/z 281.1851 ([M+H]$^+$, $C_{18}H_{20}N_2O$ requires 281.1648).

Second Route to Racemic Example 3 and Single Enantiomers Examples 3a and 3b

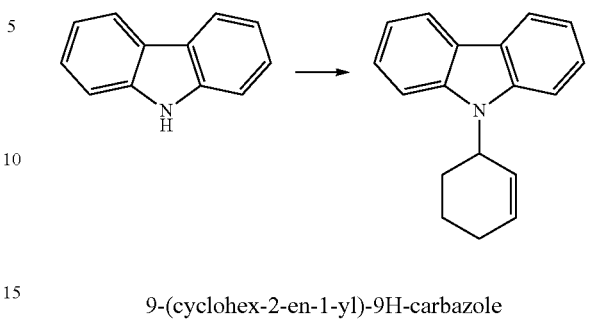

9-(cyclohex-2-en-1-yl)-9H-carbazole

A solution of carbazole (4.00 g, 23.9 mmol) in DMF (40 mL) was cooled to 0° C., treated with NaH (60% dispersion in mineral oil, 1.00 g, 25.1 mmol), stirred for 0.5 h, then treated with 3-bromo-cyclohex-1-ene (3.03 mL, 26.3 mmol). The mixture was warmed to 25° C., and stirred for 2 h. The mixture was quenched with saturated aqueous $NH_4Cl$ (100 mL). On larger scales, the mixture could be treated with $H_2O$ (100 mL), $CH_3OH$ (200 mL), and then the white solid that had formed was collected by filtration. Alternatively, the mixture was extracted with $CH_2Cl_2$-hexanes (50:50 mixture, 3×200 mL). The organic layer was washed with saturated aqueous NaCl (100 mL), dried ($Na_2SO_4$), and concentrated in vacuo. The residue was dissolved in a minimal amount of $CH_2Cl_2$ and purified by flash chromatography ($SiO_2$, 100% hexanes). The purified fractions were combined, dissolved in a minimal amount of methanol and stirred until a white solid precipitated affording the title compound as a white solid (5.41 g, 91%). $^1$H NMR (600 MHz, $CDCl_3$) δ 8.12 (2H, d, J=7.8 Hz), 7.56 (2H, d, J=7.8 Hz), 7.43 (2H, t, J=7.2 Hz), 7.23 (2H, t, J=7.2 Hz), 6.11-6.14 (1H, m), 5.94 (1H, d, J=10.2 Hz), 5.33-5.38 (1H, m), 2.33-2.36 (1H, m), 2.22-2.28 (2H, m), 2.09-2.12 (1H, m), 2.02-2.05 (1H, m), 1.89-1.92 (1H, m); $^{13}$C NMR (150 MHz, $CDCl_3$) δ 140.1, 131.0, 129.1, 125.5, 123.5, 123.4, 120.4, 118.9, 52.0, 27.7, 25.0, 22.2.

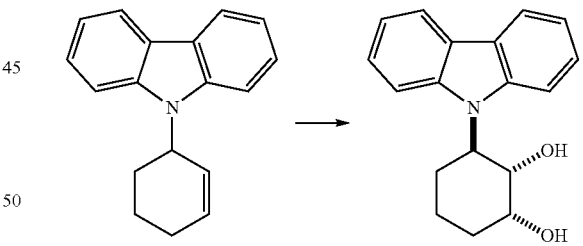

(1R,2S,3R)-rel-3-(9H-carbazol-9-yl)cyclohexane-1,2-diol

A solution of 9-(cyclohex-2-en-1-yl)-9H-carbazole (4.00 g, 16.2 mmol) in t-BuOH-$H_2O$ 5:1 (20.0 mL) at 25° C. was treated with $OsO_4$ (2.5 wt. % solution in t-BuOH, 2.02 mL, 0.162 mmol) and N-methyl morpholine N-oxide (2.08 g, 17.8 mmol). The mixture was stirred for 14 h at 25° C., treated with a saturated aqueous solution of sodium hydrosulfite (5 mL) and stirred for an additional 1 h. The mixture was concentrated in vacuo and the residue was taken up in a minimal amount of $CH_2Cl_2$ and purified by flash chromatography ($SiO_2$, 0-50% ethyl acetate-hexanes). The pure fractions were combined, concentrated in vacuo, and then resuspended in a minimal amount of ethyl acetate and precipitated with the addition of hexanes to afford the title compound as a white solid (4.86 g, 99%). $^1$H NMR (600 MHz, CDCl$_3$) δ 8.10 (2H, br s), 7.44 (2H, br s), 7.32 (1H, br s), 7.24 (3H, br s), 4.65 (1H, td, J=14.4, 4.2 Hz), 4.65 (1H, td, J=10.2 Hz), 3.75 (1H, s), 2.92 (2H, br s), 2.27 (1H, qd, J=14.4, 5.4 Hz), 1.86-1.94 (3H, m), 1.62-1.64 (1H, m), 1.43 (1H, t, J=14.4 Hz); LCMS m/z 282.1503 ([M+H$^+$], C$_{18}$H$_{19}$NO$_2$ requires 282.1489).

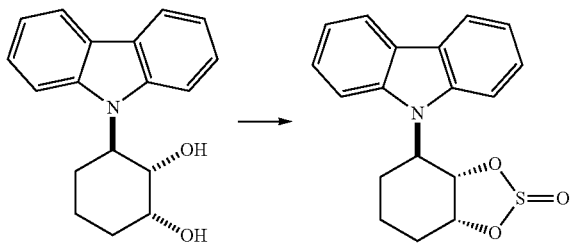

(3aS,4R,7aR)-rel-4-(9H-carbazol-9-yl)hexahydrobenzo[d][1,3,2]dioxathiole 2-oxide A solution of rac-(1R,2S,3R)-3-(9H-carbazol-9-yl)cyclohexane-1,2-diol (5.34 g, 19.0 mmol) in CH$_2$Cl$_2$ (50.0 mL) was cooled to 0° C. and treated dropwise with triethylamine (21.1 mL, 152.0 mmol), and SOCl$_2$ (slowly, over 30 minutes) (4.14 mL, 57.0 mmol). The mixture was warmed to 25° C., stirred for 2 h, poured over a solution of saturated aqueous sodium chloride (100 mL), and then extracted into CH$_2$Cl$_2$ (3×100 mL). The combined organic layers were washed with water (2×100 mL), saturated aqueous sodium chloride (100 mL), dried (Na$_2$SO$_4$), and concentrated in vacuo. The residue was dissolved in a minimal amount of CH$_2$Cl$_2$ and purified by flash chromatography (SiO$_2$, 0-10% ethyl acetate-hexanes) to afford the title compound as an orange solid (7.13 g, 99%). $^1$H NMR (600 MHz, CDCl$_3$) δ (as a mixture of sulfite diastereomers) 8.06-8.18 (2H, m), 4H[7.66 (br s), 7.33-7.47 (m), 7.23-7.27 (2H, m), 1H[5.51 (dd, J=9.6, 4.8 Hz)], 1H[5.42 (ddd, J=14.4, 9.6, 4.8 Hz), 4.50 (ddd, J=14.4, 9.6, 4.8 Hz)], 1H[5.34-5.37 (m), 4.90-4.92 (m)], 2.55-2.58 (1H, m), 2.45 (1H, qd, J=13.8, 3.6 Hz), 2.10-2.16 (1H, m), 1.98-2.08 (1H, m), 1.90-1.97 (1H, m), 1.90 (1H, qt, J=13.8, 3.6 Hz); LCMS m/z 328.0997 ([M+H$^+$], C$_{18}$H$_{17}$NO$_3$S requires 328.1002).

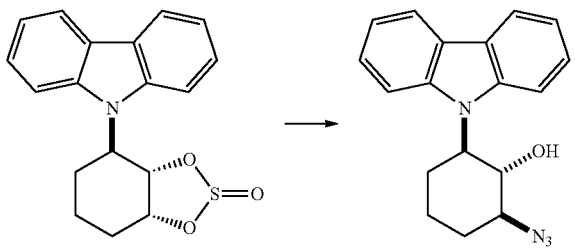

(1S,2S,6R)-rel-2-azido-6-(9H-carbazol-9-yl)cyclohexanol

A solution of rac-(3aS,4R,7aR)-4-(9H-carbazol-9-yl)hexahydrobenzo[d][1,3,2]dioxathiole 2-oxide (11.0 g, 33.6 mmol) in DMF (40.0 mL) was treated with NaN$_3$ (6.56 g, 100.8 mmol) and heated to 100° C. for 72 h. The mixture was cooled to 25° C. and partitioned between saturated aqueous NaCl (100 mL) and CH$_2$Cl$_2$ (300 mL). The organic layer was washed with saturated aqueous NaCl (3×100 mL), dried (Na$_2$SO$_4$), and concentrated in vacuo. The material could be purified by flash chromatography (SiO$_2$, 0-10% ethyl acetate-hexanes) to afford the title compound as a beige oil. $^1$H NMR (600 MHz, CDCl$_3$) δ (as a mixture of rotamers) 2H[8.13 (t, J=8.4 Hz), 8.09 (t, J=7.8 Hz)], 7.57 (1H, t, J=9.6 Hz), 7.45-7.51 (2H, m), 7.43 (1H, t, J=6.0 Hz), 2H[7.30 (t, J=7.8 Hz), 7.26-7.28 (m)], 5.32 (1H, t, J=9.6 Hz), 1H[4.64 (td, J=4.2 Hz), 4.40-4.48 (m)], 1H[3.67 (ddd, J=12.6, 9.6, 4.2 Hz), 3.53-3.57 (m)], 1H[2.60, qd, J=13.2, 3.6 Hz), 2.45 (qd, J=12.0, 3.6 Hz)], 1H[2.34-2.37 (m), 2.25 (br s)], 2.17 (1H, m), 3H[2.03-2.06 (m), 2.02 (s), 1.93-2.00 (m)], 2H[1.74 (qd, J=13.8, 3.6 Hz), 1.53-1.65 (m)]; LCMS m/z 307.1559 ([M+H$^+$], C$_{20}$H$_{24}$N$_2$O requires 307.1553).

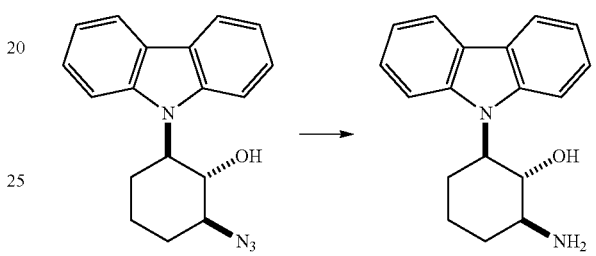

rac-(1S,2S,6R)-rel-2-amino-6-(9H-carbazol-9-yl)cyclohexanol

From the previous step, the crude residue was suspended in THF (50 mL) treated with PPh$_3$ (13.2 g, 50.4 mmol), H$_2$O (1.0 mL), and stirred for 14 h at 25° C. The mixture was concentrated in vacuo, taken up in a minimal amount of CH$_2$Cl$_2$ and purified by flash chromatography (SiO$_2$, 0-50% ethyl acetate-hexanes to remove nonpolar impurities, followed by 0-3% MeOH—CH$_2$Cl$_2$ to remove triphenylphosphine oxide, followed by 17:2:1 CH$_2$Cl$_2$:MeOH:NH$_4$OH to elute the product). The purified fractions were combined, dried azeotropically with toluene to afford the title compound as a beige solid (6.11 g, 65%). $^1$H NMR (600 MHz, CDCl$_3$) δ 8.13 (1H, d, J=7.8 Hz), 8.08 (1H, d, J=7.8 Hz), 7.58 (1H, d, J=8.4 Hz), 7.45 (1H, d, J=4.2 Hz), 7.40 (1H, t, J=7.8 Hz), 7.19-7.26 (2H, m), 7.08 (1H, t, J=6.6 Hz), 4.33-4.37 (1H, ddd, J=12.6, 9.6, 6.0 Hz), 4.03 (1H, t, J=9.6 Hz), 2.65-2.69 (1H, ddd, J=12.0, 9.0, 3.6 Hz), 2.40 (1H, qd, J=13.2, 4.2 Hz), 1.88-1.90 (1H, m), 1.84 (1H, dt, J=10.8, 3.0 Hz), 1.77-1.79 (1H, m), 1.51 (1H, qt, J=13.8, 3.0 Hz), 1.25 (1H, qd, J=13.8, 3.6 Hz); $^{13}$C NMR (150 MHz, CDCl$_3$) δ 141.9, 138.7, 132.3, 126.1, 125.5, 124.3, 120.8, 120.2, 119.21, 119.15, 111.7, 109.3, 75.7, 60.2, 56.0, 33.3, 28.9, 23.4; LCMS m/z 281.1851 ([M+H$^+$], C$_{18}$H$_{20}$N$_2$O requires 281.1648).

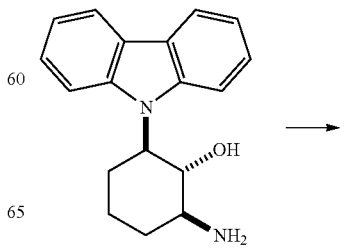

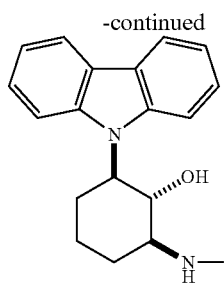

(1S,2S,3R)-rel-N-(3-(9H-carbazol-9-yl)-2-hydroxycyclohexyl)-4-(trifluoromethoxy)benzenesulfonamide A solution of rac-(1S,2S,6R)-2-amino-6-(9H-carbazol-9-yl)cyclohexanol (7.11 g, 25.4 mmol) in DMF (50.0 mL) was cooled to 0° C., treated with Et$_3$N (3.52 mL, 25.4 mmol), and 4-trifluoromethoxybenzenesulfonyl chloride (4.30 mL, 25.4 mmol). The mixture was warmed to 25° C., and stirred for 2 h. The mixture was partitioned between saturated aqueous NaCl (200 mL), and CH$_2$Cl$_2$ (300 mL). The aqueous layer was extracted with CH$_2$Cl$_2$ (3×200 mL). The combined organic layers were washed with saturated aqueous NaCl (4×200 mL), dried (Na$_2$SO$_4$), and concentrated in vacuo. The residue was dissolved in a minimal amount of CH$_2$Cl$_2$ and purified by flash chromatography (SiO$_2$, 0-25% ethyl acetate-hexanes). The purified fractions were combined, dissolved in a minimal amount of ethyl acetate, and were precipitated with the addition of hexanes to afford the title compound as a white solid (11.9 g, 88%). $^1$H NMR (600 MHz, CDCl$_3$) δ (as a mixture of rotamers) 2H[8.11 (d, J=7.2 Hz), 8.06 (d, J=7.8 Hz)], 2H[7.93 (d, J=9.0 Hz), 7.86 (d, J=9.0 Hz)], 7.52 (1H, d, J=7.8 Hz), 7.38-7.45 (2H, m), 7.36 (1H, d, J=8.4 Hz), 7.30 (1H, d, J=8.4 Hz), 7.22-7.27 (3H, m), 5.76 (1H, t, J=10.2 Hz), 1H[5.19 (d, J=4.8 Hz), 5.09 (d, J=8.4 Hz)], 2H[4.56 (td, J=12.0, 4.2 Hz), 4.29-4.38 (m)], 1H[3.60-3.66 (m), 3.23-3.27 (m)], 1H[2.49 (qd, J=13.2, 3.6 Hz), 2.41 (qd, J=11.1, 1.8 Hz)], 1H[2.24-2.25 (m), 2.19 (m)], 2H[1.97 (t, J=15.0 Hz), 1.90 (d, J=10.8 Hz)], 2H[1.59-1.66 (m), 1.47-1.55 (m)]; LCMS m/z 505.1415 ([M+H$^+$], C$_{25}$H$_{23}$F$_3$N$_2$O$_4$S requires 505.1403).

Pure Enantiomers of Example 3 were obtained from Chiralcel OD-H resolution, preparative scale eluting with 100% MeOH.

Peak 1: Example 3a

Example 3a

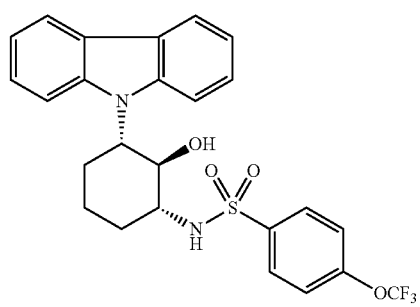

N-((1R,2R,3S)-3-(9H-carbazol-9-yl)-2-hydroxycyclohexyl)-4-(trifluoromethoxy)benzenesulfonamide N-((1R,2R,3S)-3-(9H-carbazol-9-yl)-2-hydroxycyclohexyl)-4-(trifluoromethoxy)benzenesulfonamide; $t_R$=4.4 minutes; white solid, mp. 107-109° C. (from IPA-hexanes): [α]$_D$=−7 (1.0 in CH$_2$Cl$_2$), [α]D=−5 (1.0 in CH$_3$OH).

Peak 2: Example 3b

Example 3b

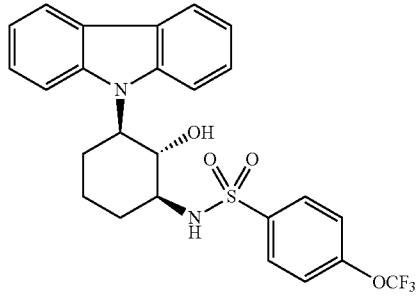

N-((1S,2S,3R)-3-(9H-carbazol-9-yl)-2-hydroxycyclohexyl)-4-(trifluoromethoxy)benzenesulfonamide N-((1S,2S,3R)-3-(9H-carbazol-9-yl)-2-hydroxycyclohexyl)-4-(trifluoromethoxy)benzenesulfonamide; $t_R$=6.7 minutes; white solid, mp. 107-109° C. (from IPA-hexanes): [α]$_D$=+7 (1.0 in CH$_2$Cl$_2$), [α]D=−5 (1.0 in CH$_3$OH).

Absolute configuration of Examples 3a and 3b may be assigned in a manner exactly analogous to that used for the phenoxazine Examples 1a and 1b, that is by stereoselective synthesis from chiral stating materials of known absolute configuration (see Scheme 4A)

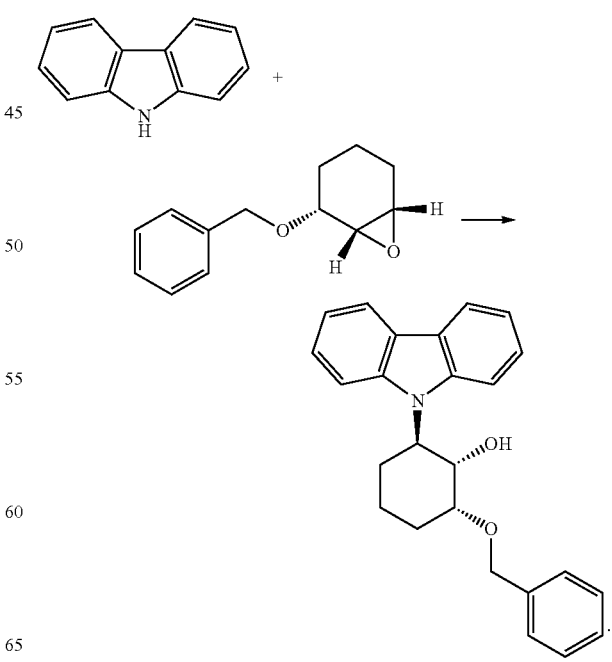

(1S,2R,6R)-2-(benzyloxy)-6-(9H-carbazol-9-yl)cyclohexanol

A solution of 9H-carbazole (0.500 g, 3.00 mmol) in toluene (8.0 mL) was treated with sodium hydride (60% dispersion in mineral oil (0.240 g, 6.00 mmol) and (1S,2R,6S)-2-(benzyloxy)-7-oxabicyclo[4.1.0]heptane (0.582 g, 2.85 mmol) at 25° C. stirred for 0.5 h. The vessel was then sealed and the mixture heated to 90° C. for 14 h. The vessel was cooled, treated with a solution of saturated ammonium chloride (50 mL), and then extracted with toluene (2×100 mL). The combined organic layers were washed with saturated aqueous NaCl (100 mL), dried (Na$_2$SO$_4$), and concentrated in vacuo. The residue was dissolved in a minimal amount of CH$_2$Cl$_2$ and purified by flash chromatography (SiO$_2$, 0-10% ethyl acetate-hexanes) to afford the title compound as a clear oil (0.371 g, 33%). $^1$H NMR (600 MHz, CDCl$_3$) δ 8.13 (2H, d, J=7.8 Hz), 7.48-7.60 (1H, br m), 7.43-7.46 (6H, m), 7.37 (2H, t, J=7.2 Hz), 7.24 (2H, d, J=7.8 Hz), 4.89 (1H, ddd, J=12.6, 11.4, 4.8 Hz), 4.80 (1H, d, J=11.4 Hz), 4.66 (1H, d, J=11.4 Hz), 4.52 (1H, ddd, J=11.4, 9.0, 3.0 Hz), 4.11-4.14 (1H, m), 2.45 (1H, qd, J=13.2, 4.2 Hz), 2.25-2.31 (1H, m), 2.16 (1H, d, J=8.4 Hz), 1.99-2.05 (1H, m), 1.94 (1H, qt, J=13.8, 3.6 Hz), 1.72-1.78 (1H, m), 1.56-1.63 (1H, m); LCMS m/z 372.2047 ([M+H$^+$], C$_{25}$H$_{25}$NO$_2$ requires 372.1958).

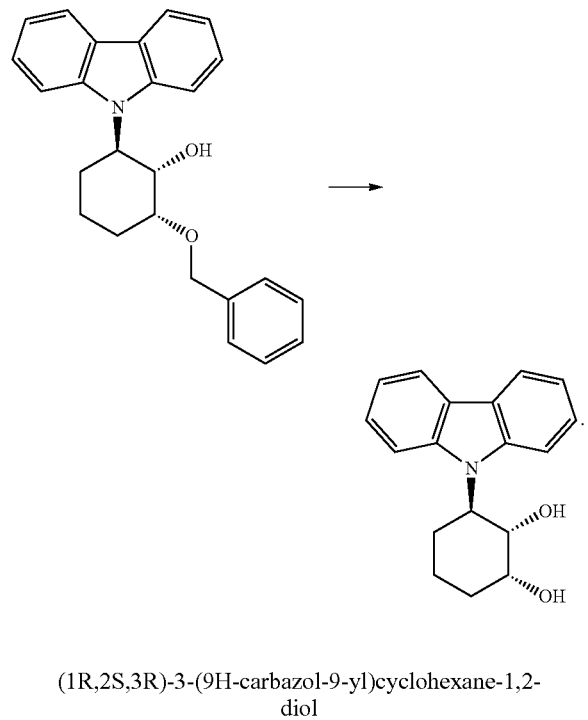

(1R,2S,3R)-3-(9H-carbazol-9-yl)cyclohexane-1,2-diol

A solution of (1S,2R,6R)-2-(benzyloxy)-6-(9H-carbazol-9-yl)cyclohexanol (0.100 g, 0.269 mmol) in THF:MeOH (1:1, 8.0 mL) was treated with 10% Pd/C (0.030 g), placed under an atmosphere of H$_2$ (g), and stirred for 6 h at 25° C. The mixture was filtered thru Celite and concentrated in vacuo to afford the title compound as a beige foam (0.035 g, 47%). [α]$_D$=+0.41 (c=1.0, CH$_2$Cl$_2$). $^1$H NMR (600 MHz, CDCl$_3$) δ 7.13 (2H, t, J=7.2 Hz), 7.10 (2H, d, J=7.2 Hz), 7.05-7.31 (2H, br s), 6.96 (2H, t, J=7.2 Hz), 4.47 (1H, ddd, J=7.8, 5.4, 3.6 Hz), 4.16 (1H, q, J=6.0 Hz), 3.98 (1H, t, J=3.6 Hz), 3.30-3.60 (2H, br s), 2.60-2.90 (2H, br s), 2.44 (1H, br s), 2.28 (1H, sextet, J=7.8 Hz), 1.93 (1H, sextet, J=6.0 Hz), 1.74 (1H, sextet, J=7.2 Hz), 1.54 (1H, sextet, J=7.8 Hz); LCMS m/z 282.1482 ([M+H$^+$], C$_{18}$H$_{20}$NO$_2$ requires 282.1489).

The optically pure diol was carried forward by the same series of conversions depicted above for Example 3 to arrive at the final product, Example 3b, N-((1S,2S,3R)-3-(9H-carbazol-9-yl)-2-hydroxycyclohexyl)-4-(trifluoromethoxy)benzenesulfonamide. Example 3b, produced from the optically active (1S,2R,6S)-2-(benzyloxy)-7-oxabicyclo[4.1.0]heptane coeluted with peak 2 by chiral analytical HPLC analysis (Chiralcel OD-H 20% IPA-Hexanes, peak 1: t$_R$=7.5 minutes, peak 2: t$_R$=25.1 minutes) and this establishes the absolute stereochemistry of Example 3b as 1S,2S,3R. In addition the absolute stereochemistry of the enantiomer, N-((1R,2R,3S)-3-(9H-carbazol-9-yl)-2-hydroxycyclohexyl)-4-(trifluoromethoxy)benzenesulfonamide, Example 3a, Peak-1 of the preparative and analytical HPLC methods is established as 1R,2R,3S.

Asymmetric synthesis of the intermediates in the syntheses of Examples 3a or 3b may be carried out in a manner exactly analogous to that for Examples 1a and 1b. Thus synthesis of (1R,2S,3R)-3-(9H-carbazol-9-yl)cyclohexane-1,2-diol is carried out as described below.

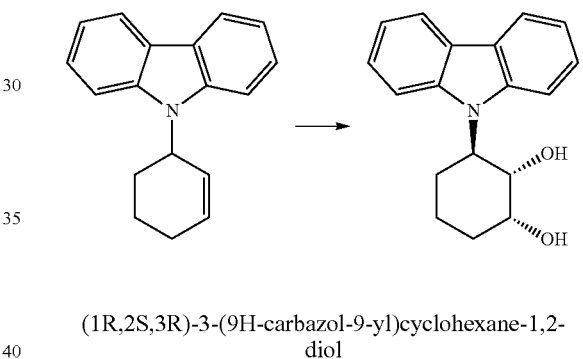

(1R,2S,3R)-3-(9H-carbazol-9-yl)cyclohexane-1,2-diol

A 20 mL Biotage® microwave reaction vial was charged with Pd$_2$.dba$_3$. CHCl$_3$ (0.052 g, 0.05 mmol), and (S,S)-DACH-phenyl Trost ligand (0.104 g, 0.15 mmol). The vial was sealed, evacuated and backfilled with argon three times. Dry degassed dichloromethane (2.5 mL) was added to this vial, and the mixture was stirred at room temperature for 30 min. Racemic tert-butyl cyclohex-2-en-1-yl carbonate (0.238 g, 1.2 mmol) was added to the vial and the contents were transferred to a separate 20 mL Biotage® microwave reaction vial containing 9H-carbazole (0.167 g, 1.00 mmol) in dry degassed dichloromethane (3.0 mL). The reaction mixture was stirred at room temperature for 10 days. At this point, the reaction mixture was evaporated onto silica gel and subjected to column chromatography (SiO$_2$; 100% hexanes) to afford pure (R)-9-(cyclohex-2-en-1-yl)-9H-carbazole (0.082 g, 33%). $^1$H NMR (600 MHz, MeOD) δ 8.05-8.04 (2H, m), 7.55 (2H, bs), 7.36 (2H, bs), 7.15 (2H, bs), 6.08 (1H, bs), 5.86 (1H, bs), 5.39 (1H, bs), 2.31-2.17 (3H, m), 1.99-1.92 (3H, m); $^{13}$C NMR (150 MHz, MeOD) δ 140.0, 130.5, 128.8, 125.1, 123.2, 119.7, 118.5, 109.9, 51.7, 27.2, 24.5, 21.8; HRMS m/z 248.1434 ([M+H$^+$], C$_{18}$H$_{18}$N requires 248.1436).

A solution of (R)-9-(cyclohex-2-en-1-yl)-9H-carbazole (0.035 g, 0.142 mmol), 4-methylmorpholine N-oxide monohydrate (0.018 g, 0.156 mmol) and osmium tetroxide (0.016 mL, 0.001 mmol, 2.5% in tert-butanol) in tert-butanol (1.00 mL) and water (0.10 mL), was stirred at RT for 60 h. The reaction mixture was treated with solid sodium bisulfite solution, stirred for 1 h, evaporated on to silica and purified by flash chromatography (SiO$_2$, 0%-70% ethyl acetate-hexanes) to afford (1R,2S,3R)-3-(9H-carbazol-9-yl)cyclohexane-1,2-diol (0.037 g, 95%). $^1$H NMR (600 MHz, MeOD) δ 8.07 (2H, d, J=6.6 Hz), 7.65-7.63 (2H, m), 7.40 (2H, d, J=7.2 Hz), 7.16 (2H, d, J=7.8 Hz), 4.55 (1H, dd, J=10.8, 3 Hz), 4.23 (1H, d, J=2.4 Hz), 2.51-2.44 (1H, m), 2.03-1.96 (2H, m), 1.88-1.77 (3H, m), 1.70-1.67 (1H, m); $^{13}$C NMR (150 MHz, MeOD) δ 125.1, 119.7, 118.3, 71.0, 70.5, 55.3, 31.1, 28.8, 19.1; LCMS m/z 282.2184 ([M+H$^+$], C$_{18}$H$_{20}$NO$_2$ requires 282.1489). Material produced in this fashion exhibited [α]$_D$=+0.43 (c=1.0, CH$_2$Cl$_2$). The enantiomeric identity and purity was also confirmed by analytical chiral HPLC>99% (CHIRALPAK® IF-3 column, 70:30 hexanes-EtOH, 1.5 mL/min, retention times: 5.2 min Alternative synthesis of (1R,2S,3R)-3-(9H-carbazol-9-yl)cyclohexane-1,2-diol:

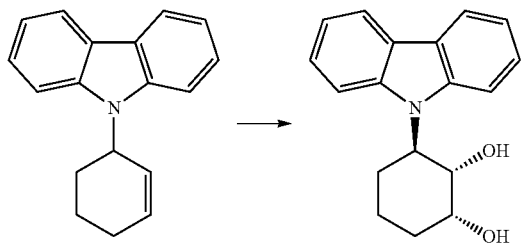 [SMILES: C1=CC(n2c3ccccc3c3ccccc32)CCC1 ; O[C@@H]1[C@H](O)CCC[C@H]1n1c2ccccc2c2ccccc21]

A solution of 9H-carbazole (0.500 g, 3.00 mmol) in toluene (8.0 mL) was treated with sodium hydride (60% wt. dispersion in mineral oil, 0.240 g, 6.00 mmol). (1S,2R,6S)-2-(benzyloxy)-7-oxabicyclo[4.1.0]heptane (0.582 g, 2.85 mmol) was added and the mixture heated to 100° C. for 24 h. The mixture was cooled to 25° C. and poured over a solution of saturated aqueous ammonium chloride (100 mL). The organic layer was separated and the aqueous layer was extracted with ethylacetate (3×100 mL). The organic layers were combined, dried (Na$_2$SO$_4$), and concentrated in vacuo. The residue was dissolved in a minimal amount of dichloromethane and purified by flash chromatography (SiO$_2$, 0%-20 ethyl acetate-hexanes) to afford (1S,2R,6R)-2-(benzyloxy)-6-(9H-carbazol-9-yl)cyclohexanol (0.125 g, 82%). $^1$H NMR (600 MHz, CDCl$_3$) δ 8.12 (1H, d, J=7.8 Hz), 7.53 (2H, bs), 7.46-7.41 (6H, m), 7.36 (1H, t, J=7.2 Hz), 7.23 (2H, t, J=7.8 Hz), 4.91-4.87 (1H, m), 4.80-4.79 (1H, m), 4.66-4.64 (1H, m), 4.53-4.49 (1H, m), 4.13-4.12 (1H, m), 2.45 (1H, ddd, J=26.4, 13.2, 4.2 Hz), 2.28-2.25 (2H, m), 2.16-2.15 (1H, m), 2.02-1.90 (2H, m), 1.75-1.73 (1H, m), 1.62-1.56 (1H, m); LCMS m/z 372.2057 ([M+H$^+$], C$_{25}$H$_{26}$NO$_2$ requires 372.1959).

A solution of (1S,2R,6R)-2-(benzyloxy)-6-(9H-carbazol-9-yl)cyclohexanol (0.100 g, 0.269 mmol) in THF:MEOH (1:1, 1.10 mL) was treated with 10% Pd/C (0.030 g, 0.029 mmol) and then placed under an atmosphere of H$_2$ (g). The mixture was stirred for 24 h at 25° C. then filtered through a celite pad, washed with hot methanol and ethylacetate, and concentrated in vacuo. The residue was dissolved in a minimal amount of dichloromethane and purified by flash chromatography (SiO$_2$, 10%-50% ethyl acetate-hexanes) to afford (1R,2S,3R)-3-(9H-carbazol-9-yl)cyclohexane-1,2-diol (0.035 g, 47%). $^1$H NMR (600 MHz, MeOD) δ 8.07 (2H, d, J=6.6 Hz), 7.65-7.62 (2H, bs), 7.39 (2H, d, J=7.2 Hz), 7.16 (2H, d, J=7.2 Hz), 4.55 (1H, dd, J=10.8, 3 Hz), 4.23 (1H, d, J=1.8 Hz), 2.51-2.44 (1H, m), 2.11-1.92 (2H, m), 1.88-1.72 (3H, m), 1.70-1.67 (1H, m); $^{13}$C NMR (150 MHz, MeOD) δ 125.1, 119.7, 118.3, 109.1, 71.0, 70.5, 55.3, 31.1, 28.8, 19.1; HRMS m/z 282.1482 ([M+H$^+$], C$_{18}$H$_{20}$NO$_2$ requires 282.1489). Material produced in this fashion exhibited [α]$_D$=+0.41 (c=1.0, CH$_2$Cl$_2$). The enantiomeric identity and purity was also confirmed by analytical chiral HPLC>99% (CHIRALPAK® IF-3 column, 70:30 hexanes-EtOH, 1.5 mL/min, retention times: 5.2 min. This confirms the absolute stereochemistry of the material arising from the catalytic process mediated by (S,S)-DACH-phenyl Trost ligand as that shown above, i.e. yielding (R)-9-(cyclohex-2-en-1-yl)-9H-carbazole in the first step to create the stereogenic center. As in Example 1 the other enantiomeric series may be accessed by the same method but employing the opposite enantiomer of the chiral ligand, i.e. (R,R)-DACH-phenyl Trost ligand in the asymmetric allylation step.

Examples 4-7

N-((1S,2S,3R)-rel-3-(9H-carbazol-9-yl)-2-hydroxycyclohexyl)-4-chlorobenzenesulfonamide Example 4. A solution of (1R,2S,6R)-rel-2-amino-6-(9H-carbazol-9-yl)cyclohexanol (0.059 g, 0.210 mmol) in DMF (1.0 mL) was cooled to 0° C., treated with Et$_3$N (29.0 μL, 0.210 mmol), and 4-chlorobenzenesulfonyl chloride (0.044 g, 0.210 mmol). The mixture was warmed to 25° C. and stirred for 2 h. The mixture was partitioned between saturated aqueous NaCl (50 mL), and CH$_2$Cl$_2$ (100 mL). The organic layer was washed with saturated aqueous NaCl (3×50 mL), dried (Na$_2$SO$_4$), and concentrated in vacuo. The residue was dissolved in a minimal amount of CH$_2$Cl$_2$ and purified by flash chromatography (SiO$_2$, 0-20% ethyl acetate-hexanes). The purified fractions were combined, dissolved in a minimal amount of ethyl acetate, and were precipitated with the addition of hexanes to afford Example 4 as a white solid (0.500 g, 52%). $^1$H NMR (600 MHz, CDCl$_3$) δ (as a mixture of rotamers) 8.11 (1H, dd, J=2.4 Hz), 8.06 (1H, d, J=7.8 Hz), 7.83 (2H, d, J=8.4 Hz), 7.51 (1H, d, J=8.4 Hz), 7.46 (2H, d, J=6.6 Hz), 7.42 (2H, t, J=7.8 Hz), 7.37-7.40 (1H, m), 7.24 (2H, dt, J=15.0, 7.2 Hz), 5.14 (1H, d, J=3.6 Hz), 4.29-4.37 (2H, m), 3.20-3.25 (1H, m), 2.38-2.45 (1H, m), 2.23-2.27 (1H, m), 2.09 (1H, br s), 1.89-1.92 (2H, m), 1.48-1.54 (2H, m); $^{13}$C NMR (600 MHz, CDCl$_3$) δ 141.6, 138.3, 129.6, 128.9, 126.2, 125.7, 120.1, 119.7, 111.4, 109.1, 73.0, 60.1, 59.0, 31.7, 28.3, 22.9; LCMS m/z 455.1202 ([M+H$^+$], C$_{24}$H$_{23}$C$_1$N$_2$O$_3$S requires 455.1191).

N-((1S,2S,3R)-rel-3-(9H-carbazol-9-yl)-2-hydroxycyclohexyl)-4-cyanobenzenesulfonamide Example 5. A solution of (1R,2S,6R)-rel-2-amino-6-(9H-carbazol-9-yl)cyclohexanol (0.078 g, 0.276 mmol) in DMF (1.0 mL) was cooled to 0° C., treated with Et$_3$N (38 0.276 mmol), and 4-cyanobenzenesulfonyl chloride (0.056 g, 0.276 mmol). The mixture was warmed to 25° C. and stirred for 2 h. The mixture was partitioned between saturated aqueous NaCl (50 mL), and CH$_2$Cl$_2$ (100 mL). The organic layer was washed with saturated aqueous NaCl (3×50 mL), dried (Na$_2$SO$_4$), and concentrated in vacuo. The residue was dissolved in a minimal amount of CH$_2$Cl$_2$ and purified by flash chromatography (SiO$_2$, 0-20% ethyl acetate-hexanes). The purified fractions were combined, dissolved in a minimal amount of ethyl ether, and were precipitated with the addition of hexanes to afford Example 5 as a white solid (0.0434 g, 35%). $^1$H NMR (600 MHz, CDCl$_3$) δ (as a mixture of rotamers) 8.11 (1H, d, J=7.8 Hz), 8.05 (1H, d, J=7.2 Hz), 2H[7.91 (d, J=8.4 Hz), 7.87 (d, J=8.4 Hz)], 7.69 (2H, d, J=8.4 Hz), 7.51 (1H, d, J=8.4 Hz), 2H[7.44 (t, J=7.2 Hz), 7.40 (t, J=7.8 Hz)], 1H[7.36 (d, J=8.4 Hz), 7.33 (d, J=8.4 Hz), 7.24 (2H, dt, J=20.4, 7.2 Hz), 5.73 (1H, t, J=10.2 Hz), 1H[5.29 (d, J=9.0 Hz), 5.19 (d, J=6.0 Hz)], 1H[4.55 (ddd, J=13.8, 12.6, 4.2 Hz), 4.31 (ddd, J=13.8, 10.2, 4.2 Hz)], 4.24 (1H, t, J=9.6 Hz), 1H[3.56-3.65 (m), 3.21-3.28 (m)], 1H[2.48-2.51 (m), 2.35-2.42 (m)], 2.16-2.20 (2H, m), 1.86-1.90 (2H, m), 1.47 (2H, t, J=10.8 Hz); $^{13}$C NMR (600 MHz, CDCl$_3$) δ 145.1, 141.6, 138.3, 133.0, 127.9, 127.7, 126.3, 125.6, 124.6, 122.9, 121.0, 120.4, 119.7, 117.6, 116.4, 111.4, 109.1, 72.9, 60.1, 59.1, 32.1, 28.5, 22.9; LCMS m/z 446.1546 ([M+H$^+$], C$_{25}$H$_{23}$N$_3$O$_3$S requires 446.1533).

N-((1S,2S,3R)-rel-3-(9H-carbazol-9-yl)-2-hydroxycyclohexyl)-4-methoxybenzenesulfonamide Example 6. A solution of (1R,2S,6R)-rel-2-amino-6-(9H-carbazol-9-yl)cyclohexanol (0.0786 g, 0.280 mmol) in DMF (1.0 mL) was cooled to 0° C., treated with Et$_3$N (39.0 μL, 0.280 mmol), and 4-methoxybenzenesulfonyl chloride (0.0580 g, 0.280 mmol). The mixture was warmed to 25° C., and stirred for 2 h. The mixture was partitioned between saturated aqueous NaCl (50 mL), and CH$_2$Cl$_2$ (100 mL). The organic layer was washed with saturated aqueous NaC; (3×50 mL), dried (Na$_2$SO$_4$), and concentrated in vacuo. The residue was dissolved in a minimal amount of CH$_2$Cl$_2$ and purified by flash chromatography (SiO$_2$, 0-20% ethyl acetate-hexanes). The purified fractions were combined, dissolved in a minimal amount of ethyl acetate, and were precipitated with the addition of hexanes to afford Example 6 as a white solid (0.0521 g, 41%). $^1$H NMR (600 MHz, CDCl$_3$) δ (as a mixture of rotamers) 8.11 (1H, d, J=7.2 Hz), 8.04 (1H, d, J=7.8 Hz), 7.81 (2H, dd, J=7.2, 1.8 Hz), 7.52 (1H, d, J=8.4 Hz), 7.38 (2H, t, J=6.6 Hz), 7.34 (1H, t, J=8.4 Hz), 7.21 (2H, dt, J=13.2, 7.8 Hz), 6.91 (2H, d, J=9.0 Hz), 5.36 (1H, d, J=6.0 Hz), 4.28-4.34 (2H, m), 3.82 (3H, s), 3.15-3.20 (1H, m), 2.49 (1H, br s), 2.36 (1H, qd, J=13.2, 3.6 Hz), 2.05-2.09 (1H, m), 1.82 (2H, t, J=12.6 Hz), 1.40-1.50 (2H, m); $^{13}$C NMR (600 MHz, CDCl$_3$) δ 163.0, 141.6, 138.4, 132.1, 129.5, 126.0, 125.5, 124.4, 122.8, 120.8, 120.2, 119.34, 119.27, 117.6, 114.4, 111.5, 109.2, 72.9, 59.8, 59.0, 55.7, 31.5, 28.4, 23.0; LCMS m/z 451.1887 ([M+H$^+$], C$_{25}$H$_{26}$N$_2$O$_4$S requires 451.1686).

N-((1S,2S,3R)-rel-3-(9H-carbazol-9-yl)-2-hydroxycyclohexyl) benzenesulfonamide Example 7. A solution of (1R,2S,6R)-rel-2-amino-6-(9H-carbazol-9-yl)cyclohexanol (0.0791 g, 0.282 mmol) in DMF (1.0 mL) was cooled to 0° C., treated with Et$_3$N (39.0 0.282 mmol), and benzenesulfonyl chloride (36.0 μL, 0.282 mmol). The mixture was warmed to 25° C., and stirred for 2 h. The mixture was partitioned between saturated aqueous NaCl (50 mL), and CH$_2$Cl$_2$ (100 mL). The organic layer was washed with saturated aqueous NaCl (3×50 mL), dried (Na$_2$SO$_4$), and concentrated in vacuo. The residue was dissolved in a minimal amount of CH$_2$Cl$_2$ and purified by flash chromatography (SiO$_2$, 0-20% ethyl acetate-hexanes) to afford Example 7 as a white solid (0.0454 g, 38%). $^1$H NMR (600 MHz, CDCl$_3$) δ (as a mixture of rotamers) 8.11 (1H, d, J=7.8 Hz), 8.05 (1H, q, J=5.4 Hz), 2H[7.92 (d, J=7.8 Hz), 7.83 (d, J=7.2 Hz)], 7.56 (1H, q, J=7.2 Hz), 7.49-7.53 (3H, m), 7.43 (1H, t, J=7.8 Hz), 7.37-7.41 (1H, m), 7.36 (1H, t, J=7.8 Hz), 7.22 (2H, dt, J=12.6, 7.8 Hz), 5.77 (1H, t, J=10.2 Hz), 1H[5.30 (d, J=4.8 Hz), 5.13 (d, J=9.0 Hz)], 2H[4.56 (td, J=12.6, 4.2 Hz), 4.29-4.37 (m)], 1H[3.60-3.66 (m), 3.22-3.26 (m)], 1H[2.48 (qd, J=13.2, 3.6 Hz), 2.41 (qd, J=12.6, 3.6 Hz)], 2.29 (1H, br s), 2.15-2.18 (1H, br s), 2H[1.91-1.96 (m), 1.84-1.87 (m)], 2H[(1.54-1.63 (m), 1.42-1.52 (m)]; $^{13}$C NMR (600 MHz, CDCl$_3$) δ 141.6, 140.6, 138.4, 132.9, 129.3, 127.3, 127.1, 126.1, 125.6, 124.5, 122.9, 120.9, 120.3, 119.5, 111.5, 109.2, 73.0, 59.9, 59.1, 31.6, 28.4, 22.9; LCMS m/z 421.1618 ([M+H$^+$], C$_{24}$H$_{24}$N$_2$O$_3$S requires 421.1580).

Examples 8 and 9

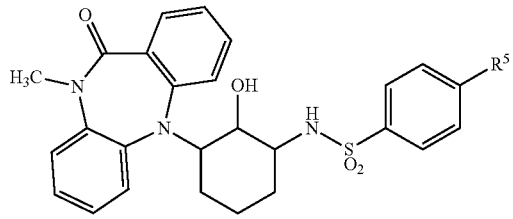

R$^5$=OCF$_3$ (Ex. 8), R$^5$=Cl (Ex. 9)

10-Methyl-5H-dibenzo[b,e][1,4]diazepin-11(10H)-one. A solution of 5H-dibenzo[b,e][1,4]diazepin-11(10H)-one (1.00 g, 4.76 mmol) in DMF (5.0 mL) was cooled to 0° C. and treated with NaH (60% dispersion in mineral oil, 0.200 g, 5.00 mmol) and methyl iodide (0.33 mL, 5.24 mmol). The solution was warmed to 25° C. and stirred for 14 h. The mixture was poured over saturated aqueous NaCl (100 mL) and extracted with CH$_2$Cl$_2$ (3×100 mL). The combined organic layers were washed with saturated aqueous NaCl (3×100 mL), dried (Na$_2$SO$_4$), concentrated in vacuo, and the residue was purified by flash chromatography (SiO$_2$, 0-20% ethyl acetate-hexanes) to afford the title compound as a white solid (0.886 g, 83%). $^1$H NMR (600 MHz, CDCl$_3$) δ 7.90 (1H, dd, J=7.8, 1.8 Hz), 7.30 (1H, td, J=7.8, 1.8 Hz), 7.19 (1H, dd, J=7.8, 1.2 Hz), 7.11 (1H, td, J=7.2, 1.8 Hz), 7.07 (1H, td, J=7.8, 1.8 Hz), 7.02 (1H, td, J=7.8, 1.2 Hz), 6.92 (1H, dd, J=7.8, 1.2 Hz), 6.81 (1H, d, J=8.4 Hz), 5.46 (1H, s), 3.55 (3H, s); $^{13}$C NMR (150 MHz, CDCl$_3$) δ 168.8, 150.8, 143.4, 135.8, 133.1, 132.7, 125.9, 125.0, 124.5, 123.4, 122.8, 120.4, 118.7, 38.3; LCMS m/z 225.1040 ([M+H$^+$], C$_{14}$H$_{12}$N$_2$O requires 225.1022).

Rac-5-(cyclohex-2-en-1-yl)-10-methyl-5H-dibenzo [b,e][1,4]diazepin-11(10H)-one. A solution of 10-methyl-5H-dibenzo [b,e][1,4]diazepin-11(10H)-one (0.622 g, 2.77 mmol) in CHCl$_3$ (5.0 mL) was treated with Et$_3$N (1.15 g, 8.32 mmol) and 3-bromocyclohex-1-ene (0.38 mL, 3.32 mmol). The solution was warmed to 50° C. and stirred for 2 h. The mixture was concentrated in vacuo, taken up in a minimal amount of CH$_2$Cl$_2$ and purified by flash chromatography (SiO$_2$, 0-20% ethyl acetate-hexanes) to afford the title compound as a clear foam (0.836 g, 99%). $^1$H NMR (600 MHz, CDCl$_3$) δ (as a mixture of conformers) 1H[7.78 (d, J=6.6 Hz), 7.62 (td, J=6.0, 1.2 Hz)], 7.19-7.25 (1H, m), 7.04-7.12 (2H, m), 6.98-7.03 (2H, m), 6.93-6.97 (1H, m), 1H[6.86-6.89 (m), 6.75 (d, J=7.8 Hz)], 1H[5.91-5.94 (m), 5.89-5.90 (m)], 1H[5.68-5.69 (m), 5.63-5.64 (m)], 4.45 (1H, br s), 3H[ 3.47 (s), 3.45 (s)], 1.90 (2H, br s), 1.80-1.84 (1H, m), 1.67-1.70 (1H, m), 1.48-1.65 (1H, m), 1.43-1.48 (1H, m); LCMS m/z 305.1690 ([M+H$^+$], C$_{20}$H$_{20}$N$_2$O requires 305.1648).

5-((1R,2S,3R)-rel-2,3-dihydroxycyclohexyl)-10-methyl-5H-dibenzo[b,e][1,4]diazepin-11(10H)-one. A solution of rac-5-(cyclohex-2-en-1-yl)-10-methyl-5H-dibenzo[b,e][1,4]diazepin-11(10H)-one (0.826 g, 2.71 mmol) in t-BuOH-H$_2$O 5:1 (5.0 mL) at 25° C. was treated with OsO$_4$ (2.5 wt. % solution in t-BuOH, 0.34 mL, 0.027 mmol) and N-methyl morpholine N-oxide monohydrate (0.403 g, 2.98 mmol). The mixture was stirred for 14 h at 25° C., treated with a saturated aqueous solution of sodium hydrosulfite (5 mL) and stirred for an additional 1 h. The mixture was concentrated in vacuo and the residue was taken up in a minimal amount of $CH_2Cl_2$ and purified by flash chromatography ($SiO_2$, 0-50% ethyl acetate-hexanes) to afford the title compound as a clear film (0.754 g, 82%). $^1$H NMR (600 MHz, $CDCl_3$) δ (as a mixture of conformers) 1H[7.74 (t, J=1.8 Hz), 7.72 (t, J=1.8 Hz)], 7.37 (1H, tt, J=7.8, 1.8 Hz), 7.30 (1H, dd, J=7.8, 1.8 Hz), 7.22-7.25 (2H, m), 7.12-7.15 (3H, m), 7.10 (1H, t, J=6.6 Hz), 4.21 (1H, br s), 2H[3.94-3.95 (m), 3.89-3.91 (m), 3.82-3.87 (m)], 3H[3.58 (s), 3.57 (s)], 2.08-2.11 (1H, m), 1.91-1.93 (1H, m), 1.83-1.86 (1H, m), 1.69-1.74 (1H, m), 1.65-1.69 (1H, m), 1.43-1.46 (1H, m); LCMS m/z 339.1747 ([M+H$^+$], $C_{20}H_{22}N_2O_3$ requires 339.1703).

(1R,2S,3R)-rel-2-hydroxy-3-(10-methyl-11-oxo-10,11-dihydro-5H-dibenzo[b,e][1,4]diazepin-5-yl)cyclohexyl methanesulfonate. A solution of 5-((1R,2S,3R)-rel-2,3-dihydroxycyclohexyl)-10-methyl-5H-dibenzo[b,e][1,4]diazepin-11(10H)-one (0.734 g, 2.17 mmol) in pyridine (5.0 mL) was cooled to 0° C. and treated dropwise with methanesulfonyl chloride (168 μL, 2.17 mmol). The mixture was warmed to 25° C., stirred for 3 h, and then concentrated in vacuo. The residue was suspended in $CH_2Cl_2$ (200 mL) and the organic phase was washed with 1 M HCl (3×100 mL), dried ($Na_2SO_4$), and concentrated in vacuo. The residue was dissolved in a minimal amount of $CH_2Cl_2$ and purified by flash chromatography ($SiO_2$, 0-50% ethyl acetate-hexanes) to afford the title compound as a white solid (0.761 g, 84%). $^1$H NMR (600 MHz, $CDCl_3$) δ (as a mixture of conformers) 1H[7.77 (dd, J=7.8, 1.2 Hz), 7.73 (dd, J=7.8, 1.2 Hz)], 1H[(7.42 (td, J=9.0, 1.2 Hz), 7.38 (td, J=7.8, 1.2 Hz)], 7.25-7.30 (2H, m), 7.18-7.34 (2H, m), 7.12-7.17 (2H, m), 4.80-4.84 (1H, m), 2H[4.31-4.34 (m), 4.22 (br s), 4.07 (br s)], 3H[3.65 (s), 3.60 (s)], 3H[2.89 (s), 2.82 (s)], 2.14-2.16 (1H, m), 2.00-2.08 (1H, m), 1.89-1.98 (1H, m), 1.85-1.89 (1H, m), 1.69-1.76 (1H, m), 1.55-1.62 (1H, m), 1.44-1.48 (1H, m); LCMS m/z 417.1498 ([M+H$^+$], $C_{21}H_{24}N_2O_5S$ requires 417.1479).

5-((1R,2S,3S)-rel-3-azido-2-hydroxycyclohexyl)-10-methyl-5H-dibenzo[b,e][1,4]diazepin-11(10H)-one. A solution of (1R,2S,3R)-rel-2-hydroxy-3-(10-methyl-11-oxo-10,11-dihydro-5H-dibenzo[b,e][1,4]diazepin-5-yl)cyclohexyl methanesulfonate (0.614 g, 1.47 mmol) in DMF (3.0 mL) was treated with $NaN_3$ (0.144 g, 2.21 mmol) and heated to 100° C. for 2 h under microwave radiation. The mixture was cooled to 25° C. and partitioned between saturated aqueous NaCl (100 mL) and $CH_2Cl_2$ (300 mL). The organic layer was washed with saturated aqueous NaCl (3×100 mL), dried ($Na_2SO_4$), and concentrated in vacuo. The residue was dissolved in a minimal amount of $CH_2Cl_2$ and purified by flash chromatography ($SiO_2$, 0-20% ethyl acetate-hexanes) to afford the title compound as a white solid (0.444 g, 83%). $^1$H NMR (600 MHz, $CDCl_3$) 1H[7.85 (dd, J=7.8, 1.2 Hz), 7.81 (dd, J=7.8, 1.8 Hz), 7.40 (1H, tt, J=7.8, 1.8 Hz), 2H[7.37 (d, J=7.8 Hz), (t, J=7.8 Hz)], 7.24-7.26 (2H, m), 7.14-7.21 (2H, m), 3H[3.57 (s), 3.54 (s)], 3.42-3.45 (1H, m), 3.33-3.38 (1H, m), 3.31-3.32 (1H, m), 2.23-2.25 (0.5H, m), 1.95-2.01 (2H, m), 1.83 (0.5H, doublet of quintets, J=10.2, 3.6 Hz), 1H[1.75 (br s), 1.70-1.75 (m)], 1.67 (0.5H, qd, J=12.6, 4.2 Hz)], 1.37 (0.5H, qt, J=13.2, 3.6 Hz), 1.24-1.30 (2H, m); LCMS m/z 364.1814 ([M+H$^+$], $C_{20}H_{21}N_5O_2$ requires 364.1768).

5-((1R,2R,3S)-rel-3-amino-2-hydroxycyclohexyl)-10-methyl-5H-dibenzo[b,e][1,4]diazepin-11(10H)-one. A solution of 5-((1R,2S,3S)-rel-3-azido-2-hydroxycyclohexyl)-10-methyl-5H-dibenzo[b,e][1,4]diazepin-11(10H)-one (0.424 g, 1.17 mmol) in THF (5 mL) was treated with $PPh_3$ (0.337 g, 1.28 mmol), $H_2O$ (0.3 mL), and stirred for 14 h at 25° C. The mixture was concentrated in vacuo, taken up in a minimal amount of $CH_2Cl_2$ and purified by flash chromatography ($SiO_2$, 0-50% ethyl acetate-hexanes to remove nonpolar impurities, followed by 0-3% MeOH—$CH_2Cl_2$ to remove triphenylphosphine oxide, followed by 17:2:1 $CH_2Cl_2$:MeOH:$NH_4OH$ to elute the product). The purified fractions were combined, dried azeotropically with toluene to afford the title compound as a clear film (0.393 g, 99%). $^1$H NMR (600 MHz, $CDCl_3$) δ 1H[7.83 (dd, J=7.8, 1.8 Hz), 7.78 (d, J=8.4 Hz)], 7.37-7.41 (2H, m), 7.22-7.25 (1H, m), 7.20-7.22 (2H, m), 2H[7.15-7.19 (m), 7.11-7.15 (m)], 3H[3.56 (s), 3.54 (s)], 1H[3.40-3.45 (m), 3.35-3.39 (m)], 1H[3.20 (t, J=9.6 Hz), 3.06 (t, J=9.0 Hz)], 2.61-2.66 (1H, m), 2H[2.23-2.26 (m), 1.99 (m)], 1.76-1.83 (2H, m), 1.67-1.74 (1H, m), 1.63 (1H, dt, J=13.8, 3.0 Hz), 1.25-1.38 (2H, m), 1.08 (1H, sextet of d, J=13.2, 3.6 Hz); LCMS m/z 338.2148 ([M+H$^+$], $C_{20}H_{23}N_3O_2$ requires 338.1863).

4-Trifluoromethoxy-N-((1S,2S,3R)-rel-2-hydroxy-3-(10-methyl-11-oxo-10,11-dihydro-5H-dibenzo[b,e][1,4]diazepin-5-yl)cyclohexyl)benzenesulfonamide Example 8. A solution of 5-((1R,2R,3S)-rel-3-amino-2-hydroxy cyclohexyl)-10-methyl-5H-dibenzo[b,e][1,4]diazepin-11(10H)-one (0.0800 g, 0.238 mmol) in DMF (1.0 mL) was cooled to 0° C., treated with $Et_3N$ (33.0 μL, 0.238 mmol), and 4-trifluoromethoxybenzenesulfonyl chloride (40.0 μL, 0.238 mmol). The mixture was warmed to 25° C., and stirred for 2 h. The mixture was partitioned between saturated aqueous NaCl (50 mL), and $CH_2Cl_2$ (100 mL). The organic layer was washed with saturated aqueous NaCl (3×50 mL), dried ($Na_2SO_4$), and concentrated in vacuo. The residue was dissolved in a minimal amount of $CH_2Cl_2$ and purified by flash chromatography ($SiO_2$, 0-50% ethyl acetate-hexanes). The purified fractions were combined, dissolved in a minimal amount of ethyl acetate, and precipitated with the addition of hexanes to afford Example 8 as a white solid (0.100 g, 75%); $^1$H NMR (600 MHz, $CDCl_3$) δ 7.94 (2H, t, J=7.2 Hz), 7.76 (1H, dd, J=7.8, 1.8 Hz), 7.38 (1H, td, J=7.8, 1.8 Hz), 7.33 (2H, d, J=8.4 Hz), 7.28 (2H, d, J=7.2 Hz), 7.23-7.24 (2H, m), 7.12-7.16 (2H, m), 5.27 (1H, d, J=6.6 Hz), 3.53 (3H, s), 3.35-3.37 (2H, m), 3.34 (1H, s), 3.08-3.10 (1H, m), 1.99-2.01 (1H, m), 1.83-1.85 (1H, m), 1.60-1.63 (1H, m), 1.32-1.38 (1H, m), 1.12-1.18 (2H, m); LCMS m/z 562.1625 ([M+H$^+$], $C_{27}H_{26}F_3N_3O_5S$ requires 562.1618).

4-Chloro-N-((1S,2S,3R)-rel-2-hydroxy-3-(10-methyl-11-oxo-10,11-dihydro-5H-dibenzo[b,e][1,4]diazepin-5-yl)cyclohexyl)benzenesulfonamide Example 9. A solution of 5-((1R,2R,3S)-rel-3-amino-2-hydroxycyclohexyl)-10-methyl-5H-dibenzo[b,e][1,4]diazepin-11(10H)-one (0.0800 g, 0.238 mmol) in DMF (1.0 mL) was cooled to 0° C., treated with $Et_3N$ (33.0 μL, 0.238 mmol), and 4-chlorobenzenesulfonyl chloride (0.050 g, 0.238 mmol). The mixture was warmed to 25° C. and stirred for 2 h. The mixture was partitioned between saturated aqueous NaCl (50 mL), and $CH_2Cl_2$ (100 mL). The organic layer was washed with saturated aqueous NaCl (3×50 mL), dried ($Na_2SO_4$), and concentrated in vacuo. The residue was dissolved in a minimal amount of $CH_2Cl_2$ and purified by flash chromatography ($SiO_2$, 0-50% ethyl acetate-hexanes). The purified fractions were combined, dissolved in a minimal amount of ethyl acetate, and precipitated with the addition of hexanes to afford Example 9 as a white solid (0.0958 g, 79%). $^1$H NMR (600 MHz, $CDCl_3$) δ 2H[7.81 (d, J=8.4 Hz), 7.78 (d, J=7.2 Hz)], 2H[7.47 (d, J=8.4 Hz), 7.44 (d, J=8.4 Hz)], 7.33-7.38 (1H, m), 7.30-7.33 (2H, m) 7.21-7.23 (2H, m), 7.11-7.14 (2H, m), 1H[5.39 (d, J=6.6 Hz), 5.32 (d, J=4.8

Hz)], 3.52 (3H, s), 2H[3.41 (s), 3.35-3.37 (m), 3.29 (s), 3.19 (t, J=9.6 Hz)], 1H[3.03-3.08 (m), 2.95 (septet, J=4.8 Hz)], 1H[2.20-2.22 (m), 1.98 (m)], 2H[1.75-1.79 (m), 1.65-1.70 (m), 1.56-1.60 (m)], 1.29-1.34 (1H, m), 1.13-1.17 (2H, m); LCMS m/z 512.1409 ([M+H$^+$], $C_{26}H_{26}ClN_3O_4S$ requires 512.1405).

Example 10

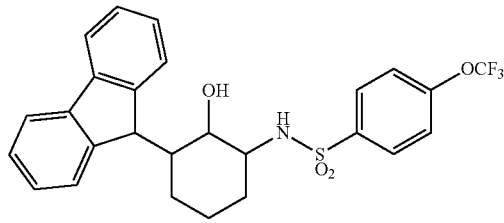 [SMILES: O=S(=O)(NC1CCCC(C2c3ccccc3-c3ccccc32)C1O)c1ccc(OC(F)(F)F)cc1]

The synthesis is begun by a palladium-catalyzed C-allylation of commercially available 9H-fluorene 1 with cyclohex-2-en-1-yl acetate to afford alkene (*Zhurnal Organicheskoi Khimii*, 1986, 22(7), 1565-6). An osmium tetroxide catalyzed dihydroxylation will afford diol. Treatment of diol with methanesulfonyl choride will furnish mesylate. A sodium azide induced azide displacement will afforded azide. The amine may be synthesized via a Staudinger reaction. Treating the amine with commercially available 4-(trifluoromethoxy)benzene-1-sulfonyl chloride will afford target sulfonamide Example 10.

Examples 12, 13 and 14 may be synthesized by the route shown in Scheme 6:

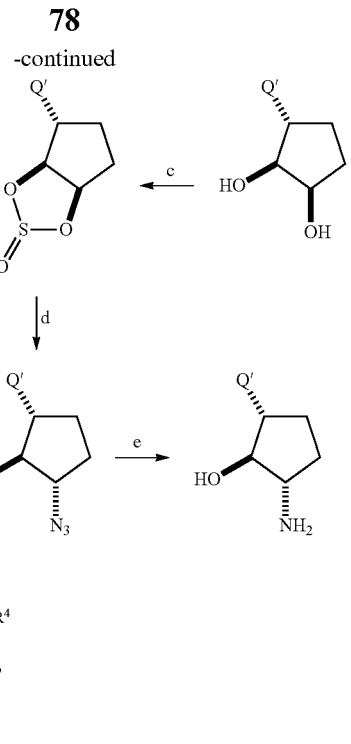

a: The protected diastereomeric epoxide is reacted with the nitrogen tricycle in the presence of a strong base, such as NaH. The protecting group may be, for example, benzyl or t-butyldimethylsilyl.
b: The protecting group is removed with an appropriate reagent, e.g. catalytic hydrogenation for benzyl or tetrabutylammonium fluoride for t-butyldimethylsilyl.
c: The diol is treated with thionyl chloride in the presence of a base, such as triethylamine.
d: The sulfite ester is ring-opened with an azide, such as sodium azide.
e: The azide is reduced to the amine with phosphine, such as triphenylphosphine.
f: (not shown) The amine is acylated as described in many examples above with the appropriate phenylsulfonyl choloride.

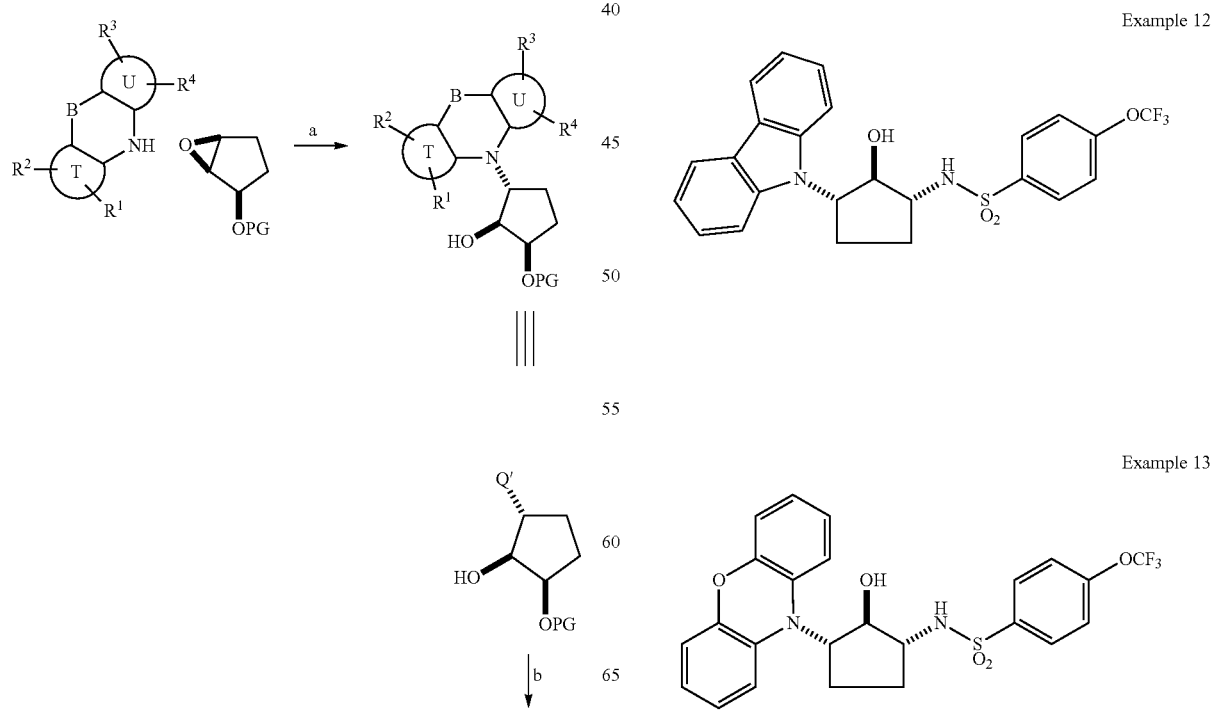

Example 14

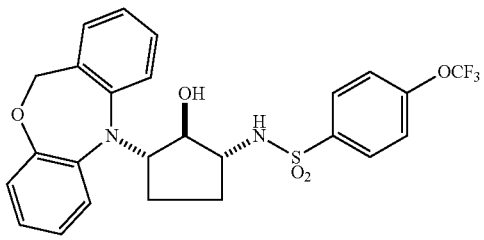

Example 15 is synthesized in a fashion analogous to that shown above in Example 10 by a palladium-catalyzed C-allylation with cyclopent-2-en-1-yl acetate.

Example 15

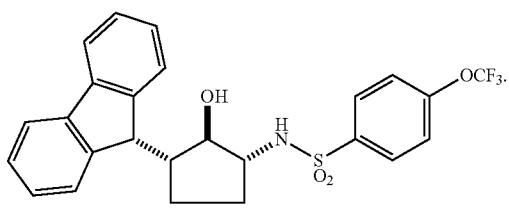

Chiral materials. Method analogous to stereoselective synthesis of 3-optically active staring materials

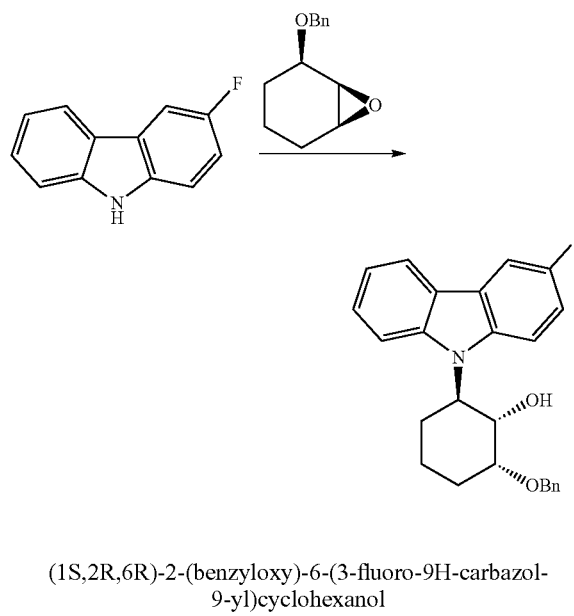

(1S,2R,6R)-2-(benzyloxy)-6-(3-fluoro-9H-carbazol-9-yl)cyclohexanol

A solution of 3-fluoro-9H-carbazole (1.00 g, 5.40 mmol) in toluene (10 mL) at 0° C. was treated with NaH (60% dispersion in mineral oil (0.431 g, 10.8 mmol), and (1S,2R,6S)-2-(benzyloxy)-7-oxabicyclo[4.1.0]heptane (1.10 g, 5.40 mmol). The mixture was warmed to 100° C. and stirred for 14 h. The mixture was cooled to 25° C., treated with saturated aqueous NH$_4$Cl (50 mL), and extracted with toluene (3×50 mL). The organic layer was washed with saturated aqueous NaCl (3×50 mL), dried (Na$_2$SO$_4$), and concentrated in vacuo. The residue was dissolved in a minimal amount of toluene and purified by flash chromatography (SiO$_2$, 0-10% ethyl acetate-hexanes) to afford the title compound as a beige foam (1.38 g, 66%) and minor amount of the other regioisomer (0.229 g, 11%). $^1$H NMR (600 MHz, CDCl$_3$) δ 8.05 (1H, d, J=7.2 Hz), 7.75 (1H, d, J=7.2 Hz), 7.41-7.47 (7H, m), 7.36 (1H, tt, J=6.0, 1.8 Hz), 7.22 (1H, t, J=7.8 Hz), 7.17 (1H, t, J=8.4 Hz), 4.80-4.84 (1H, m), 4.79 (1H, d, J=12.0 Hz), 4.61 (1H, d, J=11.4 Hz), 4.43-4.48 (1H, m), 4.11-4.13 (1H, m), 2.37-2.44 (1H, m), 2.28 (1H, doublet of quintets, J=14.4, 3.0 Hz), 2.18 (1H, d, J=9.6 Hz), 1.98-2.03 (1H, m), 1.91 (1H, qt, J=13.8, 3.6 Hz), 1.73-1.76 (1H, m), 1.55-1.61 (1H, m); LCMS m/z 390.1855 ([M+H$^+$], C$_{25}$H$_{24}$FNO$_2$ requires 390.1864).

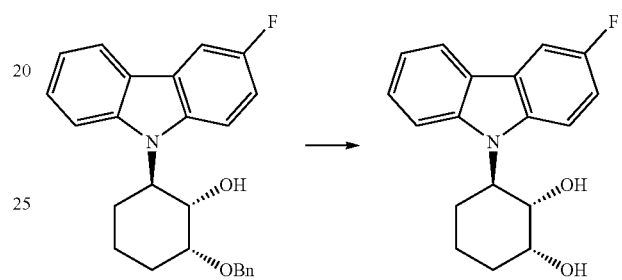

(1R,2S,3R)-3-(3-fluoro-9H-carbazol-9-yl)cyclohexane-1,2-diol

A solution of (1S,2R,6R)-2-(benzyloxy)-6-(3-fluoro-9H-carbazol-9-yl)cyclohexanol (1.36 g, 3.49 mmol) in THF:MeOH (1:1, 10.0 mL) was treated with 10% Pd/C (0.370 g), placed under an atmosphere of H$_2$ (g), and stirred for 48 h at 25° C. The mixture was filtered thru Celite and concentrated in vacuo. The residue was dissolved in a minimal amount of CH$_2$Cl$_2$ and purified by flash chromatography (SiO$_2$, 0-50% ethyl acetate-hexanes) to afford the title compound as a white solid 0.926 g, 89%). $^1$H NMR (600 MHz, CDCl$_3$) δ 8.05 (1H, br s), 7.76 (1H, br s), 7.41-7.60 (3H, br m), 7.25 (1H, t, J=7.8 Hz), 7.15-7.24 (1H, br s), 5.31 (1H, s), 4.85 (1H, br s), 4.49 (1H, br s), 4.31-4.32 (1H, m), 2.56 (1H, br s), 2.38 (1H, br s), 2.12-2.17 (1H, m), 2.00 (1H, qt, J=13.2, 3.6 Hz), 1.96 (1H, d, J=3.0 Hz), 1.93-1.96 (1H, m), 1.65-1.76 (2H, m); LCMS m/z 300.1393 ([M+H$^+$], C$_{18}$H$_{18}$FNO$_2$ requires 300.1394).

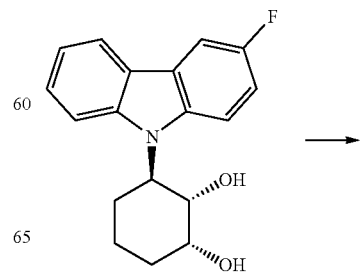

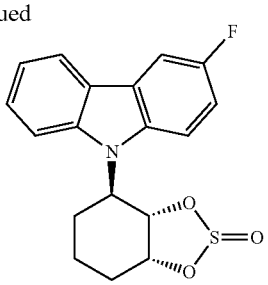

(3aS,4R,7aR)-4-(3-fluoro-9H-carbazol-9-yl)hexahydrobenzo[d][1,3,2]dioxathiole 2-oxide A solution of (1R,2S,3R)-3-(3-fluoro-9H-carbazol-9-yl)cyclohexane-1,2-diol (0.906 g, 3.03 mmol) in CH$_2$Cl$_2$ (10.0 mL) at 0° C. was treated dropwise with triethylamine (3.36 mL, 24.2 mmol), and SOCl$_2$ (0.66 mL, 9.08 mmol). The mixture was warmed to 25° C., stirred for 2 h, poured over a solution of saturated aqueous sodium chloride (100 mL), and then extracted CH$_2$Cl$_2$ (3×100 mL). The combined organic layers were washed with water (2×100 mL), saturated aqueous sodium chloride (100 mL), dried (Na$_2$SO$_4$), and concentrated in vacuo. The residue was dissolved in a minimal amount of CH$_2$Cl$_2$ and purified by flash chromatography (SiO$_2$, 0-10% ethyl acetate-hexanes) to afford the title compound as an orange oil (1.16 g, 99%). $^1$H NMR (600 MHz, CDCl$_3$) δ (as a mixture of sulfite diastereomers) 8.07 (1H, br s), 1H[7.78 (br s), 7.73 (br s), 7.67 (br s), 7.60 (br s)], 2H[7.40-7.54 (m), 7.35 (br s)], 7.27 (2H, t, J=6.0 Hz), 7.19 (1H, br s), 1H[5.48 (br s), 5.27 (m)], 5.34-5.44 (1H, m), 1H[4.93-4.95 (m), 4.47 (br s)], 2.57-2.61 (1H, m), 2.36-2.55 (1H, m), 2.16 (1H, tt, J=16.8, 4.2 Hz), 2.00-2.08 (2H, m), 1.82-2.00 (1H, m), 1.88 (1H, qt, J=13.8, 3.0 Hz); LCMS m/z 346.0912 ([M+H$^+$], C$_{18}$H$_{16}$FNO$_3$S requires 346.0908).

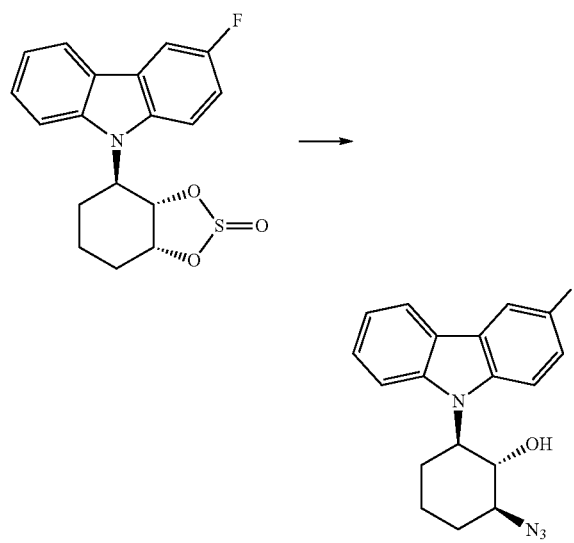

(1S,2S,6R)-2-azido-6-(3-fluoro-9H-carbazol-9-yl)cyclohexanol

A solution of (3aS,4R,7aR)-4-(3-fluoro-9H-carbazol-9-yl)hexahydrobenzo[d][1,3,2]dioxathiole 2-oxide (1.16 g, 3.36 mmol) in DMF (10.0 ml) was treated with sodium azide (0.656 g, 10.1 mmol), and heated to 110° C. for 14 h under microwave irradiation. The mixture was diluted with CH$_2$Cl$_2$ (200 mL) and this organic layer was washed with saturated aqueous NaCl (3×100 mL), dried (Na$_2$SO$_4$), and concentrated in vacuo. The residue was dissolved in a minimal amount of CH$_2$Cl$_2$ and purified by flash chromatography (SiO$_2$, 0-10% ethyl acetate-hexanes) to afford the title compound as a clear oil (0.775 g, 71%). $^1$H NMR (600 MHz, CDCl$_3$) δ 1H[8.05 (d, J=7.2 Hz), 8.04 (d, J=7.8 Hz)], 1H[7.78 (dd, J=9.0, 3.0 Hz), 7.78 (dd, J=8.4, 2.4 Hz)], 1H[7.55 (d, J=8.4 Hz), 7.38 (dd, J=9.0, 3.6 Hz)], 7.43-7.52 (2H, m), 7.22-7.26 (1H, m), 1H[7.21 (td, J=9.0, 3.0 Hz), 7.17 (td, J=8.4, 2.4 Hz)], 4.35-4.47 (2H, m), 3.54-3.61 (1H, m), 2.38-2.50 (1H, m), 2.18-2.24 (1H, m), 2.14-2.19 (1H, m), 2.00-2.04 (1H, m), 1.94-1.98 (1H, m), 1.55-1.64 (2H, m); LCMS m/z 325.1455 ([M+H$^+$], C$_{18}$H$_{17}$FN$_4$O requires 325.1459).

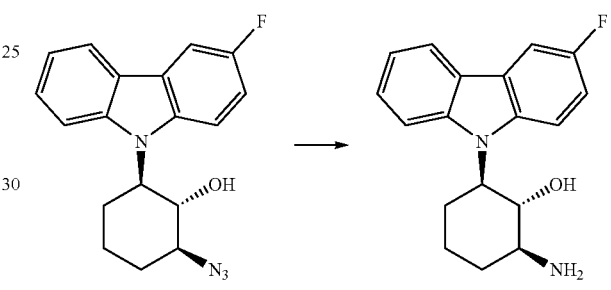

(1R,2S,6R)-2-amino-6-(3-fluoro-9H-carbazol-9-yl)cyclohexanol

A solution of (1S,2S,6R)-2-azido-6-(3-fluoro-9H-carbazol-9-yl)cyclohexanol (0.755 g, 2.33 mmol) in THF (10.0 mL) was cooled to 0° C., treated with PPh$_3$ (0.794 g, 3.03 mmol), H$_2$O (0.5 mL), and stirred for 14 h at 25° C. The solution was concentrated to dryness, dissolved in a minimal amount of CH$_2$Cl$_2$ and purified by flash chromatography (SiO$_2$, 0-50% ethyl acetate-hexanes to remove nonpolar impurities followed by 3% MeOH—CH$_2$Cl$_2$ to remove triphenylphospine oxide and 17:2:1 CH$_2$Cl$_2$:MeOH:NH$_4$OH to elute the product). The combined fractions of pure product were concentrated, dried azeotropically with toluene to afford the title compound as a white solid (0.648 g, 93%). $^1$H NMR (600 MHz, CDCl$_3$) δ 1H[8.06 (d, J=7.8 Hz), 8.01 (d, J=8.4 Hz)], 1H[7.77 (dd, J=9.0, 2.4 Hz), 8.01 (d, J=9.0, 2.4 Hz)], 2H[7.60 (1H, d, J=8.4 Hz), 7.41-7.44 (m)], 1H[7.50 (dd, J=9.0, 3.6 Hz), 7.34 (dd, J=9.0, 4.2 Hz)], 2H[7.24 (t, J=7.8 Hz), 7.13-7.21 (m)], 1H[4.35 (ddd, J=12.6, 10.2, 4.2 Hz), 4.29 (ddd, J=12.6, 10.2, 4.2 Hz)], 3.97-4.04 (1H, m), 2.66-2.73 (1H, m), 1H[2.41 (qd, 7.34 (dd, J=13.2, 3.6 Hz), 2.37 (qd, J=13.2, 4.2 Hz)], 1.83-1.94 (6H, m), 1.48-1.56 (1H, m), 1.30 (1H, qt, J=13.2, 3.6 Hz); LCMS m/z 299.1556 ([M+H$^+$], C$_{18}$H$_{19}$FN$_2$O requires 299.1554).

Example 31a

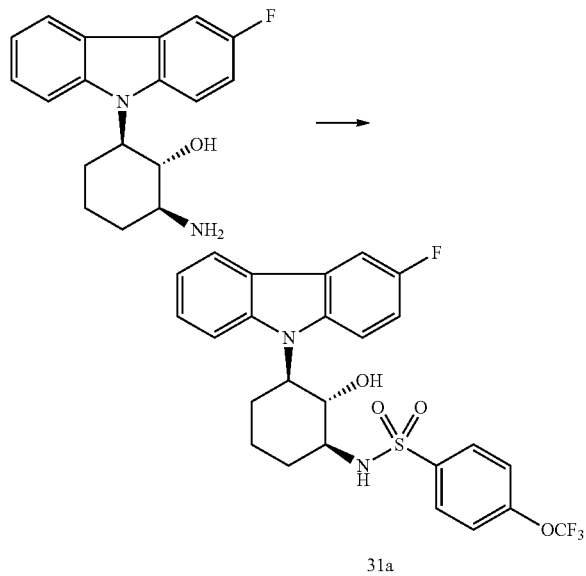

31a

N-((1S,2S,3R)-3-(3-fluoro-9H-carbazol-9-yl)-2-hydroxycyclohexyl)-4-(trifluoromethoxy)benzenesulfonamide A solution of (1R,2S,6R)-2-amino-6-(3-fluoro-9H-carbazol-9-yl)cyclohexanol (0.220 g, 0.737 mmol) in CH$_2$Cl$_2$ (2.0 mL) was cooled to 0° C., treated with Et$_3$N (107 μL, 0.774 mmol), and 4-trifluoromethoxybenzenesulfonyl chloride (131 μL, 0.774 mmol). The mixture was warmed to 25° C., and stirred for 2 h. The mixture was partitioned between saturated aqueous NaCl (50 mL) and CH$_2$Cl$_2$ (100 mL). The organic layer was washed with saturated aqueous NaCl (3×50 mL), dried (Na$_2$SO$_4$), and concentrated in vacuo. The residue was dissolved in a minimal amount of CH$_2$Cl$_2$ and purified by flash chromatography (SiO$_2$, 0-35% ethyl acetate-hexanes). The pure fractions were combined, concentrated, and the residue was dissolved in a minimal amount of ethyl acetate and precipitated with the addition of hexanes to afford the title compound as a white solid (0.269 g, 70%). [α]$_D$=+3 (1.0 in CH$_2$Cl$_2$), $^1$H NMR (600 MHz, CDCl$_3$) δ 1H[8.02 (d, J=7.8 Hz), 7.97 (d, J=7.8 Hz)], 2H[7.94 (d, J=1.8 Hz), 7.93 (d, J=1.8 Hz)], 1H[7.74 (dd, J=8.4, 2.4 Hz), 7.65 (d, J=8.4, 2.4 Hz)], 1H[7.53 (d, J=7.8 Hz), 7.29 (d, J=8.4 Hz), 1H[7.45 (dd, J=9.0, 3.6 Hz), 7.16 (dd, J=9.0, 4.2 Hz),], 7.40 (1H, dt, J=7.8 Hz), 7.31 (2H, dd, J=8.4, 2.4 Hz), 1H[7.23 (t, J=7.2 Hz), 7.19 (t, J=7.2 Hz)], 1H[7.13 (td, J=9.0, 2.4 Hz), 7.06 (td, J=8.4, 2.4 Hz)], 1H[5.32 (d, J=5.4 Hz), 5.26 (d, J=4.8 Hz)], 4.18-4.32 (2H, m), 3.21-3.24 (1H, m), 2H[2.35-2.41 (m), 2.28-2.35 (m)], 2.13-2.16 (1H, m), 1.85-1.89 (2H, m), 1.41-1.54 (2H, m); LCMS m/z 523.1313 ([M+H$^+$], C$_{25}$H$_{22}$F$_4$N$_2$O$_4$S requires 523.1309).

Example 31b

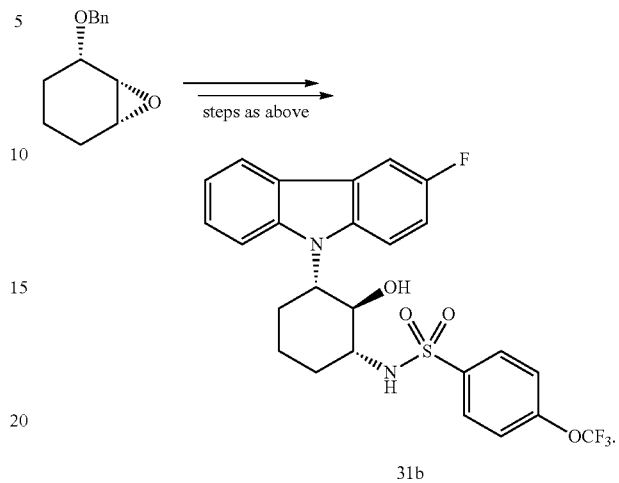

31b

Enantiomer as above starting from (1R,2S,6R)-2-(benzyloxy)-7-oxabicyclo[4.1.0]heptane to yield Example 31b: N-((1S,2S,3R)-3-(3-fluoro-9H-carbazol-9-yl)-2-hydroxycyclohexyl)-4-(trifluoromethoxy)benzenesulfonamide. [α]$_D$=−3 (1.0 in CH$_2$Cl$_2$).

Examples 32a and 32b

Chiral materials. Method analogous to stereoselective synthesis of 3-optically active staring materials

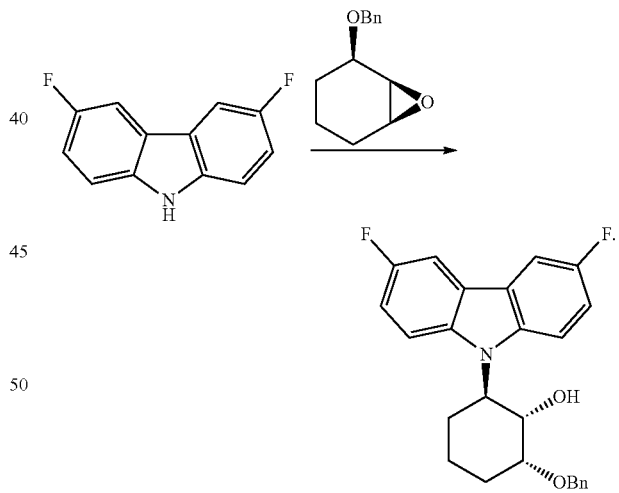

(1S,2R,6R)-2-(benzyloxy)-6-(3,6-difluoro-9H-carbazol-9-yl)cyclohexanol

A solution of 3,6-difluoro-9H-carbazole (1.00 g, 4.92 mmol) in toluene (10 mL) at 0° C. was treated with NaH (60% dispersion in mineral oil (0.393 g, 9.84 mmol), and (1S,2R,6S)-2-(benzyloxy)-7-oxabicyclo[4.1.0]heptane (1.00 g, 4.92 mmol). The mixture was warmed to 100° C. and stirred for 14 h. The mixture was cooled to 25° C., treated with saturated aqueous NH$_4$Cl (50 mL), and extracted with toluene (3×50 mL). The organic layer was washed with saturated aqueous NaCl (3×50 mL), dried (Na$_2$SO$_4$), and concentrated in vacuo. The residue was dissolved in a minimal amount of toluene and purified by flash chromatography (SiO$_2$, 0-10% ethyl acetate-hexanes) to afford the title compound as a beige foam (1.78 g, 89%). $^1$H NMR (600 MHz, CDCl$_3$) δ 7.66-7.69 (2H, m), 7.39-7.45 (5H, m), 2H[7.35-7.39 (m), 7.31 (dd, J=9.0, 4.2 Hz)], 7.15-7.21 (2H, m), 4.79 (1H, d, J=12.0 Hz), 4.77 (1H, ddd, J=12.6, 10.8, 4.2 Hz), 4.59 (1H, d, J=12.0 Hz), 4.41 (1H, ddd, J=12.0, 10.2, 3.0 Hz), 4.10-4.11 (1H, m), 2.37 (1H, qd, J=13.2, 4.2 Hz), 2.29 (1H, doublet of quintets, J=14.4, 2.4 Hz), 2.20 (1H, d, J=9.0 Hz), 1.98-2.02 (1H, m), 1.91 (1H, qt, J=13.8, 3.6 Hz), 1.72-1.77 (1H, m), 1.52-1.60 (1H, m); LCMS m/z 408.1770 ([M+H$^+$], C$_{25}$H$_{23}$F$_2$NO$_2$ requires 408.1770).

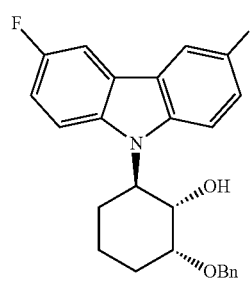

(1R,2S,3R)-3-(3,6-difluoro-9H-carbazol-9-yl)cyclohexane-1,2-diol

A solution of (1S,2R,6R)-2-(benzyloxy)-6-(3,6-difluoro-9H-carbazol-9-yl)cyclohexanol (1.77 g, 4.34 mmol) in THF:MeOH (1:1, 10.0 mL) was treated with 10% Pd/C (0.923 g), placed under an atmosphere of H$_2$ (g), and stirred for 48 h at 25° C. The mixture was filtered thru Celite and concentrated in vacuo. The residue was dissolved in a minimal amount of CH$_2$Cl$_2$ and purified by flash chromatography (SiO$_2$, 0-50% ethyl acetate-hexanes) to afford the title compound as a beige foam (1.14 g, 82%) with additional recovered starting material (0.41 g, 23%). $^1$H NMR (600 MHz, CDCl$_3$) δ 7.68 (2H, br s), 7.45 (2H, br s), 7.20 (2H, br s), 4.79 (1H, ddd, J=13.2, 10.8, 4.2 Hz), 4.40 (1H, dd, J=10.2, 3.0 Hz), 2.64 (1H, br s), 2.32 (1H, qd, J=12.2, 3.6 Hz), 2.07-2.13 (1H, m), 2.10-2.17 (1H, br m), 1.91-2.01 (2H, m), 1.69-1.74 (1H, m), 1.62-1.68 (1H, m); LCMS m/z 318.1302 ([M+H$^+$], C$_{18}$H$_{17}$F$_2$NO$_2$ requires 318.1300).

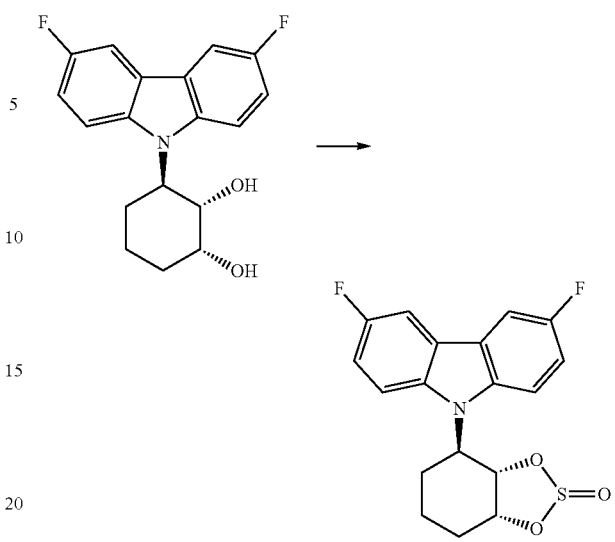

(3aS,4R,7aR)-4-(3,6-difluoro-9H-carbazol-9-yl)hexahydrobenzo[d][1,3,2]dioxathiole 2-oxide A solution of (1R,2S,3R)-3-(3,6-difluoro-9H-carbazol-9-yl)cyclohexane-1,2-diol (1.26 g, 3.97 mmol) in CH$_2$Cl$_2$ (20.0 mL) at 0° C. was treated dropwise with triethylamine (4.40 mL, 31.8 mmol), and SOCl$_2$ (0.86 mL, 11.9 mmol). The mixture was warmed to 25° C., stirred for 2 h, poured over a solution of saturated aqueous sodium chloride (100 mL), and then extracted CH$_2$Cl$_2$ (3×100 mL). The combined organic layers were washed with water (2×100 mL), saturated aqueous sodium chloride (100 mL), dried (Na$_2$SO$_4$), and concentrated in vacuo. The residue was dissolved in a minimal amount of CH$_2$Cl$_2$ and purified by flash chromatography (SiO$_2$, 0-10% ethyl acetate-hexanes) to afford the title compound as an orange solid (1.29 g, 89%). $^1$H NMR (600 MHz, CDCl$_3$) δ (as a mixture of sulfite diastereomers) 2H[7.71 (br s), 7.66 (br s), 7.60 (br s)], 7.34 (2H, br s), 7.15-7.25 (2H, br s), 1H[5.43 (dd, J=9.6, 4.8 Hz), 5.22 (dd, J=10.2, 5.4 Hz)], 1H[5.37-5.39 (m), 4.93-4.95 (m)], 4.24 (1H, ddd, J=13.2, 9.0, 4.2 Hz), 2.56-2.63 (1H, m), 2.39 (1H, qd, J=13.2, 3.0 Hz), 2.16 (1H, tt, J=9.6, 4.2 Hz), 2.00-2.07 (2H, m), 1.94-2.00 (1H, m), 1.86 (1H, qt, J=13.8, 3.0 Hz); LCMS m/z 364.0797 ([M+H$^+$], C$_{18}$H$_{15}$F$_2$NO$_3$S requires 364.0813).

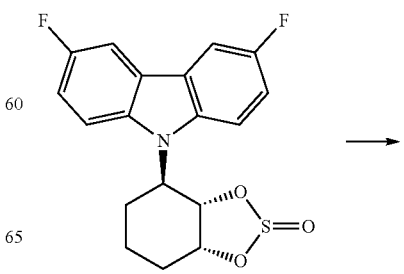

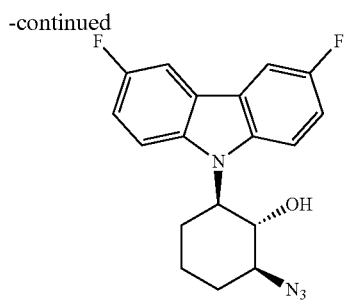

(1S,2S,6R)-2-azido-6-(3,6-difluoro-9H-carbazol-9-yl)cyclohexanol

A solution of (3aS,4R,7aR)-4-(3,6-difluoro-9H-carbazol-9-yl)hexahydrobenzo[d][1,3,2]dioxathiole 2-oxide (1.27 g, 3.50 mmol) in DMF (8.0 ml) was treated with sodium azide (0.684 g, 10.5 mmol), and heated to 110° C. for 14 h under microwave irradiation. The mixture was diluted with $CH_2Cl_2$ (200 mL) and this organic layer was washed with saturated aqueous NaCl (3×100 mL), dried ($Na_2SO_4$), and concentrated in vacuo. The residue was dissolved in a minimal amount of $CH_2Cl_2$ and purified by flash chromatography ($SiO_2$, 0-10% ethyl acetate-hexanes) to afford the title compound as a beige oil (0.921 g, 77%). $^1$H NMR (600 MHz, $CDCl_3$) δ 7.71 (1H, dd, J=8.4, 2.4 Hz), 7.67 (1H, dd, J=8.4, 2.4 Hz), 7.47 (1H, dd, J=9.0, 4.2 Hz), 7.38 (1H, dd, J=9.0, 1.8 Hz), 7.23 (1H, td, J=8.4, 2.4 Hz), 7.18 (1H, td, J=9.0, 2.4 Hz), 4.40 (1H, td, J=10.2, 4.2 Hz), 4.33 (1H, t, J=10.2 Hz), 3.56 (1H, ddd, J=10.8, 9.0, 4.2 Hz), 2.40 (1H, qd, J=12.6, 3.6 Hz), 2.20-2.22 (2H, m), 2.01-2.03 (1H, m), 1.95-1.98 (1H, m), 1.55-1.65 (2H, m); $^{13}$C NMR (150 MHz, $CDCl_3$) δ 158.1 (d, J=54 Hz), 156.6 (d, J=60 Hz), 139.0, 135.6, 124.6 (dd, J=36, 18 Hz), 122.9 (dd, J=36, 18 Hz), 114.6 (d, J=102 Hz), 114.1 (d, J=96 Hz), 112.1 (d, J=36 Hz), 110.1 (d, J=36 Hz), 106.8 (d, J=90 Hz), 106.1 (d, J=96 Hz), 74.5, 65.8, 60.1, 30.3, 28.5, 22.8; LCMS m/z 343.1374 ([M+H$^+$], $C_{18}H_{16}F_2N_4O$ requires 343.1365).

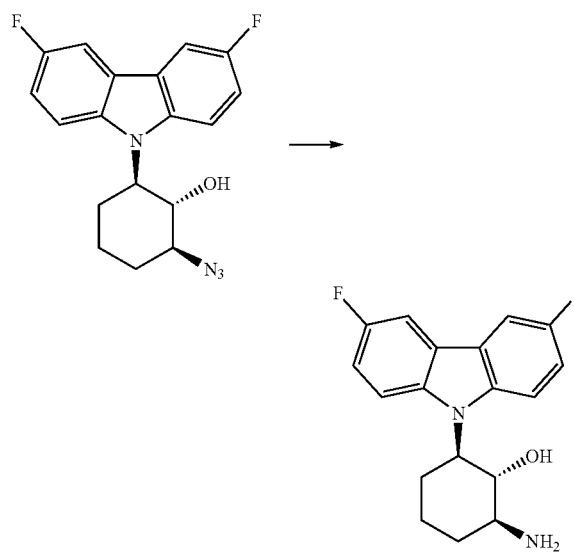

(1R,2S,6R)-2-amino-6-(3,6-difluoro-9H-carbazol-9-yl)cyclohexanol

A solution of (1S,2S,6R)-2-azido-6-(3,6-difluoro-9H-carbazol-9-yl)cyclohexanol (0.901 g, 2.63 mmol) in THF (10.0 mL) was cooled to 0° C., treated with $PPh_3$ (1.04 g, 3.95 mmol), $H_2O$ (0.5 mL), and stirred for 14 h at 25° C. The solution was concentrated to dryness, dissolved in a minimal amount of $CH_2Cl_2$ and purified by flash chromatography ($SiO_2$, 0-50% ethyl acetate-hexanes to remove nonpolar impurities followed by 3% MeOH—$CH_2Cl_2$ to remove triphenylphospine oxide and 17:2:1 $CH_2Cl_2$:MeOH:$NH_4OH$ to elute the product). The combined fractions of pure product were concentrated, dried azeotropically with toluene to afford the title compound as a white solid (0.790 g, 95%). $^1$H NMR (600 MHz, $CDCl_3$) δ 7.70 (1H, dd, J=8.4, 2.4 Hz), 7.66 (1H, dd, J=8.4, 2.4 Hz), 7.47 (1H, dd, J=9.0, 3.6 Hz), 7.36 (1H, dd, J=9.0, 3.6 Hz), 7.21 (1H, td, J=9.0, 3.0 Hz), 7.16 (1H, td, J=9.0, 2.4 Hz), 4.31 (1H, ddd, J=13.2, 10.2, 3.6 Hz), 4.02 (1H, t, J=9.0 Hz), 2.74 (1H, ddd, J=12.0, 9.0, 3.6 Hz), 2.37 (1H, qd, J=13.2, 3.6 Hz), 1.75-2.05 (3H, m), 1.55 (1H, qt, J=13.2, 3.6 Hz), 1.35 (1H, qd, J=13.8, 4.2 Hz); LCMS m/z 317.1459 ([M+H$^+$], $C_{18}H_{18}F_2N_2O$ requires 317.1460).

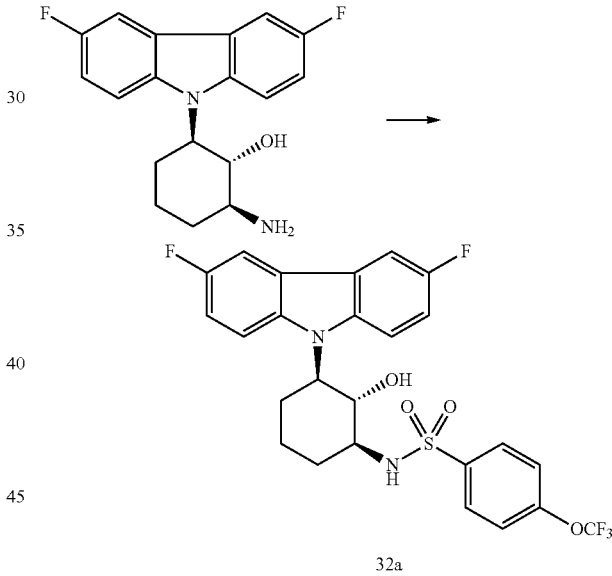

32a

N-((1S,2S,3R)-3-(3,6-difluoro-9H-carbazol-9-yl)-2-hydroxycyclohexyl)-4-(trifluoromethoxy)benzenesulfonamide A solution of (1R,2S,6R)-2-amino-6-(3,6-difluoro-9H-carbazol-9-yl)cyclohexanol (0.200 g, 0.664 mmol) in $CH_2Cl_2$ (2.0 mL) was cooled to 0° C., treated with $Et_3N$ (97.0 μL, 0.697 mmol), and 4-trifluoromethoxybenzenesulfonyl chloride (118 μL, 0.697 mmol). The mixture was warmed to 25° C., and stirred for 2 h. The mixture was partitioned between saturated aqueous NaCl (50 mL) and $CH_2Cl_2$ (100 mL). The organic layer was washed with saturated aqueous NaCl (3×50 mL), dried ($Na_2SO_4$), and concentrated in vacuo. The residue was dissolved in a minimal amount of $CH_2Cl_2$ and purified by flash chromatography ($SiO_2$, 0-35% ethyl acetate-hexanes). The pure fractions were combined, concentrated, and the residue was dissolved in a minimal amount of ethyl acetate and precipitated with the addition of hexanes to afford the title compound Example 32a as a white solid (0.347 g, 97%). $[\alpha]_D=+4$ (1.0 in $CH_2Cl_2$). $^1H$ NMR (600 MHz, $CDCl_3$) δ 7.94 (2H, d, J=8.4 Hz), 7.57 (1H, dd, J=8.4, 2.4 Hz), 7.48 (1H, dd, J=9.0, 4.2 Hz), 7.45 (1H, dd, J=9.0, 2.4 Hz), 7.31 (2H, d, J=9.0 Hz), 7.11 (1H, td, J=9.0, 2.4 Hz), 5.93 (1H, d, J=6.6 Hz), 4.27 (1H, t, J=9.6, 3.0 Hz), 3.98 (1H, ddd, J=13.2, 10.2, 4.2 Hz), 3.17-3.23 (1H, m), 3.03 (1H, d, J=3.0 Hz), 2.22 (1H, qd, J=13.2, 4.8 Hz), 1.80-1.82 (1H, m), 1.73-1.77 (2H, m), 1.41 (1H, td, J=12.2, 3.6 Hz), 1.22-1.30 (1H, m); $^{13}C$ NMR (150 MHz, $CDCl_3$) δ 157.9 (d, J=24 Hz), 156.3 (d, J=18 Hz), 152.3, 139.7, 138.7, 135.4, 129.2, 124.3 (dd, J=36, 18 Hz), 122.5 (dd, J=36, 18 Hz), 121.1, 120.4 (q, J=1032 Hz), 114.4 (d, J=102 Hz), 113.9 (d, J=36 Hz), 112.3 (d, J=36 Hz), 110.1 (d, J=36 Hz), 106.4 (d, J=96 Hz), 105.8 (d, J=96 Hz), 72.4, 60.1, 59.1, 31.4, 28.3, 22.7; LCMS m/z 541.1223 ($[M+H^+]$, $C_{25}H_{21}F_5N_2O_4S$ requires 541.1215).

Example 32b

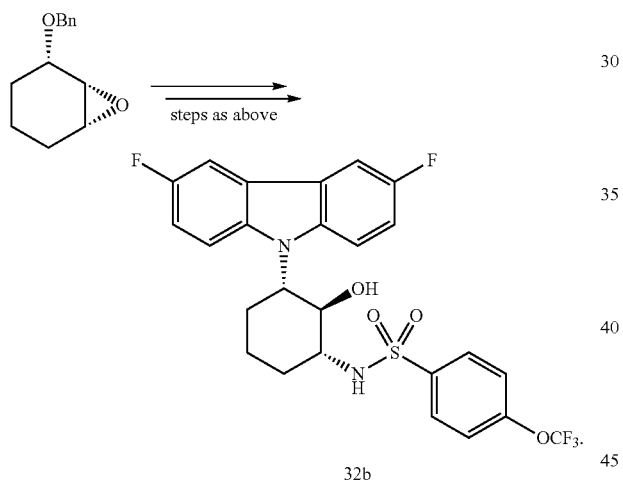

32b

Enantiomer as above starting from (1R,2S,6R)-2-(benzyloxy)-7-oxabicyclo[4.1.0]heptane to yield Example 32b, that is $N_4$(1R,2R,3S)-3-(3,6-difluoro-9H-carbazol-9-yl)-2-hydroxycyclohexyl)-4-(trifluoromethoxy)benzenesulfonamide. $[\alpha]_D=-4$ (1.0 in $CH_2Cl_2$).

Substituted Phenoxazines

Substituted phenoxazines and heterocyclic analogs of the phenoxazine system are known and these may be incorporated into active compounds disclosed in the present invention by methods used for the synthesis of Examples 1, 1a and 1b or variants thereof. The syntheses outlined in I. Thome and Carsten Bolm, Org. Lett., Vol. 14. No. 7, 2012, pages 1892-1895 provide ready access to several relevant reagents, for example 2-fluoro-10H-phenoxazine, 3-fluoro-10H-phenoxazine, 2-(trifluoromethyl)-10H-phenoxazine and 8-fluoro-10H-benzo[b]pyrido[2,3-e][1,4]oxazine. As an example the literature synthesis of 2-fluoro-10H-phenoxazine with the additional hydrolytic removal of the N-protecting group is shown in Scheme 7.

Scheme 7

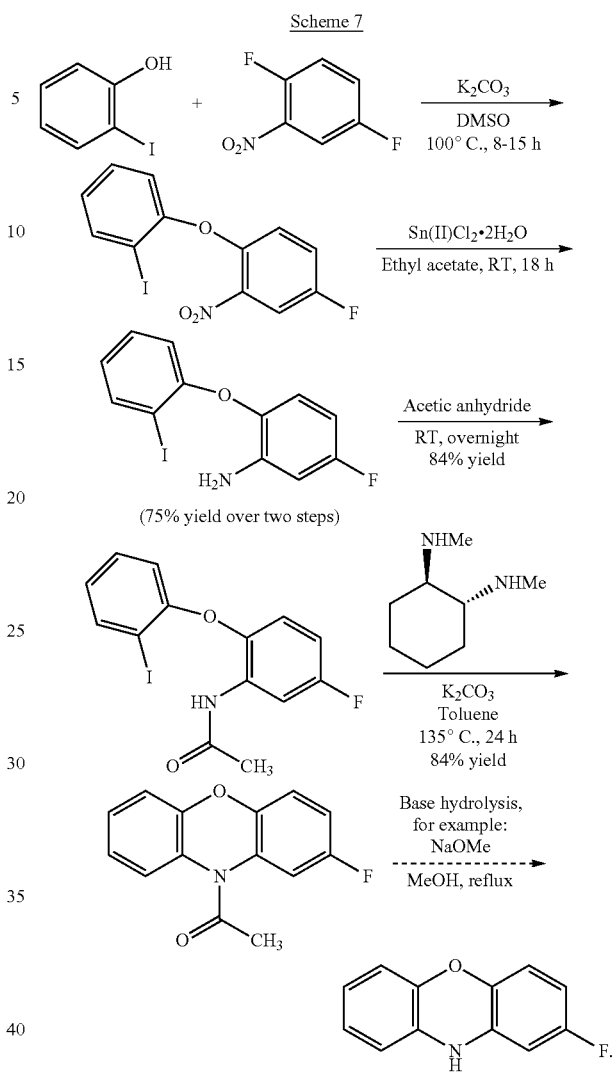

2-fluoro-10H-phenoxazine

A related copper mediated method has been used to access 3,7-difluoro-10H-phenoxazine as shown in Scheme 8:

Scheme 8

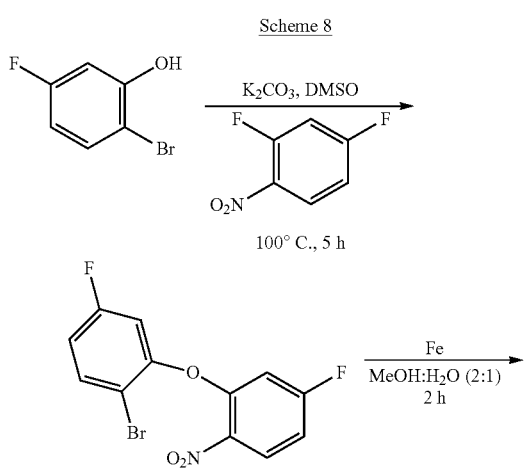

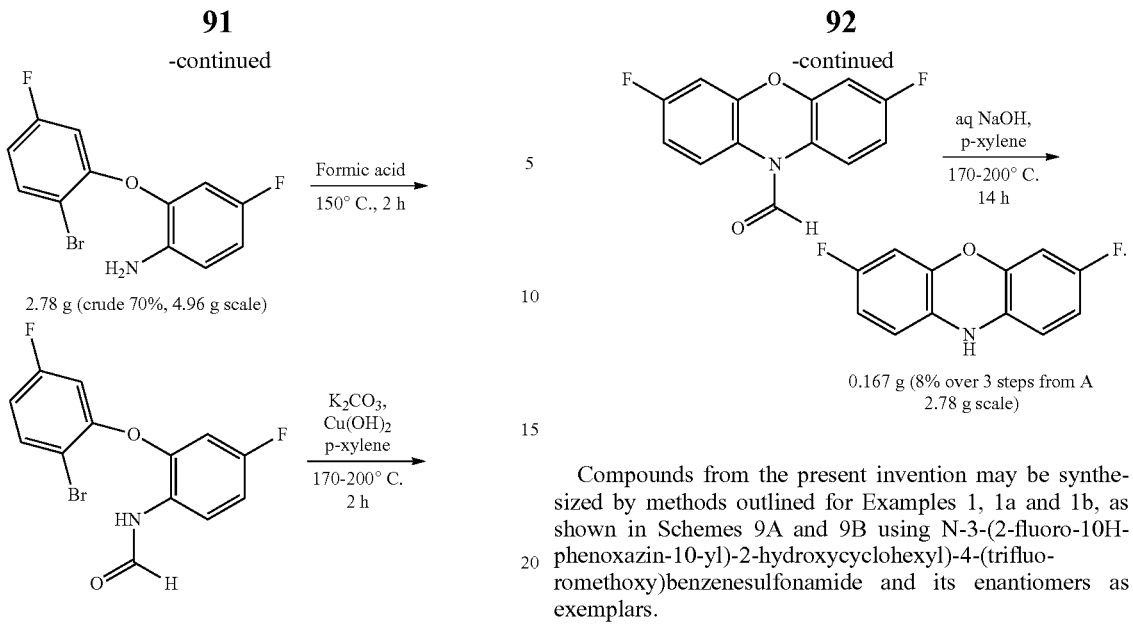
2.78 g (crude 70%, 4.96 g scale)
0.167 g (8% over 3 steps from A
2.78 g scale)
Compounds from the present invention may be synthesized by methods outlined for Examples 1, 1a and 1b, as shown in Schemes 9A and 9B using N-3-(2-fluoro-10H-phenoxazin-10-yl)-2-hydroxycyclohexyl)-4-(trifluoromethoxy)benzenesulfonamide and its enantiomers as exemplars.
Scheme 9A
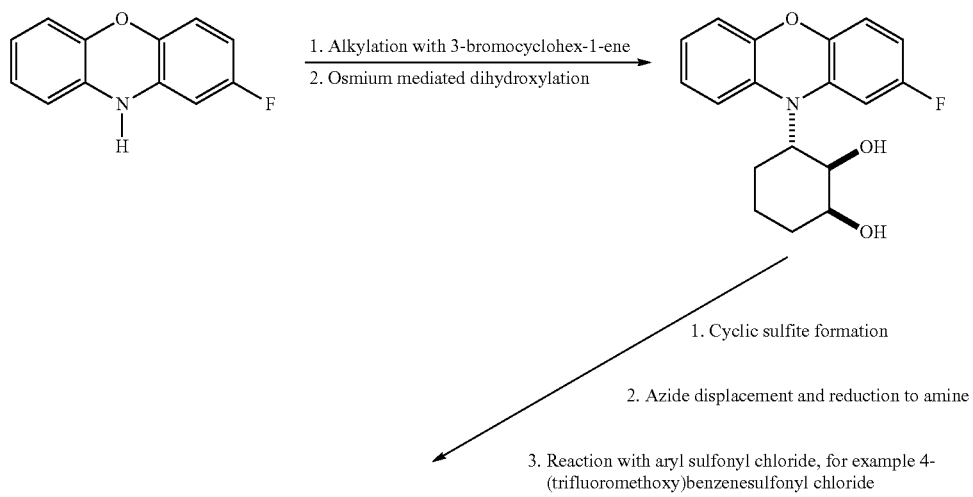
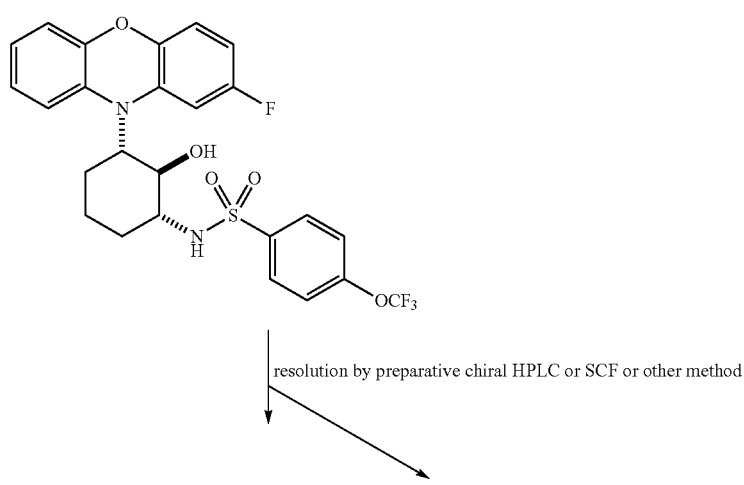
resolution by preparative chiral HPLC or SCF or other method

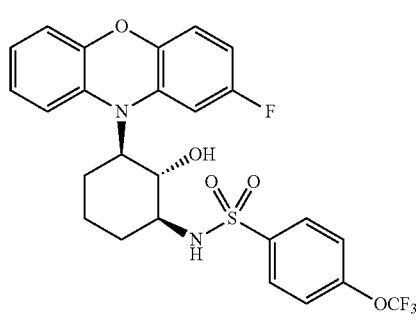 [SMILES: O=S(=O)(N[C@H]1CCC[C@@H](N2c3ccccc3Oc3ccccc32)[C@@H]1O)c1ccc(OC(F)(F)F)cc1]

1S,2S,3R absolute stereochemistry

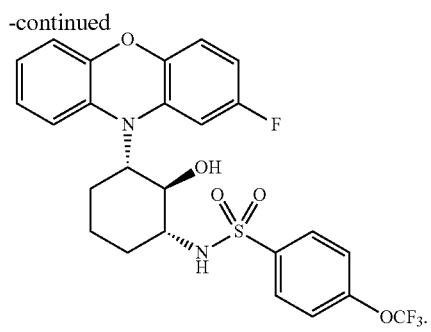

1R,2R,3S absolute stereochemistry

Thus 2-fluoro-10H-phenoxazine is alkylated with a cyclic allylic electrophile such as 3-bromocyclohex-1-ene and the product is cis-dihydroxylated with osmium tetroxide, potassium osmate or other reagent and an appropriate co-oxidant such as N-methylmorpholine N-oxide in the case of osmium based reagents. This yields racemic 3-(2-fluoro-10H-phenoxazin-10-yl)cyclohexane-1,2-diol: this maybe resolved by preparative chiral HPLC or other method to give single enantiomers and these, or the racemic material, maybe carried forward as described in Example 1. As before, the diol is reacted to form a cyclic sulfite which is displaced with azide and reduced to an amino group which is subsequently reacted with an aryl sulfonyl chloride, in Scheme 9A, 4-(trifluoromethoxy)benzenesulfonyl chloride to give the target example, racemic N-3-(2-fluoro-10H-phenoxazin-10-yl)-2-hydroxycyclohexyl)-4-(trifluoromethoxy)benzenesulfonamide. This maybe resolved into its enantiomers by preparative chiral HPLC or other methods to give the single enantiomers of the target compound, N-((1R,2R,3S)-3-(2-fluoro-10H-phenoxazin-10-yl)-2-hydroxycyclohexyl)-4-(trifluoromethoxy)benzenesulfonamide and N-((1S,2S,3R)-3-(2-fluoro-10H-phenoxazin-10-yl)-2-hydroxycyclohexyl)-4-(trifluoromethoxy)benzenesulfonamide.

Alternatively, Pd mediated asymmetric allylation maybe carried out on relevant substituted phenoxazines, as shown in Scheme 3B with 3,7-difluoro-10H-phenoxazine as an example, to yield single enantiomers without resorting to resolutions.

Scheme 9B

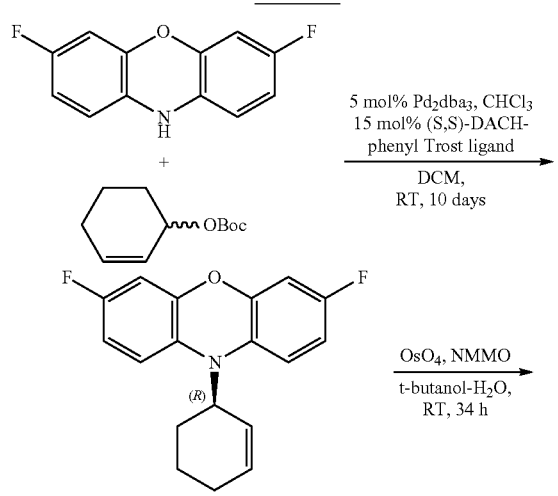

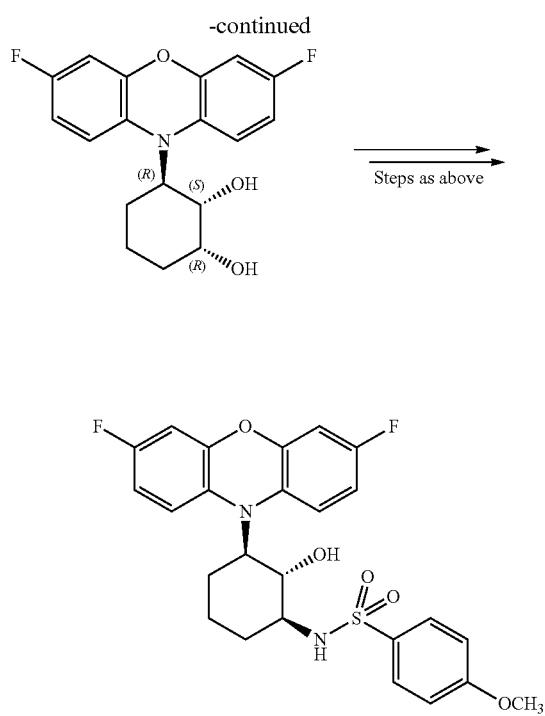

Thus a chiral catalyst is formed from Pd$_2$.dba$_3$.CHCl$_3$ and (S,S)-DACH-phenyl Trost ligand as described in Example 1. This is added to a mixture of 3,7-difluoro-10H-phenoxazine and tert-butyl cyclohex-2-en-1-yl carbonate and the reaction is allowed to proceed at room temperature. The product is (R)-10-(cyclohex-2-en-1-yl)-3,7-difluoro-10H-phenoxazine which is isolated and cis-dihydroxylated to give (1R,2S,3R)-3-(3,7-difluoro-10H-phenoxazin-10-yl)cyclohexane-1,2-diol. This material is carried forward to the target, N-((1S,2S,3R)-3-(3,7-difluoro-10H-phenoxazin-10-yl)-2-hydroxycyclohexyl)-4-methoxybenzenesulfonamide as described above. The other enantiomer, N-((1R,2R,3S)-3-(3,7-difluoro-10H-phenoxazin-10-yl)-2-hydroxycyclohexyl)-4-methoxybenzenesulfonamide, is synthesized using a catalyst formed from (R,R)-DACH-phenyl Trost ligand.

A third route circumventing the cis-dihydroxylation step is epoxide opening of 2-(benzyloxy)-7-oxabicyclo[4.1.0]heptane, either enantiomer of which may be accessed from optically pure cyclohex-2-en-1-ol as described in Example 1. This route is shown in Scheme 10 using 8-fluoro-10H-benzo[b]pyrido[2,3-e][1,4]oxazine as an example.

Scheme 10

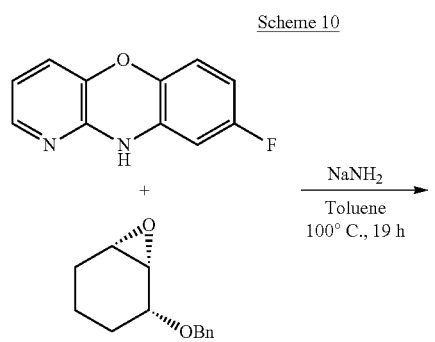

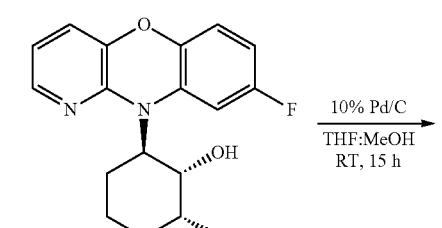

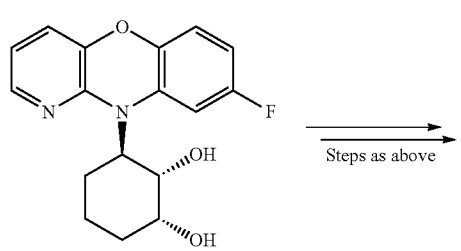

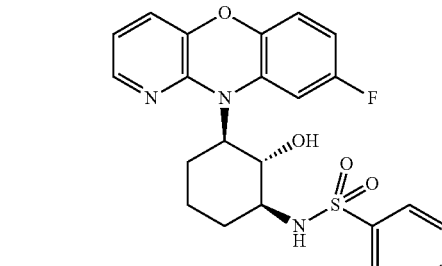

Thus the appropriately substituted phenoxazine or heteroaromatic variant, for example 8-fluoro-10H-benzo[b]pyrido[2,3-e][1,4]oxazine in Scheme 4, is reacted with (1S,2R,6S)-2-(benzyloxy)-7-oxabicyclo[4.1.0]heptane under basic conditions to yield (1S,2R,6R)-2-(benzyloxy)-6-(8-fluoro-10H-benzo[b]pyrido[2,3-e][1,4]oxazin-10-yl)cyclohexan-1-ol. The benzyloxy moiety is cleaved using mild hydrogenolysis or other appropriate deprotection method to yield (1R,2S,3R)-3-(8-fluoro-10H-benzo[b]pyrido[2,3-e][1,4]oxazin-10-yl)cyclohexane-1,2-diol. This diol is carried forward to N-((1S,2S,3R)-3-(8-fluoro-10H-benzo[b]pyrido[2,3-e][1,4]oxazin-10-yl)-2-hydroxycyclohexyl)-4-(trifluoromethoxy)benzenesulfonamide using the steps shown above.

Using the methods described above, or related variants, racemic compounds, or either of their enantiomers, shown below may be synthesized.

Example 34

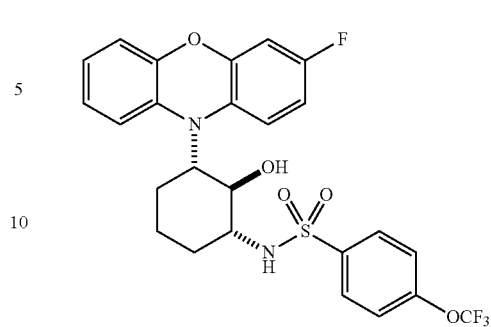

Example 35

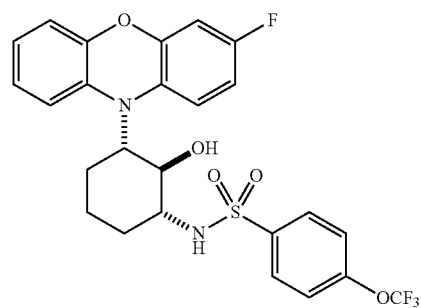

Example 36

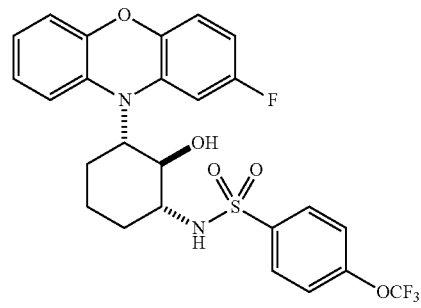

Example 37

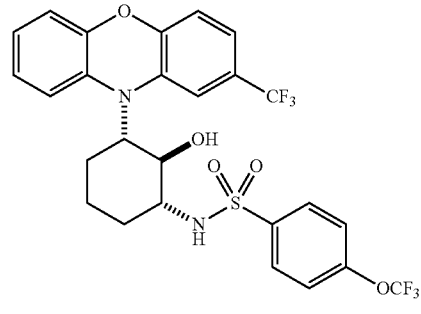

Example 38

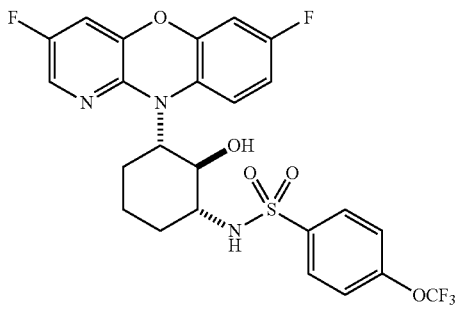

Heterocyclic Analogs of Carbazoles

Heterocyclic analogs of the carbazole system are known and these may be incorporated into active compounds disclosed in the present invention by methods outlined below. Examples of heterocyclic systems include, but are not limited to, 9H-pyrimido[4,5-b]indole, 4H-thieno[3,2-b]indole and 9H-pyrido[3,4-b]indole which may be incorporated into examples shown below:

Example 39

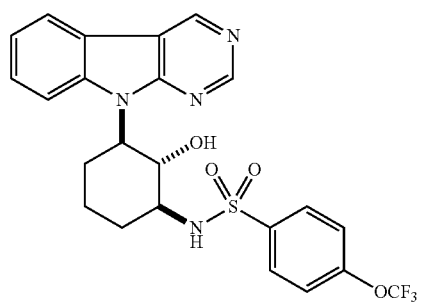

Example 40

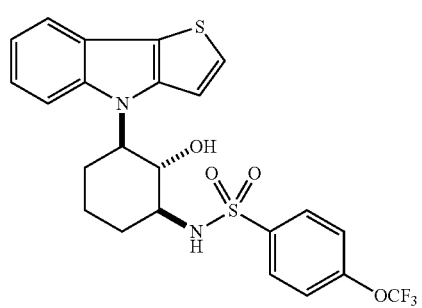

Example 41

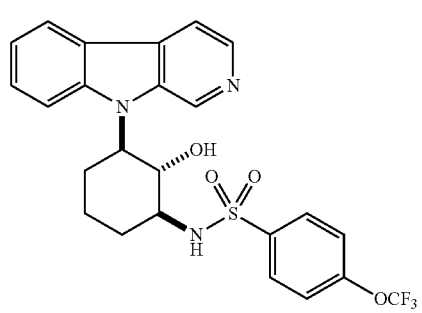

Methods to incorporate 9H-pyrimido[4,5-b]indole are shown in Schemes 11A and 11B:

Scheme 11A

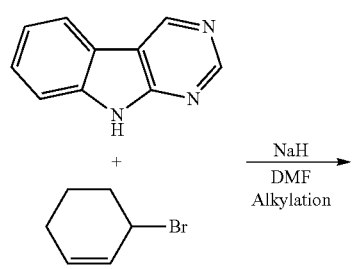

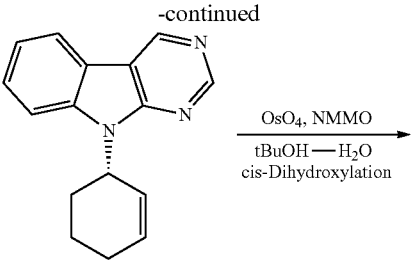

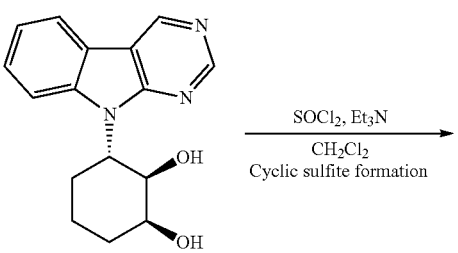

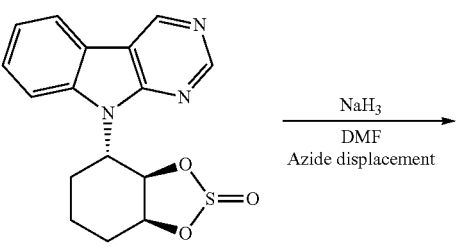

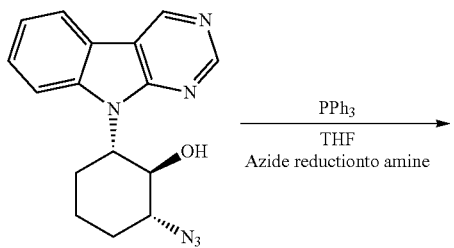

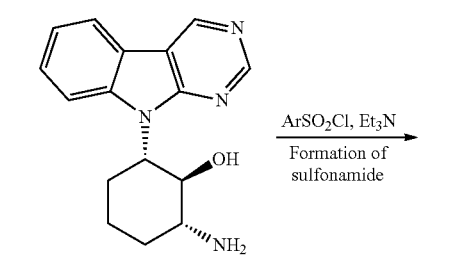

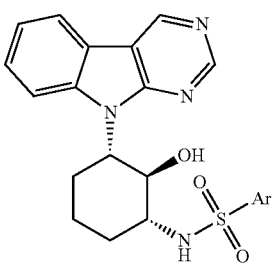

Steps in Scheme 11A are analogous to those used in Example 1. An alternate synthetic route is shown in Scheme 11B:

Scheme 11B

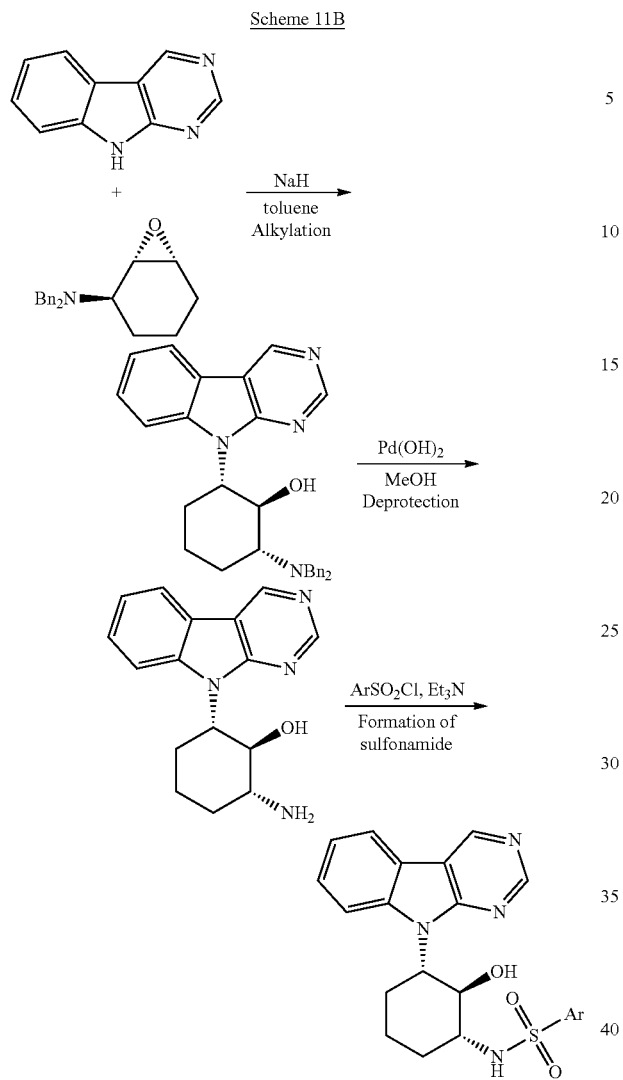

Scheme 12

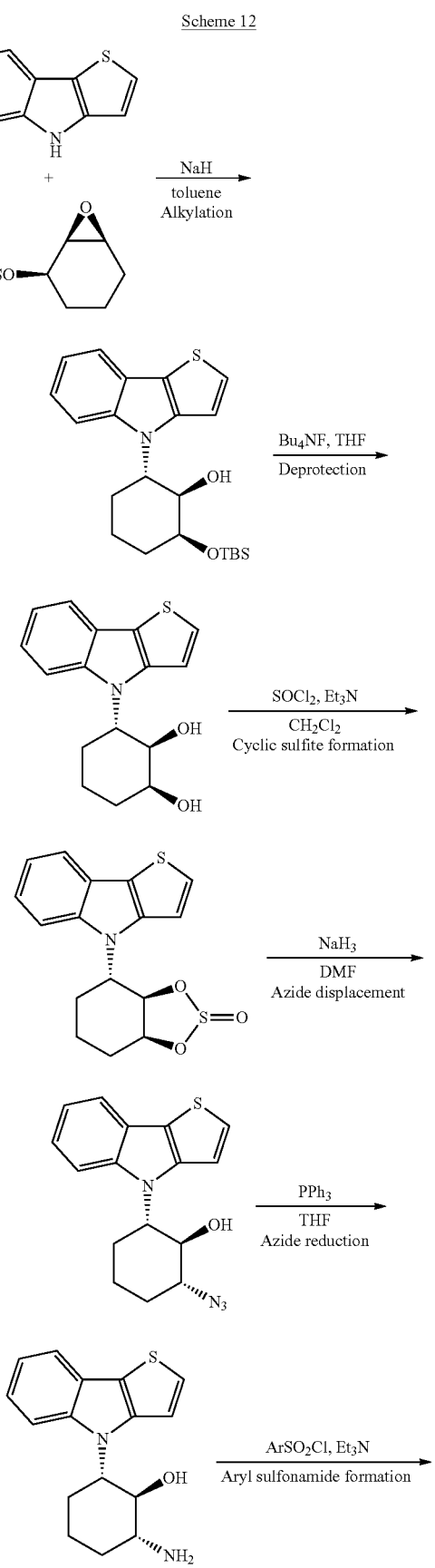

Steps in Scheme 11B are alkylation of 9H-pyrimido[4,5-b]indole with (1S,2R,6R)—N,N-dibenzyl-7-oxabicyclo[4.1.0]heptan-2-amine, deprotection and reaction with aryl sulfonamide to yield the active compound. As shown in Scheme 1B the epoxide may be optically active and either enantiomer may be accessed for the methods described in Aciro, Caroline; Davies, Stephen G.; Roberts, Paul M.; Russell, Angela J.; Smith, Andrew D.; Thomson, James E., Organic & Biomolecular Chemistry (2008), 6(20), 3762-3770 and Davies, Stephen G.; Long, Marcus J. C.; Smith, Andrew D., Chemical Communications (Cambridge, United Kingdom) (2005), (36), 4536-4538.

9H-pyrido[3,4-b]indole may be incorporated into N-2-hydroxy-3-(9H-pyrido[3,4-b]indol-9-yl)cyclohexyl)-4-(trifluoromethoxy)benzenesulfonamide, or either of its enantiomers by the methods in Schemes 11A and 11B, or related variants thereof.

4H-thieno[3,2-b]indole may be incorporated into target structures by the methods shown in Scheme 2. The method is analogous to that used in Example 1 except that a silyl ether protecting group is employed in place of a benzyl on the epoxide alkylating agent, (((1S,2R,6S)-7-oxabicyclo[4.1.0]heptan-2-yl)oxy)(tert-butyl)dimethylsilane, in the first step. The epoxide may be chiral, as shown, and either enantiomer used.

-continued

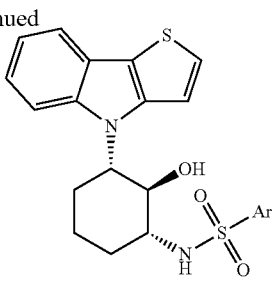

Cell Viability Assays (IC$_{50}$ Determination)

Cell viability assays were performed according to Denizot, F. and R. Lang, Journal of Immunological Methods, 1986. 89(22): p. 271-277. H1650 lung cancer cells were plated at 150,000 cells per well in a 12 well plate. Twenty-four hours after plating, cells were treated as described with increasing concentrations of drug and control. Forty-eight hours after drug treatment, cells were treated with 100 µL of 3-(4,5-Dimethylthiazol-2-yl)-2,5-diphenyltetrazolium bromide (MTT) and incubated for 2 hours at 37 C. The MTT solution was subsequently replaced with 300 µL of n-propyl alcohol and re-aliquoted to a 96 well plate. Spectrophotometric analysis of each solution was performed using a 96 well plate reader at 600 nm in triplicate. Results are shown in Table 1:

TABLE 1

Cell Viability Data

| Example # | IC$_{50}$ (µM) |
|---|---|
| 1 | 5 |
| 2 | 20 |
| 3 | 10 |
| 4 | 15 |
| 5 | 20 |
| 6 | 20 |
| 7 | 25 |
| 8 | 15 |
| 9 | 25 |
| 11 | 20 |

Colony Formation Assay

Protocol for clonogenic assay follows Sangodkar et al., J Clin Invest 2012; 122:2637-51.

Cell culture and staining: For both A549luc and H1650 cells, 500 cells are seeded into each well of a 6-well plate and allowed to attach for 24 hours before drug treatment. The following day, cells are treated with either the appropriate dose of drug or an equivalent volume of DMSO (two replicates were treated for each condition). For each condition, depleted media was replaced with fresh media containing the equivalent drug dose four days after initial treatment. Cells are harvested either 7 (A549 luc) or 8 (H1650) days after initial treatment. Briefly, medium is aspirated from each well and the cells are washed twice with ice-cold PBS, then plates are allowed to dry at room temperature for 4 hours. Cells are fixed for one hour in a fixing solution consisting of 10% methanol and 10% glacial acetic acid in distilled water, then stained overnight in 1% (w/v) crystal violet dissolved in methanol. The next day, staining solution is aspirated from the wells and plates are washed gently with distilled water to remove excess stain before colony counting. Colonies are imaged on a Chemi-Doc XRS+ (Bio-Rad) and images are exported as 8-bit TIFF files. Colonies are counted using the Colony Counter plugin in ImageJ, with colony size defined as between 4 and 400 square pixels, and minimum circularity set at 0.6. Duplicate wells are averaged to obtain a single value for each condition. Results (number of colonies) for A549 luc cells and results (number of colonies) for H1650 cells may be analyzed separately. GI50 for colony formation for selected examples are shown in the table below.

| | GI50 (colony formation) | |
|---|---|---|
| Compound | H1650 | A549 |
| Example 3 | 5 uM | 7.5 uM |
| Example 3a | 5 uM | 7.5 uM |
| Example 3b | 7.5 uM | 10 uM |
| Example 1 | 5 uM | 7.5 uM |
| Example 1a | 5 uM | 7.5 uM |
| Example 1b | 5 uM | 7.5 uM |

In Vivo Cancer Model

To assess the in vivo effects of the compounds, subcutaneous xenograft of lung cancer cell line H441 was generated. Cells (5×10$^6$) were injected into the right flank of 6- to 8-week-old male BALB/c nu/nu mice (Charles River, Wilmington, Mass.). Tumor volume was assessed twice a week by caliper measurement. Mice were randomized to treatment groups based on initial tumor volume average of 100 mm$^3$ per group. Mice were dosed by oral gavage with 15 mg/kg Example 1a QD, 15 mg/kg Example 1a BID, 50 mg/kg Example 1a QD, or 50 mg/kg Example 3a QD. Mouse tumors were measured twice a week for the duration of the study. Mouse body weights were recorded weekly and percentage of mice body weights during treatment was calculated as: weight at each time point/initial weight×100. Animals were observed for signs of toxicity (mucous diarrhea, abdominal stiffness and weight loss) and no adverse signs were observed. Mice underwent treatment for 30 days and were sacrificed 2 hours after the last dose. Tumors were then excised and cut for both formalin-fixation and snap frozen in liquid nitrogen. Compounds showed statistically significant, dose dependant, inhibition of tumor (T) growth versus vehicle control (C) as shown in the Table A below. No statistically significant toxicity was observed as judged from animal body weights of compound treated groups versus vehicle control group as shown in Table B below.

TABLE A

| Compound; dose; frequency | Mean Tumor Volume(T) | % T/C | Median Tumor Volume(T) | % T/C | Standard error | Student's ttest |
|---|---|---|---|---|---|---|
| Vehicle Contol(C) DMA:solutol:water (10:10:80) | 1209.23 | 100.00 | 1002.74 | 100.00 | 309.23 | |
| Example 1a; 50 mg/kg; QD | 441.37 | 36.50 | 338.69 | 33.78 | 106.96 | 0.02 |

TABLE A-continued

| Compound; dose; frequency | Mean Tumor Volume(T) | % T/C | Median Tumor Volume(T) | % T/C | Standard error | Student's ttest |
|---|---|---|---|---|---|---|
| Example 1a; 15 mg/kg; QD | 742.80 | 61.43 | 608.58 | 60.69 | 196.79 | 0.15 |
| Example 1a; 15 mg/kg; BID | 315.40 | 26.08 | 274.43 | 27.37 | 74.24 | 0.01 |
| Example 3a; 50 mg/kg; QD | 388.47 | 32.13 | 377.21 | 37.62 | 44.66 | 0.01 |

TABLE B

| Compound; dose; frequency | Mean body weight/g | % T/C | Median body weight/g | % T/C | Standard error | Student's ttest |
|---|---|---|---|---|---|---|
| Vehicle Control(C) DMA:solutol:water (10:10:80) | 34.85 | 100.00 | 35.60 | 100.00 | 1.24 | |
| Example 1a; 50 mg/kg; QD | 35.06 | 100.59 | 35.50 | 99.72 | 1.23 | 0.90 |
| Example 1a; 15 mg/kg; QD | 33.20 | 95.27 | 33.35 | 93.68 | 1.55 | 0.35 |
| Example 1a; 15 mg/kg; BID | 33.20 | 95.27 | 35.45 | 99.58 | 1.65 | 0.39 |
| Example 3a; 50 mg/kg; QD | 32.74 | 93.96 | 33.00 | 92.70 | 1.31 | 0.21 |

While typical embodiments have been set forth for the purpose of illustration, the foregoing descriptions and examples should not be deemed to be a limitation on the scope of the invention. Accordingly, various modifications, adaptations, and alternatives may occur to one skilled in the art without departing from the spirit and scope of the present invention.

We claim:

1. A compound of formula (I):

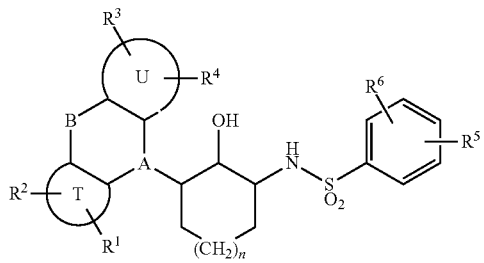

wherein:
B is selected from the group consisting of: direct bond, —O—, —(CH$_2$—O)—, —(O—CH$_2$)—, —C(=O)N(CH$_3$)— and —N(CH$_3$)C(=O)—;
A is selected from N and CH;
T is a benzene ring or a five or six membered heteroaromatic ring;
U is a benzene ring or a five or six membered heteroaromatic ring;
n is zero, 1 or 2;
$R^1$, $R^2$, $R^3$ and $R^4$ are chosen independently from H, OH, halogen, cyano, nitro, (C$_1$-C$_3$)alkylamino, (C$_1$-C$_3$)dialkylamino, (C$_1$-C$_3$)acylamino, (C$_1$-C$_3$)alkylsulfonyl, (C$_1$-C$_3$)alkylthio, (C$_1$-C$_3$)alkyl, (C$_1$-C$_3$)haloalkyl, (C$_1$-C$_3$)haloalkoxy, —CC(=O)O(C$_1$-C$_3$)alkyl, and (C$_1$-C$_3$) alkoxy;
$R^5$ and $R^6$ are chosen independently from H, halogen, cyano, nitro, azido, (C$_1$-C$_3$)haloalkyl, (C$_1$-C$_3$)haloalkoxy, and (C$_1$-C$_3$) haloalkylthio.

2. A compound according to claim 1 of formula (II):

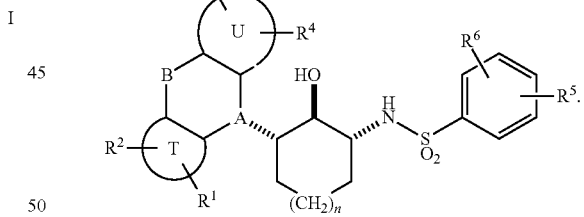

3. A substantially pure single enantiomer according to claim 2 of formula IIIa or IIIb:

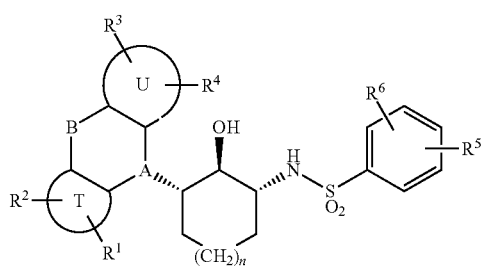

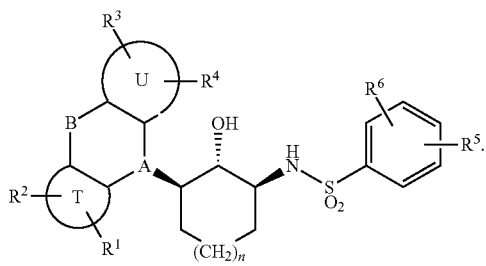

IIIb

4. A compound according to claim 1 wherein n is one.
5. A compound according to claim 1 wherein n is zero.
6. A compound according to claim 1, wherein B is a direct bond.
7. A compound according to claim 1, wherein B is —O—.
8. A compound according to claim 1, wherein B is —(CH$_2$—O)— or —(O—CH$_2$)—.
9. A compound according to claim 1, wherein B is —C(=O)N(CH$_3$)— or —N(CH$_3$)C(=O)—.
10. A compound according to claim 1, wherein A is N.
11. A compound according to claim 1, wherein A is —CH.
12. A compound according to claim 1, wherein T and U are both benzene rings.
13. A compound according to claim 1, wherein one of T and U is a benzene ring, and the other of T and U is selected from pyridine, pyrimidine, and thiophene.
14. A compound according to claim 1, wherein R$^2$ and R$^4$ are H, and R$^1$ and R$^3$ are chosen independently from H, OH, F, Cl, Br, CN, CO$_2$CH$_3$, CH$_3$, CF$_3$, OCF$_3$, and OCH$_3$.
15. A compound according to claim 1, wherein R$^5$ is H, and R$^6$ is chosen from H, F, Cl, CF$_3$, OCF$_3$, SCF$_3$, N$_3$ and CN.
16. A compound according to claim 15 wherein R$^6$ is in the para position.
17. A method for treating a disease in a patient chosen from:
 breast cancer, prostate cancer, leukemia, lung cancer, and glioblastoma;
the method comprising administering to the patient a therapeutically effective amount of a compound according to claim 1.
18. A pharmaceutical composition comprising a pharmaceutically acceptable carrier and a compound according to claim 1.
19. A compound according to claim 1 selected from:

| Example No. | Structure |
|---|---|
| 1 | (structure) |
| 1a | (structure) |
| 1b | (structure) |
| 2 | (structure) |
| 3 | (structure) |
| 3a | (structure) |

-continued
| Example No. | Structure |
|---|---|
| 3b | 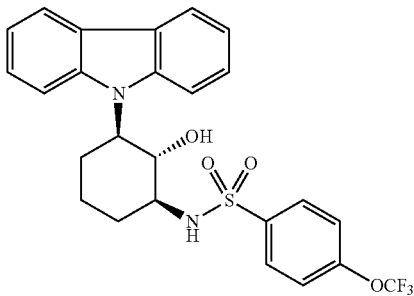 [SMILES: O=S(=O)(N[C@H]1CCC[C@@H](n2c3ccccc3c3ccccc32)[C@@H]1O)c1ccc(OC(F)(F)F)cc1] |
| 4 | 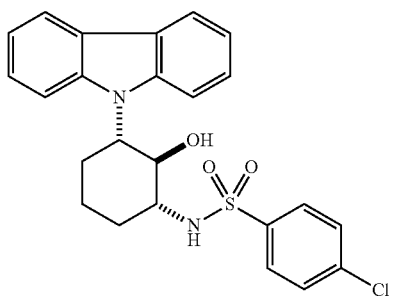 |
| 5 | 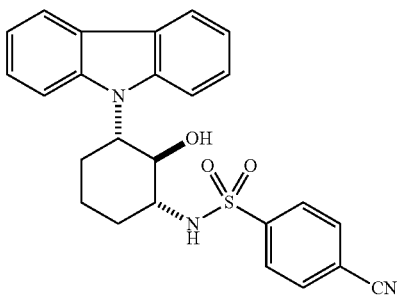 |
| 6 | 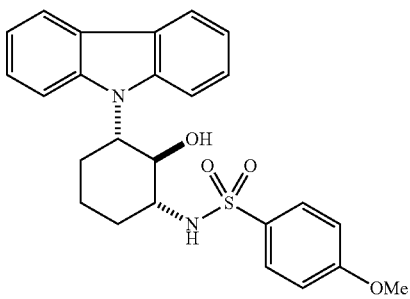 |
| 7 | 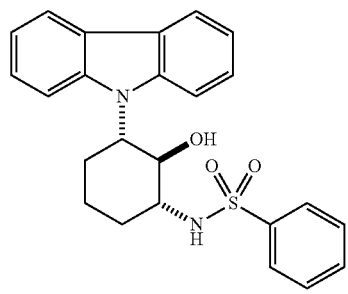 |
-continued
| Example No. | Structure |
|---|---|
| 8 | 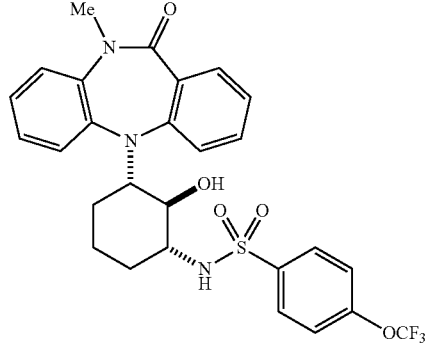 |
| 9 | 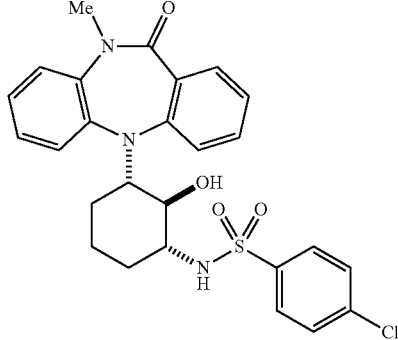 |
| 10 | 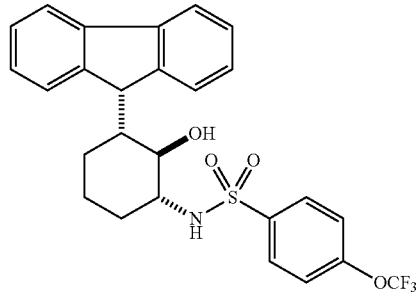 |
| 12 | 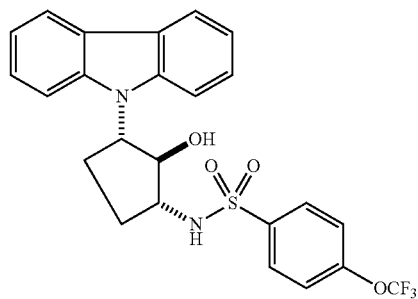 |

| Example No. | Structure |
|---|---|
| 13 | 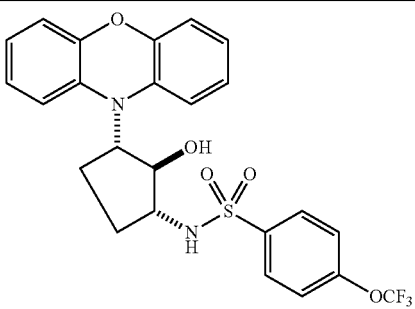 |
| 14 | 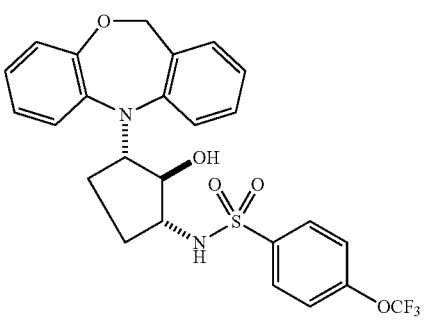 |
| 15 | 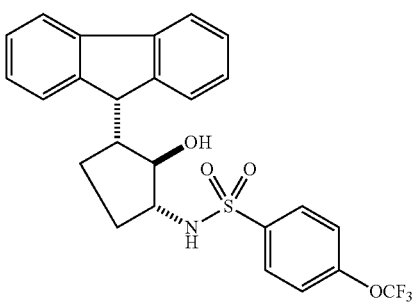 |
| 16 | 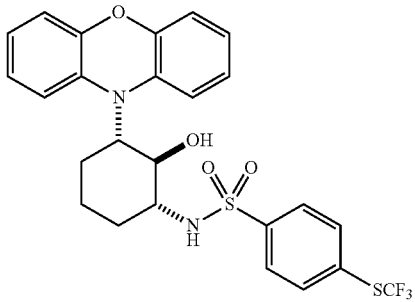 |
| 17 | 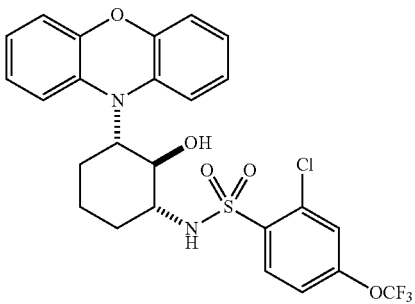 |
| 18 | 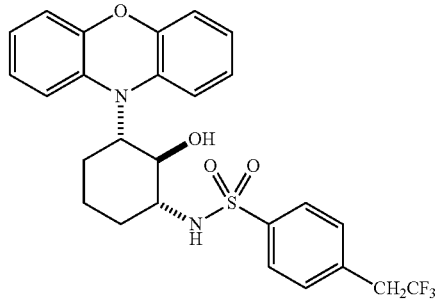 |
| 19 | 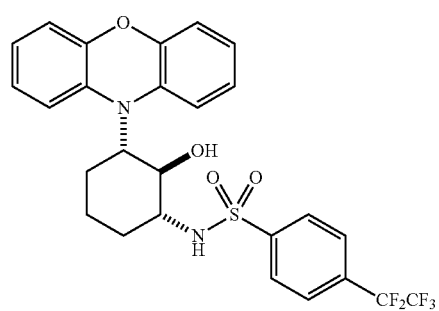 |
| 20 | 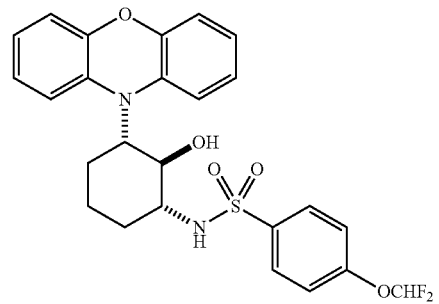 |
| 21 | 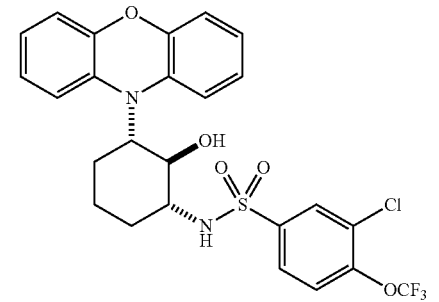 |
| 22 | 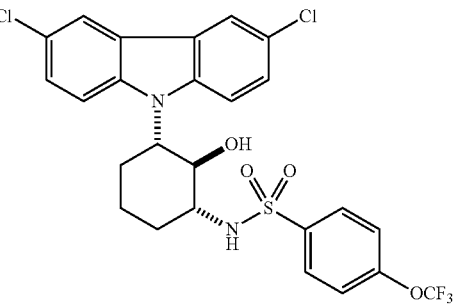 |

-continued
| Example No. | Structure |
|---|---|
| 23 | 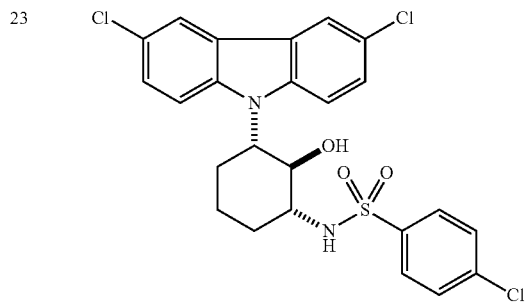 |
| 24 | 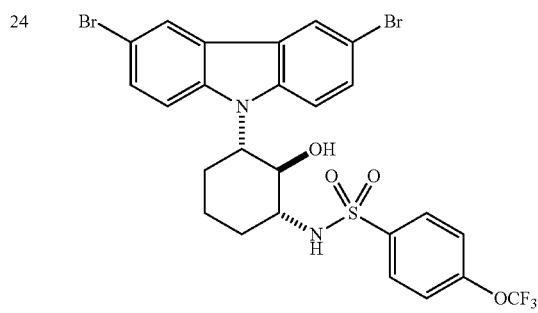 |
| 25 | 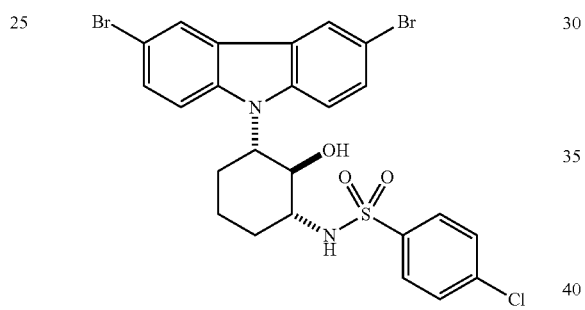 |
| 26 | 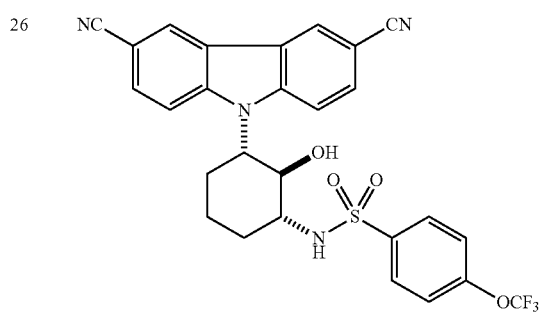 |
| 27 | 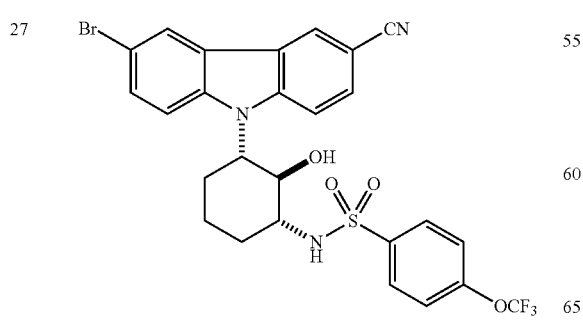 |
-continued
| Example No. | Structure |
|---|---|
| 28 | 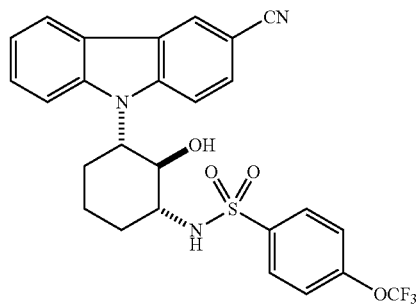 |
| 29 | 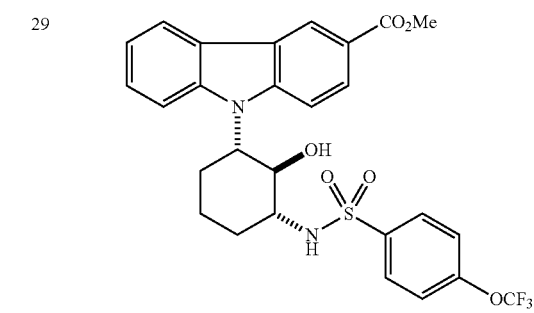 |
| 30 | 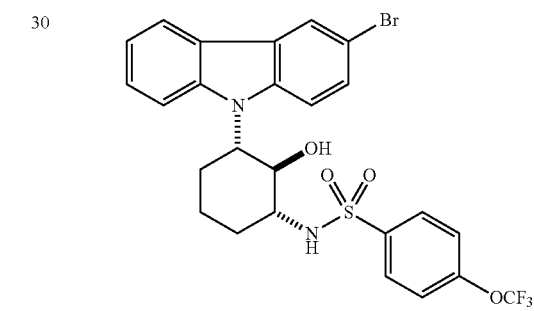 |
| 31a | 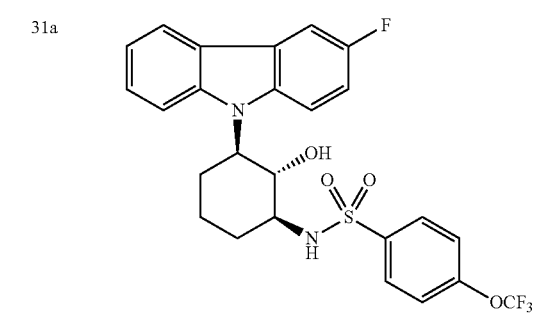 |
| 31b | 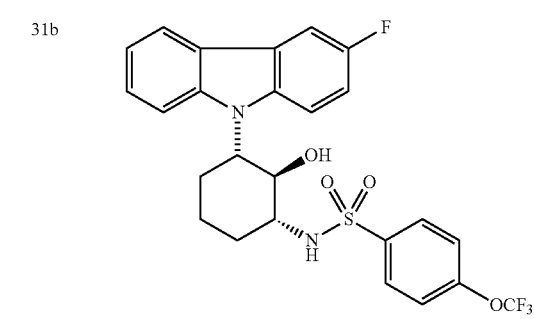 |

| Example No. | Structure |
|---|---|
| 32a | 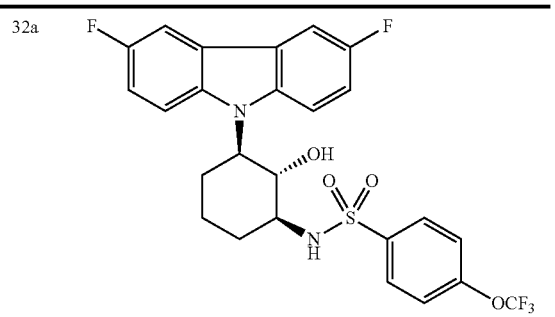 |
| 32b | 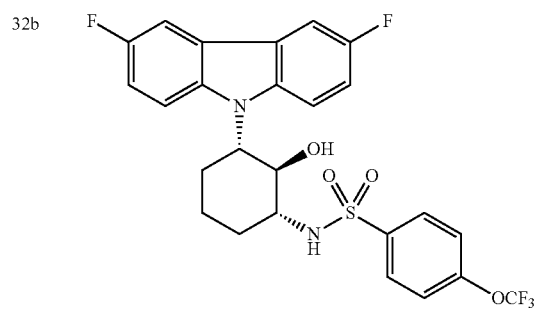 |
| 34 | 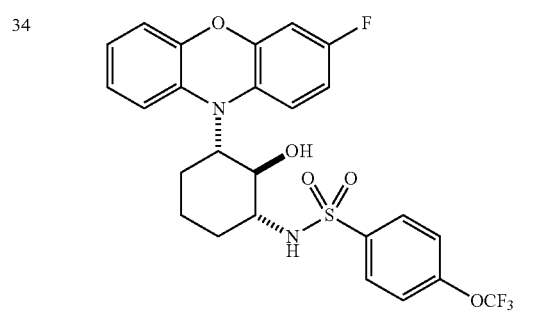 |
| 35 | 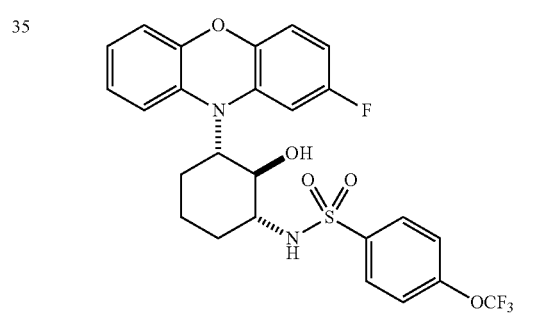 |
| 36 | 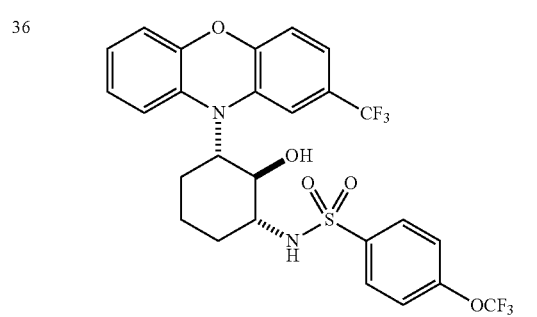 |
| Example No. | Structure |
|---|---|
| 37 | 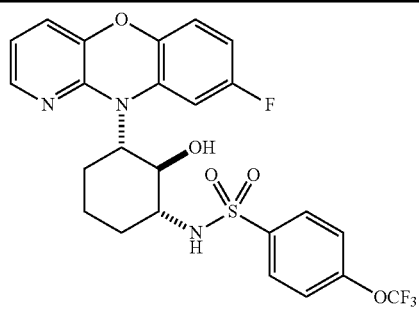 |
| 38 | 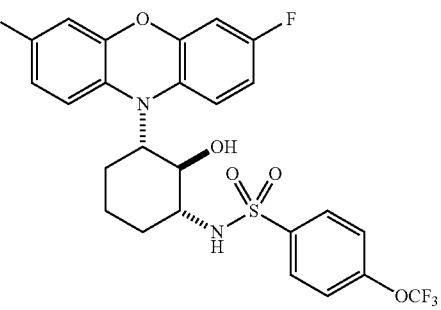 |
| 39 | 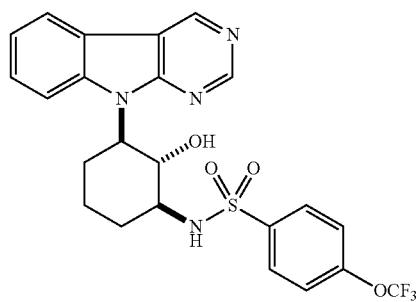 |
| 40 | 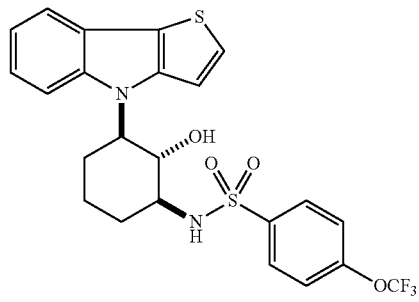 |
| 41 | 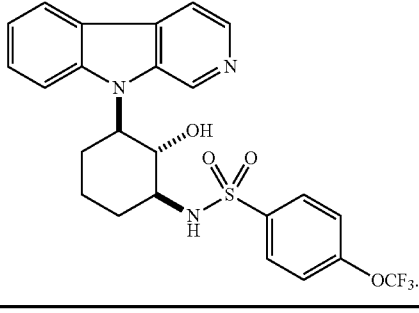 |
* * * * *